United States Patent
Dixit et al.

(10) Patent No.: US 10,100,105 B2
(45) Date of Patent: Oct. 16, 2018

(54) ANTI-POLYUBIQUITIN ANTIBODIES AND METHODS OF USE

(71) Applicant: Genentech, Inc., South San Francisco, CA (US)

(72) Inventors: Vishva Dixit, Los Altos, CA (US); Robert F. Kelley, San Bruno, CA (US); Marissa L. Matsumoto, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 132 days.

(21) Appl. No.: 15/381,452

(22) Filed: Dec. 16, 2016

(65) Prior Publication Data

US 2017/0240620 A1 Aug. 24, 2017

Related U.S. Application Data

(62) Division of application No. 14/627,597, filed on Feb. 20, 2015, now Pat. No. 9,556,262, which is a division of application No. 13/086,941, filed on Apr. 14, 2011, now Pat. No. 8,992,919.

(60) Provisional application No. 61/324,602, filed on Apr. 15, 2010.

(51) Int. Cl.
*C07K 16/00* (2006.01)
*C07K 16/18* (2006.01)
*C12N 15/10* (2006.01)

(52) U.S. Cl.
CPC .......... *C07K 16/18* (2013.01); *C12N 15/1037* (2013.01); *C07K 2317/24* (2013.01); *C07K 2317/55* (2013.01); *C07K 2317/56* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,763,245 | B2 | 7/2010 | Gordon et al. |
| 8,133,488 | B2 | 3/2012 | Kelley et al. |
| 8,603,475 | B2 | 12/2013 | Gordon et al. |
| 8,992,919 | B2 | 3/2015 | Dixit et al. |
| 2005/0106667 | A1 | 5/2005 | Fellouse et al. |
| 2005/0119455 | A1 | 6/2005 | Fuh et al. |
| 2007/0166778 | A1 | 7/2007 | Rain et al. |
| 2007/0218069 | A1 | 9/2007 | Gordon et al. |
| 2007/0218079 | A1 | 9/2007 | Patzel |
| 2007/0248536 | A1 | 10/2007 | Fiedler et al. |
| 2009/0191209 | A1 | 7/2009 | Kelley et al. |
| 2010/0267050 | A1 | 10/2010 | Gordon et al. |
| 2013/0058955 | A1 | 3/2013 | Kelley et al. |
| 2015/0307602 | A1 | 10/2015 | Dixit et al. |

FOREIGN PATENT DOCUMENTS

| | | |
|---|---|---|
| CN | 1845994 A | 10/2006 |
| CN | 101084237 A | 12/2007 |
| JP | 07238096 | 9/1995 |
| WO | WO 2004/003019 A2 | 1/2004 |
| WO | WO 2005/014804 A2 | 2/2005 |
| WO | WO 2007/025216 A2 | 3/2007 |
| WO | WO 2007/120334 A2 | 10/2007 |
| WO | WO 2008/121813 A2 | 10/2008 |
| WO | WO 2009/126350 A2 | 10/2009 |
| WO | WO 2011/130499 A1 | 10/2011 |
| WO | WO 2013/022848 A1 | 2/2013 |

OTHER PUBLICATIONS

"Product information sheet for BIOMOL catalogue No. PW8805" pp. 1-2 (Jan. 25, 2004).
Alves-Rodrigues et al., "Ubiquitin, cellular inclusions and their role in neurodegeneration" Trends in Neurosciences 21(12): 516-520 (1998).
Beckmann et al., "The ubiquitin-modifying enzyme A20 is required for termination of toll-like receptors responses" Nature Immunol. 5(10): 1052-1060 (Oct. 2004).
Bodine et al., "Identification of ubiquitin ligases required for skeletal muscle atrophy" Science 294(5547): 1704-1708 (Nov. 23, 2011).
Boone, D. L. et al., "The ubiquitin-modifying enzyme A20 Is required for termination of toll-like receptor responses" Nature Immunol. 5(10): 1052-1060 (Oct. 2004).
Brorson, "Mutational analysis of avidity and fine specificity of anti-levan antibodies" J Immunol (added article title info, 163:6694-6701 (Dec. 1999).
Brummel e al., "Probing the combining site of an anti-carbohydrate antibody by saturation-mutagenesis: role of heavy-chain CDR3 residues" Biochemistry 32(4): 1180-1187 (Feb. 1993).
Burks, E., et al., "In vitro scanning saturation mutagenesis of an antibody binding pocket" Proc. Natl. Acad. Sci. 94:412-417 (1997).
Cammarata et al., Ubiquitin-reactive neurites in cerebral cortex of subjects with Huntington's chorea: a pathological correlate of dementia? Neuroscience Letters 156(1-2):96-98 (1993).
Campbell, A. Monoclonal Antibody Technology "1" The Netherlands: Elsevier Science Publishers B.V., :1-32 (1984).
Carrion-Vazquez et al., "The mechanical stability of ubiquitin is linkage dependent" Nat Struct Biol. (Epub Aug. 17, 2003) 10(9):738-743 (Sep. 2003).
Casset. F. et al., "A peptide mimetic of an anti-CD4 monoclonal antibody by rational design" Biochem. & Biophys. Res. Comm. 307;198-205 (2003).
Chau et al., A multiubiquitin chain is confined to specific lysine in a targeted short-lived protein Science 243(4898):1576-1583 (Mar. 24, 1989).
Chen et al., "Structural basis for scaffolding-mediated assembly and maturation of dsDNA virus" Proc Natl Acad Sci U S A. 108(4):1355-60 (Jan. 2011).
Chen, Y. et al., "Selection and analysis of an optimized anti-VEGF antibody: crystal structrure of an affinity-matured Fab in complex with antigen" J. Mol. Biol. 293:865-881 (1999).

(Continued)

*Primary Examiner* — Mark Halvorson
(74) *Attorney, Agent, or Firm* — McNeill Baur PLLC

(57) ABSTRACT

The invention provides anti-polyubiquitin antibodies and methods of using the same.

24 Claims, 17 Drawing Sheets
Specification includes a Sequence Listing.

(56) References Cited

OTHER PUBLICATIONS

Chung et al., "The role of ubiquitin-proteasomal pathway in Parkinson's disease and other neurodegenerative disorders" Trends in Neurosciences 24(11 Suppl):S7-14 (Nov. 2001).
Ciechanover, "The ubiquitin-proteasome pathway: on protein death and cell life" EMBO Journal 17(24):7151-7160 (1998).
Clark, L. A. et al., "Affinity enhancement of an in vivo matured therapeutic antibody using structure-based computational design" Prot. Sci. 15:949-960 (2006).
Coleman, P.M., "Effects of amino acid sequence changes on antibody-antigen interactions" Res Immunol 145:33-36 (1994).
Cook, W. J. et al., "Structure of diubiquitin conjugate and a model for interaction with ubiquitin conjugating enzyme (E2)" Journal of Biological Chemistry 267(23):16467-16471 (Aug. 15, 1992).
International Search Report and Written Opinion for International Patent Application No. PCT/US2009/031310, Authorized Officer: P. Bumb, dated Oct. 16, 2009 (22 pages).
International Search Report and Written Opinion for International Patent Application No. PCT/US2011/032468, Authorized Officer: A. Premkumar, dated Jun. 3, 2011 (10 pages).
International Search Report for PCT/US/2006/062115, Authorized Officer: M. Weikl, dated Apr. 10, 2008 (5 pages).
Crosas, B. et al., "Ubiquitin chans are remodeled at the proteasome by opposing ubuiquitin ligases and deubiquitinating activities" Cell 127:1401-1413 (Dec. 29, 2006).
De Pascalis et al., "Grafting of "abbreviated" complementarity-determining regions containing specificity-determining residues essential for ligand contact to engineer a less immunogenic humanized monoclonal antibody" J. Immunol. 169:3076-3084 (2002).
Deng et al., "Activation of the IkappaB kinase complex by TRAF6 requires a dimeric ubiquitin-conjugating enzyme complex and a unique polyubiquitin chain" Cell 103(2):351-361 (Oct. 13, 2000).
Dufner et al., "Harnessing phage and ribosome display for antibody optimisation" Trends in Biotechnology 24(11):523-529 (2006).
Fellouse et al., "High-throughput generation of synthetic antibodies from highly functional minimalist phage-displayed libraries" J Mol Biol. 373(4):924-40 (Nov. 2007).
Finley et al., "Inhibition of proteolysis and cell cycle progression in a multibiquitination-deficient yeast mutant" Mol Cell Biol. 14(8):5501-5509 (Aug. 1994).
Flick et al., "Proteolysis-independent regulation of the transcription factor Met4 by a single Lys 48-linked ubiquitin chain" Nat Cell Biol. (epub Jun. 20, 2004) 6(7):634-641 (Jul. 2004).
Fujimuro and Yokosawa, "Production of antipolyubiquitin monoclonal antibodies and their use for characterization and isolation of polyubiquitinated proteins" Methods of Enzymology 399:75-86 (Dec. 15, 2005).
Fujimuro et al., "Production and characterization of monoclonal antibodies specific to multi-ubiquitin chains of polyubiquitinated proteins" FEBS Letters 349(2):173-180 (1994).
Gallop et al., "Applications of combinatorial technologies to drug discoveries. 1. background and peptide combinatorial libraries" J Med Chem 37(9):1233-1251 (1994).
Garnett et al., "UBE2S elongates ubiquitin chains on APC/C substrates to promote mitotic exit" Nat Cell Biol. 11(11):1363-9 (2009).
Ghosh and Karin, "Missing pieces in the NF-kappaB puzzle" Cell 109(Suppl.):S81-S96 (Apr. 2006).
Gorman et al., "Transient Production of Proteins Using an Adenovirus Transformed Cell Line" DNA Prot. Eng. Tech. 2(1):3-10 (1990).
Guterman and Glickman, "Deubiquitinating enzymes are IN/(trinsic to proteasome function)" Curr Protein Pept Sci. 5(3):201-544 (2004).
Hashizume et al., "The RING heterodimer BRCA1-BARD1 is a ubiquitin ligase inactivated by a breast cancer-derived mutation" J Biol Chem. 276(18):14537-14540 (May 4, 2001).
Hicke and Dunn, "Regulation of membrane protein transport by ubiquitin and ubiquitin-binding proteins" Annu Rev Cell Dev Biol. (epub Jun. 20, 2003) 19:141-172 (2003).

Hicke, L., "Protein regulation by monoubiquitin" Nature Reviews Mol. Cell Biol. 2:195-201 (Mar. 2001).
Hoege et al., "RAD6-dependent DNA repari is linked to modication of PCNA by ubiquitin and SUMO" Nature 419(6903):134-141 (Sep. 12, 2002).
Hofmann and Pickart, "In vitro assempy and recognition of Lys-63 polyubiquitin chains" J Biol Chem. 276(30):24736-27943 (Jul. 27, 2001).
Hofmann and Pickart, "Noncanonical MMS2-encoded ubiquitin-conjugatting enzyme functions in assembly of novel polyubiquitin chains for DNA repair" Cell 96(5):645-653 (Mar. 5, 1999).
Holm, et al., "Functional mapping and single chain construction of the anti-cytokeratin 8 monoclonal antibody TS1" Molucular Immunology 44:1075-1084 (2007).
Holmberg et al., "Spinocerebellar ataxia type 7 (SCA7): a neurodegenerative disorder with neuronal intranuclear inclusions" Hum Mol Genet. 7(5):913-918 (1998).
Jang et al., "The structural basis for DNA binding by an anti-DNA autoantibody," Mol. Immunol., 35(18): 1207-17 (Dec. 1998).
Jin et al., "Mechanism of ubiquitin-chain formation by the human anaphase-promoting complex," Cell 133(4): 653-65 (May 2008).
Johnson, "Ubiquitin branches out" Nat Cell Biol. 4(12):E295-E298 (Dec. 2002).
Kalchman et al., "Huntingtin is ubiquitinated and interacts with a specific ubiquitin-conjugating enzyme" J Biol Chem., 271(32):19385-19394 (Aug. 9, 1996).
Kim, H. T. et al., "Certain pairs of ubiquitin-conjugating enzymes (E2s) and ubiquitin-protein ligases (E3s) synthesize nondegradable forked ubiquitin chains containing all possible isopeptide linkages" Journal of Biological Chemistry 282(24):17375-17386 (Jun. 15, 2007).
Kirkpatrick, D. S. et al., "Quantitative analysis of in vitro ubiquitinated cyclin B1 reveals complex chain topology" Nature Cell Biol. 8(7):700-710 (Jul. 2006).
Kishino et al., "UBE3A/E6-AP mutations cause Angelman syndrome" Nat Genet. 15(1):70-73 (Jan. 1997).
Kobayashi, H., et al., "Tryptophan H33 plays an important role in pyrimidin (6-4) pyrimidone photoproduct binding by a high-affinity antibody" Protein Engineering 12(10):879-884 (1999).
Kumar, Sanjeev, et al., "Molecular cloning and expression of the fabs of human autoantibodies in *Escherichia coli*" J. Bio. Chem. 275(45):35129-35136 (2000).
Kunkel, "Rapid and Efficient Site-Specific Mutagenesis Without Phenotypic Selection" Proc. Natl. Acad. Sci.:488-492 (Jan. 1985).
Kuzuhara et al., "Lewy bodies are ubiquitinated. A light and electron microscopic immunocytochemical study" Acta Neuropathology (Berl) 75(4):345-353 (1988).
Lam et al., "Inhibition of the ubiquitin-proteasome system in Alzheimer's disease" Proc Natl Acad Sci USA 97(18):9902-9906 (Aug. 29, 2000).
Lee et al., "High-affinity human antibodies from phage-displayed synthetic Fab libraries with a single framework scaffold" J. Mol. Biol. 340(5):1073-1093 (2004).
Leigh et al., "New aspects of the pathology of neurodegenerative disorders as revealed by ubiquitin antibodies" Acta Neuropathol. 79(1)61-72 (1989).
Leroy et al., "The ubiquitin pathway in Parkinson's disease" Nature 395(6701):451-452 (Oct. 1, 1998).
Lim et al., "Parkin mediates nonclassical, proteasomal-independent ubiquitination of synphilin-1:implicaitons for Lewy body formation" J Neurosci. 25(8):2002-2009 (Feb. 23, 2005).
MacCallum et al., "Antibody-antigen Interactions: Contact Analysis and Binding Site Topography" J. Mol.Biol. 262:732-745 (1996).
Majetschak et al., "Extracellular ubiquitin inhibits the TNF-alpha response to endotoxin in peripheral blood mononuclear cells and regulates endotoxin hyporesponsive in critical illness" Blood 101(5):1882-1890 (Mar. 1, 2003).
Matsumoto et al., "K11-linked polyubiquitination in cell cycle control revealed by a K11 linkage-specific antibody" Mol Cell 39(3):477-84 (Aug. 2010).
McNaught et al., "Failure of the ubiquitin-proteasome system in Parkinson's diseease" Nat Rev Neurosci. 2(8):589-594 (Aug. 2001).

(56) References Cited

OTHER PUBLICATIONS

Mitch and Goldberg, "Mechanisms of muscle wasting. The role of the ubiquitin-proteasome pathway" N Engl J Med. 335(25):1897-1905 (Dec. 19, 1996).
Mori et al., "Ubiquitin is a component of paired helical filaments in Alzheimer's disease" Science 235(4796):1641-1644 (Mar. 27, 1987).
Naze et al., "Mutation analysis and association studies of the ubiquitin carboxy-terminal hydrolase L1 gene in Huntington's disease" Neuroscience Letters 328(1):1-4 (2002).
Nemes, Z. et al., "Cross-linking of ubiquitin, HSP27, parking and α-synuclein by /147-gluamyl-ε-lysine bonds in Alzheimer's nurofibrillary tangles" FASEB J. 18(10):1135-7 (May 2004).
Newton, K. et al., "Ubiquitin chain editing revealed by polyubiquitin linkage-specific antibodies" Cell 134:668-678 (Aug. 22, 2008).
Palombella et al., "The ubiquitin-proteasome pathway is required for processing the NF-kappa B1 precursor protein and the activation of NF-kappa B" Cell 78(5):773-785 (Sep. 9, 1994).
Peng et al., "A proteomics approach to understanding protein ubiquitination" Nat Biotechnol. 21(8):921-926 (Aug. 2003).
Pickart and Fushman, "Polyubiquitin chains: polymeric protein signals" Curr Opin Chem Biol. (epub Oct. 28, 2004) 8(6):610-616 (Dec. 2004).
Pickart, "Mechanisms underlying ubiquitination" Annu Rev Biochem. 70:503-533 (2001).
Pickart, "Ubiquitin enters the new millennium" Mol Cell. 8(3):499-504 (Sep. 2011).
Rudikoff, et al., "Single amino acid substitution altering antigen-binding specificity" Proc. Natl. Acad. Sci. USA 79:1979-1983 (1982).
Salghetti et al., "Destruction fo Myc by ubiquitin-mediated proteolysis: cancer-associated and transforming mutations stabilize Myc" EMBO Journal 18(3):717-726 (1999).
Seibenhener et al., "Sequestosome 1/p62 is a polyubiquitin chain binding protein involved in ubiquitin proteasome degradation" Mol Cell Biol. 24(18):8055-8068 (Sep. 2004).
Shimura et al., "Familial Parkinson disease gene product, parkin, is a ubiquitin-protein ligase" Nat Genet. 25(3):302-305 (Jul. 2000).
Smith-Gill, S., et al., "Contributions of immunoglobulin heavy and light chains to antibody specificity for lysozyme and two haptens" J. immunol. 139:4135-4144 (1987).
Song, Mi-Kyung, et al., "Light chain of natural antibody plays a dominant role in protein antigen binding" Biochem Biophys Res. Comm 268:390-394 (2000).
Spataro et al., "The ubiquitin-proteasome pathway in cancer" Br J Cancer 77(3):448-455 (1998).
Spence et al., "A ubiquitin mutant with specific defects in DNA repair and multiubiquitination" Mol Cell Biol. 15(3):1265-1273 (Mar. 1995).
Spence et al., "Cell cycle-regulated modification of the ribosome by variant multiubiquitin chain" Cell 102(1):67-76 (Jul. 7, 2000).
Staub et al., "Regulation of stability and function of the epithelial Na+ channel (ENaC) by ubiquitination" EMBO Journal 16(21):6325-6336 (1997).
Stelter and Ulrich, "Control of spontaneous and damage-induced mutagenesis by SUMO and ubiquitin combination" Nature 425(6954):188-191 (Sep. 11, 2003).
Sun and Chen, "The novel functions of ubiquitination in signaling" Curr Opin Cell Biol. 16(2):119-126 (2004).
Takada et al., "Serum concentrations of free ubiquitin and multiubiquitin chains" Clin Chem. 43(7):1188-1195 (1997).
Tan, J. et al., "Lysine 63-linked ubiquitination promotes the formation and autophagic clearance of protein inclusions associated with neurodegenerative diseases" Human Mol Genetics 17(3):431-439 (Mar. 2008).
Tenno et al., "Structural basis for distinct roles of Lys63- and Lys48-linked polyubiquitin chains" Genes Cells 9(10):865-875 (2004).
Treier et al., "Ubiquitin-dependent c-Jun degradation in vivo is mediated by the delta domain" Cell 78(5):787-798 (Sep. 9, 1994).

Ulrich, "Degradation or maintenance: actions of the ubiquitin system on eukaryotic chromatin" Eukaryotic Cell 1(1):1-10 (Feb. 2002).
Vajdos et al., "Comprehensive functional maps of the antigen-binding site of an anti-ErbB2 antibody obtained with shotgun scanning mutagenesis" J. Mol. Biol. 320:415-428 (2002).
Vardan et al., "Structural properties of polyubiquitin chains in solution," J. Mol. Biol., 324: 637-647 (2002).
Ward et al., "Binding Activities of a Repertoire of Single Immunoglobulin Variable Domains Secreted from *Escherichia coli*" Nature 341:544-546 (Oct. 12, 1989).
Ward et al., "Degradation of CFTR by the ubiquitin-proteasome pathway" Cell 83(1):121-127 (Oct. 6, 1995).
Wertz et al., "De-ubiquitination and ubiquitin ligase domains of A20 downregulate NF-kappaB signalling" Nature 430:694-699 (Aug. 5, 2004).
Wilkinson, "Ubiquitination and deubiquitination targeting of proteins for degradation by the proteasome" Semin Cell Dev Biol. 11(3):141-148 (2000).
Williamson et al., "Identification of physiological E2 module for the human anaphase-promoting complex" Proc Natl Acad Sci USA. 106(43):18213-8 (Oct. 2009).
Wong et al., "Drug discovery in the ubiquitin regulatory pathway" Drug Discov Today 8(16):746-754 (Aug. 2003).
Wu et al., "Humanization of a Murine Monoclonal Antibody of Simultaneous Optimization of Frameworka nd CDR Residues" J. Mol. Biol. 294:151-162 (1999).
Yamin and Miller, "The interleukin-1 receptor-associated kinase is degraded by proteasomes following its phosphorylation" Journal of Biological Chemistry 272(34):21540-21547 (Aug. 22, 1997).
Yedidia et al., "Proteasome and ubiquitin are involved in the turnover of the wild-type prion protein" EMBO Journal 20(19):5383-5391 (2001).
Zhang et al., "Parkin functions as an E2-dependent ubiquitin-protein ligase and promotes the degradation of the synaptic vesicle-associated protein, CDCre1-1" Proc Natl Acad Sci USA. 94(24):13354-13359 (Nov. 21, 2000).
Lederman et al., Molecular Immunology, 28: 1171-1181 (1991).
Li et al., PNAS USA, 77: 3211-3214 (1980).
File history for U.S. Appl. No. 12/355,531, filed Jan. 16, 2009.
File history for U.S. Appl. No. 13/361,093, filed Jan. 30, 2012.
File history for U.S. Appl. No. 14/732,243, filed Jun. 5, 2015.
File history for U.S. Appl. No. 13/086,941, filed Apr. 14, 2011.
File history for U.S. Appl. No. 13/567,919, filed Aug. 6, 2012.
File history for U.S. Appl. No. 14/627,597, filed Feb. 20, 2015.
File history for U.S. Appl. No. 15/071,422, filed Mar. 16, 2016.
File history for U.S. Appl. No. 15/153,644, filed May 12, 2016.
Male, "Enzymatic Digestion of Human IgG1," from *Immunology*, 8th Ed. Male et al. eds., Elsevier Ltd., p. 110-111 (2013).
Communication of the Extended European Search Report and Opinion, for European Patent Application No. 10188648.9, dated Apr. 11, 2011 (7 pages).
Communication of the Extended European Search Report and Opinion, for European Patent Application No. 11769579.1, dated Dec. 3, 2013 (8 pages).
Communication of the Extended European Search Report and Opinion, for European Patent Application No. 12822145.4, dated Jan. 28, 2015 (7 pages).
International Search Report and Written Opinion for International Patent Application No. PCT/US2012/049771, dated Oct. 22, 2012 (11 pages).
Behrends et al., "Constructing and decoding unconventional ubiquitin chains," Nat. Structural Mol. Biol. 18(5): 520-528 (2011).
Komander et al., "Molecular discrimination of structurally equivalent Lys 63-linked and linear polyubiquitin chains," EMBO Reports 10(5): 466-473 (2009).
Matsumoto et al., "Engineering and Structural Characterization of a Linear Polyubiquitin-Specific Antibody," J. Mol. Biol. 418: 134-144 (2012).
Newton et al., "Chapter 13: Using Linkage-Specific Monoclonal Antibodies to Analyze Cellular Ubiquitylation," from *Methods in Molecular Biology*, vol. 832 (Clifton, NJ) 185-196 (2012).

(56) References Cited

OTHER PUBLICATIONS

Pirim et al., "Production of Anti-polyubiquitin and Anti-ubiquitin Carboxyl Terminal Hydrolsae Antibodies and Immunohistochemically Assessment of Them on Brain Sections of Alzheimer's Disease and Lewy Body Disease," Inter. J. Neuroscience 95: 33-42 (1998).
Tokunaga et al., "Involvement of linear polyubiquitylation of NEMO in NF-κB activation," Nature Cell Biol. 11(2): 123-132 and Supp. Info. pp. 1-17 (2009).

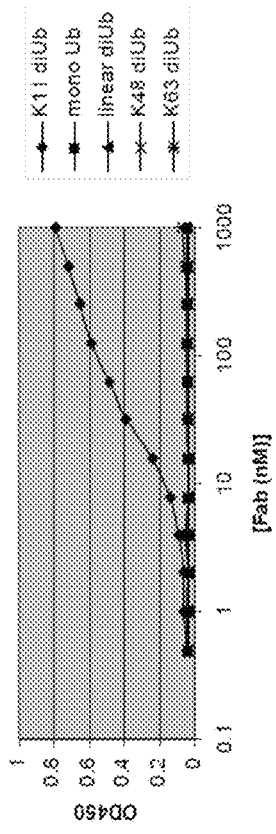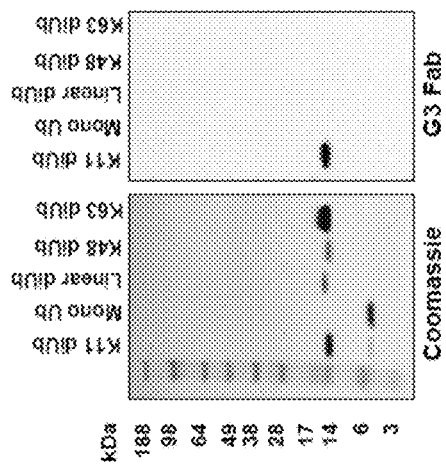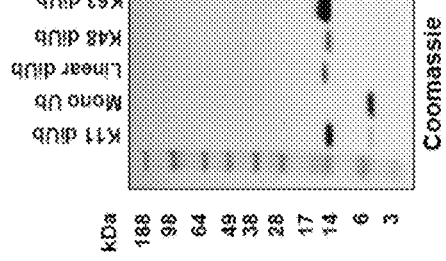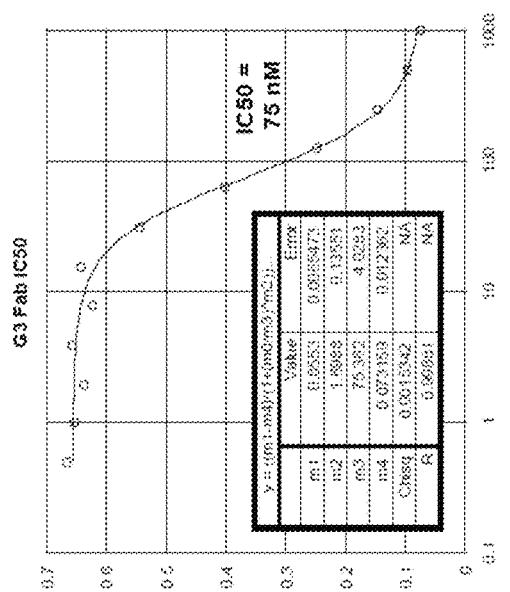
FIG. 3A
FIG. 3B
FIG. 3C

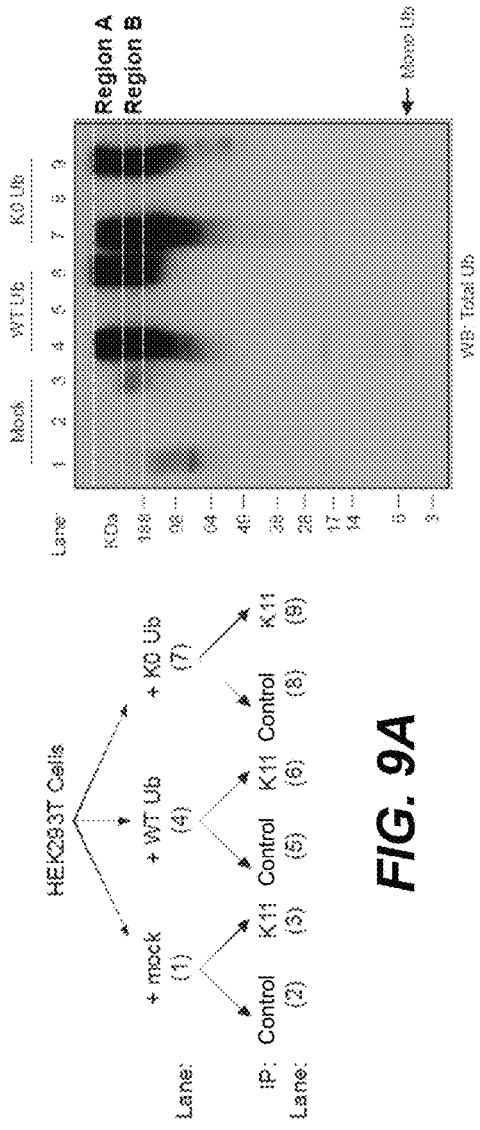
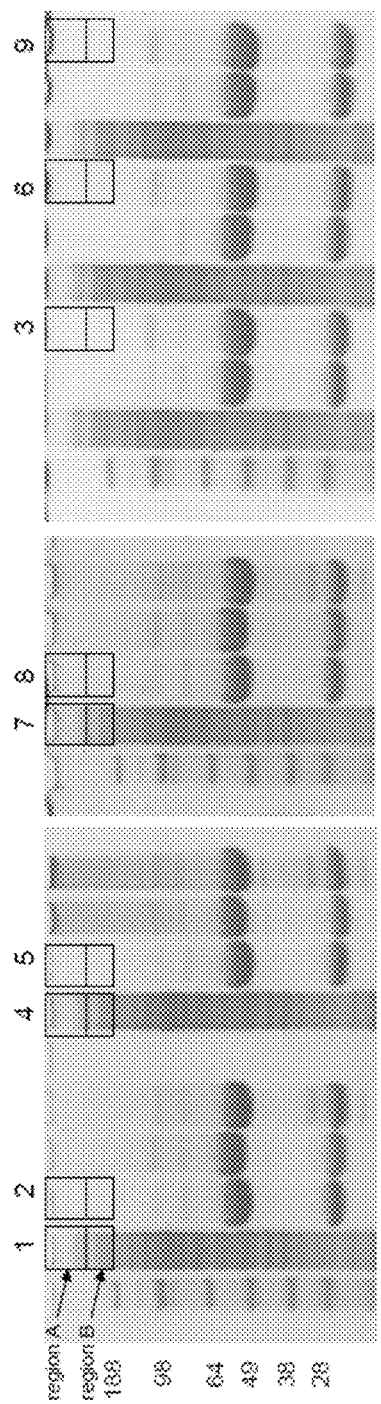
FIG. 9A
FIG. 9B

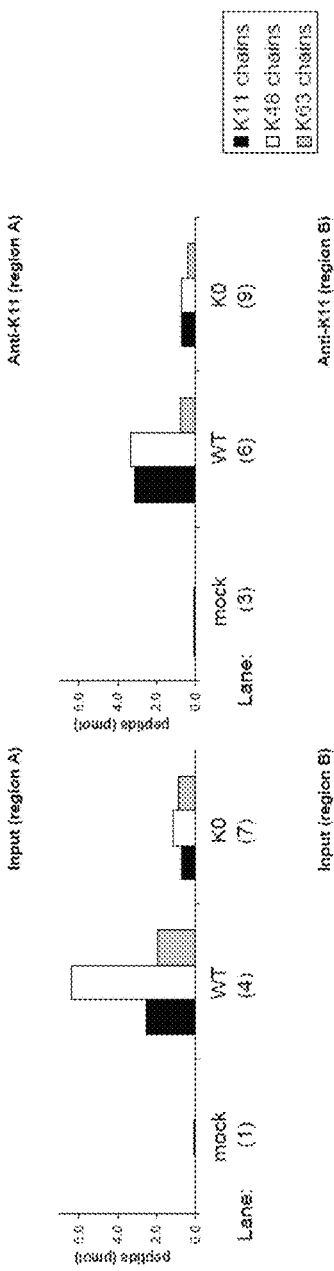
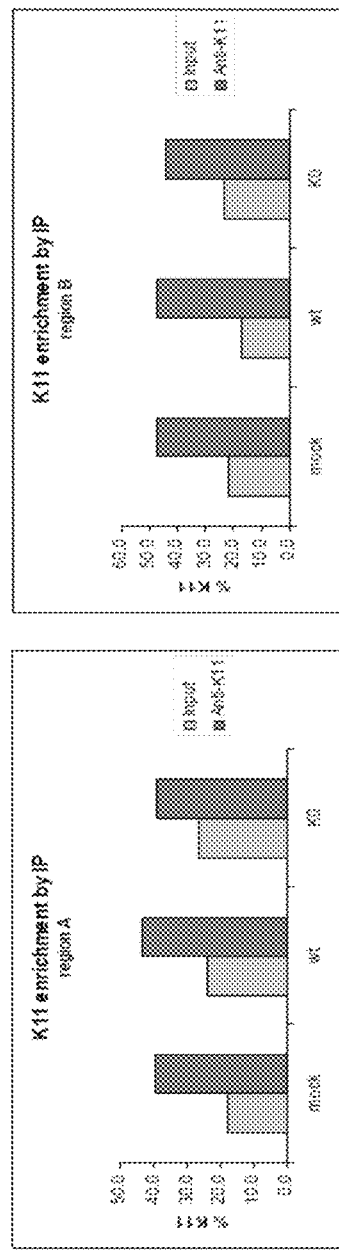
FIG. 9C
FIG. 9D

ANTI-POLYUBIQUITIN ANTIBODIES AND METHODS OF USE

RELATED APPLICATIONS

This application is a divisional of U.S. patent application Ser. No. 14/627,597, filed Feb. 20, 2015, which is a divisional of U.S. patent application Ser. No. 13/086,941, filed Apr. 14, 2011, now U.S. Pat. No. 8,992,919, which claims the benefit of U.S. Provisional Application No. 61/324,602 filed Apr. 15, 2010, each of which is incorporated by reference herein in its entirety.

REFERENCE TO SEQUENCE LISTING SUBMITTED AS A TEXT FILE VIA EFS-WEB

A sequence listing is submitted concurrently with the specification as an ASCII formatted text file via EFS-Web, with a file name of "01146-0012-02US_Sequence_Listing.txt", a creation date of Dec. 7, 2016, and a size of 40.0 kilobytes. The sequence listing filed via EFS-Web is part of the specification and is hereby incorporated by reference in its entirety herein.

FIELD OF THE INVENTION

The present invention relates to the field of anti-polyubiquitin antibodies, and more particularly to anti-polyubiquitin antibodies that do not specifically bind to monoubiquitin and that are specific for particular lysine linkage forms of polyubiquitin and methods of using the same.

BACKGROUND

Ubiquitin is a small protein that has important regulatory roles in a wide variety of cellular pathways. Ubiquitin chains linked through the lysine at position 11 (K11) have been identified as important regulators of cell division (Jin et al., 2008; Kirkpatrick et al., 2006) and have been implicated in signaling degradation of ubiquitin ligase anaphase-promoting complex (APC/C) substrates, an essential step in eukaryotic cell division (Jin et al., 2008; Williamson et al., 2009). The APC/C recruits two E2 enzymes, the ubiquitin chain-initiating UbcH10 and the chain elongating Ube2S, which assemble K11-linked chains with high specificity (Garnett et al., 2009; Williamson et al., 2009; Wu et al., 2010). Loss of this APC/C-specific E2 module leads to defects in mitotic progression (Williamson et al., 2009; Song and Rape, Molecular Cell in press). While these results suggest that K11-linked chains drive protein degradation by the proteasome during mitosis, characterization of ubiquitin chains assembled by the APC/C, UbcH10 and Ube2S has relied largely on in vitro experiments. Direct evidence of K11-linked polyubiquitin chains regulating protein degradation in cells has been lacking due to an absence of tools available to directly detect them.

SUMMARY

The invention provides anti-K11-linked polyubiquitin antibodies and methods of using the same. In one embodiment, the invention provides an isolated antibody that specifically binds a first polyubiquitin comprising a K11 lysine linkage, wherein the antibody does not specifically bind a second polyubiquitin comprising a second lysine linkage, wherein the second lysine linkage differs from a K11 lysine linkage. In another embodiment, the invention provides an isolated antibody that specifically binds both a first polyubiquitin comprising a K11 lysine linkage and a second polyubiquitin comprising a second lysine linkage, wherein the second lysine linkage differs from the K11 lysine linkage, wherein the antibody does not specifically bind monoubiquitin, and wherein the antibody binds the second polyubiquitin with a substantially reduced binding affinity as compared to the binding affinity of the antibody for the first polyubiquitin.

In another embodiment the invention provides an isolated antibody that specifically binds lysine-11-linked polyubiquitin, wherein the antibody does not specifically bind monoubiquitin. In one aspect, the antibody comprises at least one hypervariable (HVR) sequence selected from HVR-L1, HVR-L2, HVR-L3, HVR-H1, HVR-H2, and HVR-H3 of any of SEQ ID NOs: 2 and 57-60; SEQ ID NOs: 3 and 61; SEQ ID NO: 4; SEQ ID NOs: 6-11; SEQ ID NOs: 12-17 and 67; and SEQ ID NOs: 18-23, 68 and 69, respectively. In another aspect, the antibody comprises at least one sequence selected from HVR-H1, HVR-H2 and HVR-H3, wherein HVR-H1 comprises the amino acid sequence X1 X2 X3 X4 Ile X5 (SEQ ID NO: 24), wherein amino acid X1 is selected from serine and threonine, amino acid X2 is selected from asparagine, aspartic acid, serine and glycine, amino acid X3 is selected from tyrosine, serine and threonine, amino acid X4 is selected from tryptophan, aspartic acid, glycine and tyrosine, and amino acid X5 is selected from serine and histidine; wherein HVR-H2 comprises the amino acid sequence X6 X7 Ile X8 Pro X9 Gly X10 Thr X11 (SEQ ID NO: 25), wherein amino acid X6 is selected from glycine and alanine, amino acid X7 is selected from aspartic acid, tryptophan, glycine, glutamic acid and valine, amino acid X8 is selected from serine, tyrosine and asparagine, amino acid X9 is selected from aspartic acid, alanine, histidine and asparagine, amino acid X10 is selected from tyrosine and serine, and amino acid X11 is selected from tyrosine, aspartic acid and asparagine; and wherein HVR-H3 comprises the amino acid sequence X12 X13 X14 X15 X16 X17 X18 X19 X20 X21 Asp (SEQ ID NO: 26), wherein amino acid X12 is selected from arginine and lysine, amino acid X13 is selected from glutamic acid, glycine, aspartic acid and proline, amino acid X14 is selected from serine, isoleucine, valine and tryptophan, amino acid X15 is selected from tryptophan, glycine, tyrosine and phenylalanine, amino acid X16 is selected from tryptophan, tyrosine, leucine, glycine and phenylalanine, amino acid X17 is selected from serine, tyrosine, phenylalanine and glycine, amino acid X18 is selected from alanine, phenylalanine, tyrosine and glycine, or is not present, amino acid X19 is selected from tryptophan, glycine, alanine and tyrosine, or is not present, amino acid X20 is valine or is not present, and amino acid X21 is selected from methionine and phenylalanine.

In another aspect, the antibody comprises at least one sequence selected from HVR-L1, HVR-L2, wherein HVR-L1 comprises the amino acid sequence X22 X23 Ser X24 X25 X26 X27 X28 X29 X30 X31 (SEQ ID NO: 73), wherein amino acid X22 is selected from arginine and glycine, amino acid X23 is selected from alanine and valine, amino acid X24 is selected from glutamine and histidine, amino acid X25 is selected from aspartic acid, asparagine and isoleucine, amino acid X26 is selected from leucine and valine, amino acid X27 is selected from serine, aspartic acid, glycine and glutamic acid, amino acid X28 is selected from threonine and serine, amino acid X29 is selected from alanine, valine and phenylalanine, amino acid X30 is selected from valine and isoleucine, and amino acid X31 is selected from alanine and serine; and wherein HVR-L2 comprises the amino acid sequence X32 X33 X34 Phe X35 Tyr Ser (SEQ ID NO: 74), wherein amino acid X32 is selected from serine and asparagine, amino acid X33 is selected from glutamine and alanine, amino acid X34 is selected from glutamic acid and serine, and amino acid X35 is selected from leucine and valine.7. The antibody of claim 3, comprising at least one sequence selected from HVR-H2 and HVR-H3, wherein HVR-H2 comprises the amino acid sequence X36 Ile Asn Pro X37 Gly Gly Tyr Thr Tyr Tyr Ala Asp Ser Val Lys Gly (SEQ ID NO: 75), wherein amino acid X36 is selected from alanine and glycine and amino acid X37 is selected from alanine and asparagine; and wherein HVR-H3 comprises the amino acid sequence Glu Trp Tyr X38 X39 Gly Tyr Val Met Asp Tyr (SEQ ID NO: 76), wherein amino acid X38 is selected from phenylalanine and tyrosine and amino acid X39 is selected from glycine and aspartic acid.

In another aspect, the antibody comprises an HVR-L1 sequence of SEQ ID NO: 2, an HVR-L2 sequence of SEQ ID NO: 3, and an HVR-L3 sequence of SEQ ID NO: 4, respectively. In another aspect, the antibody comprises HVR-H1, HVR-H2, and HVR-H3 sequences corresponding to those set forth for clones A3, A6, A9, B5, F5 or G3 in FIG. 1B. In another aspect, the antibody comprises HVR-L1, HVR-L2, and HVR-L3 sequences corresponding to those set forth for clones 1A11, 1C12, 1F12, 2A3, 2A6, 2D7, 2E6 or 2G4 in FIG. 4A. In another aspect, the antibody comprises HVR-H1, HVR-H2, and HVR-H3 sequences corresponding to those set forth for clones 1A11, 1C12, 1F12, 2A3, 2A6, 2E6 or 2G4 in FIG. 4B.

In another aspect, the antibody comprises the HVR-L1 sequence of SEQ ID NO: 2, the HVR-L2 sequence of SEQ ID NO: 3, the HVR-L3 sequence of SEQ ID NO: 4, the HVR-H1 sequence of SEQ ID NO: 11, the HVR-H2 sequence of SEQ ID NO: 17 and the HVR-H3 sequence of SEQ ID NO: 23. In another aspect, the antibody comprises the HVR-L1 sequence of SEQ ID NO: 58, the HVR-L2 sequence of SEQ ID NO: 3, the HVR-L3 sequence of SEQ ID NO: 4, the HVR-H1 sequence of SEQ ID NO: 11, the HVR-H2 sequence of SEQ ID NO: 17 and the HVR-H3 sequence of SEQ ID NO: 23. In another aspect, the antibody comprises the HVR-L1 sequence of SEQ ID NO: 59, the HVR-L2 sequence of SEQ ID NO: 3, the HVR-L3 sequence of SEQ ID NO: 4, the HVR-H1 sequence of SEQ ID NO: 11, the HVR-H2 sequence of SEQ ID NO: 17 and the HVR-H3 sequence of SEQ ID NO: 23. In another aspect, the antibody comprises the HVR-L1 sequence of SEQ ID NO: 2, the HVR-L2 sequence of SEQ ID NO: 3, the HVR-L3 sequence of SEQ ID NO: 4, the HVR-H1 sequence of SEQ ID NO: 11, the HVR-H2 sequence of SEQ ID NO: 67 and the HVR-H3 sequence of SEQ ID NO: 23. In another aspect, the antibody comprises the HVR-L1 sequence of SEQ ID NO: 58, the HVR-L2 sequence of SEQ ID NO: 3, the HVR-L3 sequence of SEQ ID NO: 4, the HVR-H1 sequence of SEQ ID NO: 11, the HVR-H2 sequence of SEQ ID NO: 67 and the HVR-H3 sequence of SEQ ID NO: 23. In another aspect, the antibody comprises the HVR-L1 sequence of SEQ ID NO: 59, the HVR-L2 sequence of SEQ ID NO: 3, the HVR-L3 sequence of SEQ ID NO: 4, the HVR-H1 sequence of SEQ ID NO: 11, the HVR-H2 sequence of SEQ ID NO: 67, and the HVR-L3 sequence of SEQ ID NO: 23.

In another aspect, the antibody comprises a light chain amino acid sequence selected from SEQ ID NOs: 5 and 62-66. In another aspect, the antibody comprises a heavy chain amino acid sequence selected from SEQ ID NOs: 27-32 and 70-72.

In another aspect, the antibody comprises light chain and heavy chain amino acid sequences with at least 95% sequence identity to the amino acid sequences of one of the following combinations of sequences: SEQ ID NOs 5 and 32; SEQ ID NOs: 63 and 32; SEQ ID NOs: 65 and 32; SEQ ID NOs: 5 and 72; SEQ ID NOs: 63 and 72; and SEQ ID NOs: 65 and 72.

In another embodiment, the invention provides an isolated antibody, wherein the antibody binds to the same antigenic determinant on K11-linked polyubiquitin as any one of the foregoing antibodies, and wherein the antibody does not specifically bind to monoubiquitin. In another embodiment, the invention provides an isolated antibody that competes with any one of the foregoing antibodies for binding to polyubiquitin, wherein the antibody does not specifically bind to monoubiquitin. In another embodiment, the invention provides any of the foregoing isolated antibodies, wherein the antibody specifically binds to a K11-linked polyubiquitinated protein. In another embodiment, the invention provides any of the foregoing isolated antibodies, wherein the antibody modulates at least one polyubiquitin-mediated signaling pathway.

In one general aspect, any of the foregoing antibodies is a monoclonal antibody. In another general aspect, any of the foregoing antibodies is a human antibody. In another general aspect, any of the foregoing antibodies is a humanized antibody. In another general aspect, any of the foregoing antibodies is a chimeric antibody. In another general aspect, any of the foregoing antibodies is an antibody fragment that binds K11-linked polyubiquitin.

In another embodiment, the invention provides an isolated nucleic acid encoding any of the foregoing antibodies. In another embodiment, the invention provides a vector comprising an isolated nucleic acid encoding any of the foregoing antibodies. In another embodiment, the invention provides a host cell comprising an isolated nucleic acid encoding any of the foregoing antibodies. In another embodiment, the invention provides a host cell comprising a vector comprising an isolated nucleic acid encoding any of the foregoing antibodies.

In another embodiment, the invention provides a method of producing any of the foregoing antibodies, comprising culturing the above-recited host cell under conditions wherein the antibody is produced. In one aspect, the method further comprises recovering the antibody from the host cell. In another aspect, the method further comprises purification of the antibody.

In another embodiment, the invention provides an immunoconjugate comprising any of the foregoing antibodies and a cytotoxic agent. In another embodiment, the invention provides a pharmaceutical formulation comprising any of the foregoing antibodies and a pharmaceutically acceptable carrier. In one aspect, the pharmaceutical formulation further comprises an additional therapeutic agent. In one such aspect, the additional therapeutic agent is a chemotherapeutic agent.

In another embodiment, the invention provides any of the foregoing antibodies for use as a medicament. In another embodiment, the invention provides any of the foregoing antibodies for use in treating a cell-cycle-related disease or disorder. In one aspect, the cell-cycle-related disease or disorder is selected from a disease or disorder associated with aberrantly increased cell cycle progression and a disease or disorder associated with aberrantly decreased cell cycle progression. In one such aspect, the disease or disorder associated with aberrantly increased cell cycle progression is cancer. In another such aspect, the disease or disorder associated with aberrantly decreased cell cycle progression is selected from a degenerative muscle disorder and a degenerative nerve disorder.

In another embodiment, the invention provides the use of any of the foregoing antibodies in the manufacture of a medicament. In one aspect, the medicament is for a disease or disorder selected from cancer, a degenerative muscle disorder, and a degenerative nerve disorder. In another embodiment, the invention provides a method of treating an individual having a disease or disorder selected from cancer, a degenerative muscle disorder, and a degenerative nerve disorder, comprising administering to the individual an effective amount of any of the foregoing antibodies.

In another embodiment, the invention provides a method of determining the presence of a polyubiquitin or polyubiquitinated protein in a sample suspected of containing a polyubiquitin or polyubiquitinated protein, comprising exposing the same to at least one of the foregoing antibodies and determining the binding of the at least one antibody to a polyubiquitin or polyubiquitinated protein in the sample. In another embodiment, the invention provides a method of separating K11-linked polyubiquitinated protein from non-K11-linked polyubiquitinated protein in a sample, comprising contacting the sample with at least one of the foregoing antibodies. In another embodiment, the invention provides a method of determining the function and/or activity of K11-linked polyubiquitin in a cell or sample comprising contacting the cell or sample with at least one of the foregoing antibodies and assessing the effect of said contacting step on the cell or sample.

BRIEF DESCRIPTION OF THE FIGURES

FIG. 1A depicts the light chain sequence of clones isolated from the naïve sort of the VH library. Due to the library design, the sequences of the light chains were identical for all obtained clones. FIG. 1B depicts the heavy chain sequence alignment of the clones isolated from the naïve VH library sort. The numbers of sibling clones identified from both the third and fourth round of sorting are indicated for each clone. In both FIGS. 1A and 1B, the HVR sequences for each clone are indicated by the boxed regions, with the first box indicating HVR-L1 (FIG. 1A) or HVR-H1 (FIG. 1B), the second box indicating HVR-L2 (FIG. 1A) or HVR-H2 (FIG. 1B), and the third box indicating HVR-L3 (FIG. 1A) or HVR-H3 (FIG. 1B).

FIGS. 3A-3C depict the binding properties of the purified G3 Fab, as described in Example 1. FIG. 3A shows the results of experiments assessing the ability of different concentrations of purified G3 Fab to bind to a panel of ubiquitin proteins in an ELISA. FIG. 3B depicts the results of an IC50 competition ELISA to measure the affinity of the purified G3 Fab for K11-linked diubiquitin. FIG. 3C shows the results of a western blot analysis to determine the ability of the G3 Fab to specifically recognize a panel of ubiquitin proteins in an immobilized context. The coomassie stained gel demonstrates the mobility of each sample.

FIG. 4A depicts the light chain sequences of the affinity matured clones. FIG. 4B depicts the heavy chain sequence alignment of the affinity matured clones. The numbers of sibling clones identified from the fourth round of sorting are indicated for each clone. In both FIGS. 4A and 4B, the HVR sequences for each clone are indicated by the boxed regions, with the first box indicating HVR-L1 (FIG. 4A) or HVR-H1 (FIG. 4B), the second box indicating HVR-L2 (FIG. 4A) or HVR-H2 (FIG. 4B), and the third box indicating HVR-L3 (FIG. 4A) or HVR-H3 (FIG. 4B). Amino acid changes relative to the G3 parental sequence are highlighted in grey.

FIG. 6A depicts the light chain sequences of the hybrid clones. FIG. 6B depicts the heavy chain sequence alignment of the hybrid clones. In both FIGS. 6A and 6B, the HVR sequences for each clone are indicated by the boxed regions, with the first box indicating HVR-L1 (FIG. 6A) or HVR-H1 (FIG. 6B), the second box indicating HVR-L2 (FIG. 6A) or HVR-H2 (FIG. 6B), and the third box indicating HVR-L3 (FIG. 6A) or HVR-H3 (FIG. 6B). Amino acid changes relative to the G3 parental sequence are highlighted in grey.

FIG. 7A provides ELISA results showing the binding of G3, 1C12/2E6, and 2A3/2E6 IgGs in 4M urea to a panel of ubiquitin proteins. FIG. 7B provides western blot analyses of binding of G3, 1C12/2E6, or 2A3/2E6 IgGs to two-fold serial dilutions of K11-linked diubiquitin (1000, 500, 250, 125, 63, 31, and 16 ng/lane where gradient is indicated) or monoubiquitin, linear diubiquitin, K48-linked diubiquitin, and K63-linked diubiquitin (1 µg/lane). The Coomassie stained gel (upper left panel) provides an indication of where each of the tested ubiquitins migrates in the gels. FIG. 7C depicts the results of experiments in which monoubiquitin, K48-linked polyubiquitin 2-7 (two to seven ubiquitin subunits in length), K63-linked polyubiquitin 2-7 (two to seven ubiquitin subunits in length), and K11-linked polyubiquitin (1 µg each per lane) were immunoblotted with a pan-ubiquitin antibody P4D1 (middle panel) or the 2A3/2E6 IgG (right panel). Coomassie staining revealed the composition of the samples (left panel). FIG. 7D depicts the results of experiments in which K11-linked diubiquitin (50 ng/lane), K48-linked diubiquitin (1 µg/lane), K63-linked diubiquitin (1 µg/lane), whole cell lysate from human 293T cells (100 µg/lane) and *S. cerevisiae* were immunoblotted with the 2A3/2E6 IgG (right panel). Coomassie staining revealed the composition of the samples (left panel).

FIG. 8A provides a western blot performed with pan-ubiquitin antibody P4D1 following the autoubiquitination of MuRF1. Addition of E1 (Ube1), E2 (UbcH5c), and E3 (MuRF1) enzymes resulted in conversion of monoubiquitin to polyubiquitin chains on MuRF1 (MuRF1-Ub$_{(n)}$). FIG. 8B shows the results of an immunoprecipitation assay in which an MuRF1 autoubiquitination assay performed with wild-type ubiquitin was used as a substrate for immunoprecipitation by the 2A3/2E6 IgG in the presence of varying concentrations of urea. The input reaction as well as the immunoprecipitated material was detected by western blot with a pan-ubiquitin antibody (P4D1). FIG. 8C shows the immunoblot results of an experiment performed identically to that depicted in FIG. 8B, except that K11R ubiquitin was used instead of wild-type ubiquitin. FIG. 8D shows western blots resulting from MuRF1 autoubiquitination reactions performed in vitro using WT, K11R, K48R, and K63R ubiquitin that were immunoprecipitated with either the 2A3/2E6 antibody (K11) or an isotype control antibody, and subjected to western analysis. Numbers in parentheses indicate the relevant lanes on the gel and columns in (E). Autoubiquitination reactions (inputs in lanes 1, 4, 7, and 10) and immunoprecipitations (lanes 2, 3, 5, 6, 8, 9, 11, and 12) were immunoblotted with a pan-ubiquitin antibody. White lines indicate the region of the coomassie-stained gel excised for mass spectrometry AQUA analysis, as guided by the western blot. FIG. 8E shows the results of the mass spectrometry AQUA analyses on the regions of the gel indicated in FIG. 8D. The amount of K11, K48, and K63 linkages measured in each sample is indicated. In each case negligible amounts of ubiquitin linkages were detected in the immunoprecipitations using the isotype control antibody.

FIGS. 9A-9D show the results of experiments testing the ability of hybrid antibody 2A3/2E6 to specifically recognize and/or immunoprecipitate K11-linked polyubiquitinated proteins from cellular lysates. FIG. 9A shows the experimental design and the western blot results of immunoprecipitations performed on cell lysates from HEK293T cells mock transfected or with a plasmid over-expressing WT or K0 ubiquitin, immunoprecipitated with either the 2A3/2E6 antibody (K11) or an isotype control antibody. Numbers in parentheses indicate the relevant lanes on the gel and in the columns in FIG. 9B. Whole cell lysates (inputs, lanes 1, 4, and 7) and immunoprecipitations (lanes 2, 3, 5, 6, 8, and 9) were immunoblotted with a pan-ubiquitin antibody. White lines indicate the regions of the coomassie-stained gel excised for mass spectrometry AQUA analysis, as guided by the western blot. FIG. 9B shows the Coomassie-stained equivalent gels of the western blot shown in FIG. 9A. Regions A and B of the coomassie-stained gel were excised for the inputs and immunoprecipitations. The numbering corresponds to that in FIG. 9A. FIG. 9C shows the results of mass spectrometric analyses performed on the regions of the gel indicated in FIGS. 9A and 9B. The amount of K11, K48, and K63 linkages measured in each sample is indicated. In each case negligible amounts of ubiquitin linkages were detected in the immunoprecipitations using an isotype control antibody. FIG. 9D provides graphs comparing the percentage of K11-linkages amongst total ubiquitin linkages measured in the inputs and immunoprecipitations (anti-K11), demonstrating enrichment of K11 linkages by the hybrid anti-K11 linkage-specific antibody.

DETAILED DESCRIPTION OF EMBODIMENTS OF THE INVENTION

I. Definitions

Figure 1A:
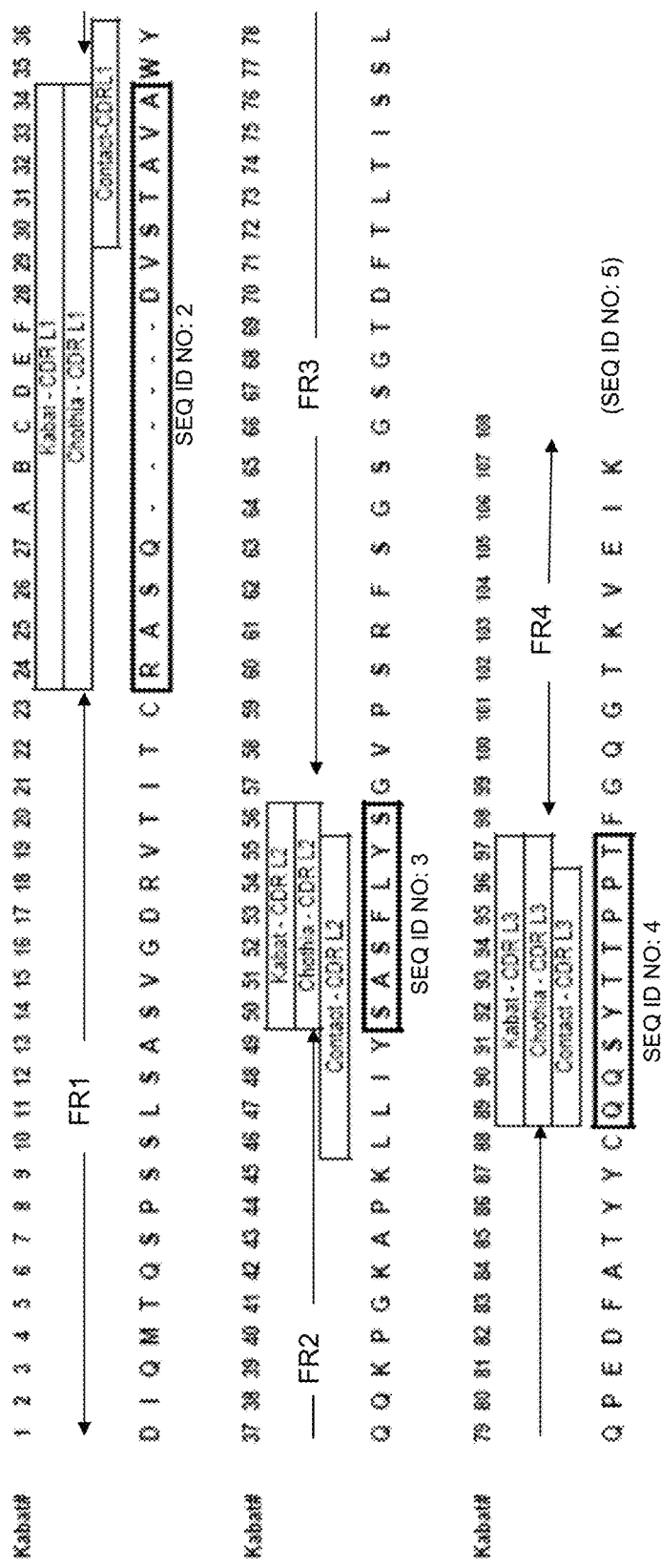
FIGS. 1A and 1B depict the light and heavy chain amino acid sequences of the Fabs obtained in Example 1.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "agonist antibody" as used herein is an antibody which mimics at least one of the functional activities of a polypeptide of interest.

An "antagonist antibody" or a "blocking antibody" is an antibody which inhibits or reduces biological activity of the antigen to which it specifically binds. Certain blocking antibodies or antagonist antibodies substantially or completely inhibit the biological activity of the antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "anti-K11-linked polyubiquitin antibody" and "an antibody that binds to K11-linked polyubiquitin" refer to an antibody that is capable of binding K11-linked polyubiquitin with sufficient affinity such that the antibody is useful as a diagnostic and/or therapeutic agent in targeting K11-linked polyubiquitin. In one embodiment, the extent of binding of an anti-K11-linked polyubiquitin antibody to an unrelated, non-K11-linked polyubiquitin protein is less than about 10% of the binding of the antibody to K11-linked polyubiquitin as measured, e.g., by a radioimmunoassay (RIA). In certain embodiments, an antibody that binds to K11-linked polyubiquitin has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-K11-linked polyubiquitin antibody binds to an epitope of K11-linked polyubiquitin that is conserved among K11-linked polyubiquitin from different species.

As used herein, the term "anti-polyubiquitin antibody" refers to an antibody that is capable of specifically binding to a polyubiquitin molecule.

As used herein, the terms "anti-ubiquitin antibody" and "anti-monoubiquitin antibody" are used interchangeably, and refer to an antibody that is capable of specifically binding to a ubiquitin molecule.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer, and hypotrophy disorders including, but not limited to, degenerative muscle disorders and degenerative nerve disorders.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-K11-linked polyubiquitin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

As used herein, the terms "K*-linked polyubiquitin" and "Lys*-linked polyubiquitin" are interchangeable, and refer to a polyubiquitin molecule comprising at least one isopeptide bond between the C-terminus of one ubiquitin moiety and a lysine at position * in another ubiquitin moiety. For example, a "K11-linked polyubiquitin" is used interchangeably with a "Lys11-linked polyubiquitin", and both terms refer to a polyubiquitin molecule comprising an isopeptide bond between the C-terminus of one of the ubiquitin moieties in the molecule and the lysine at position 11 in another ubiquitin moiety in the molecule.

As used herein, a statement that a first lysine linkage "differs" from a second lysine linkage indicates that the first lysine linkage between one ubiquitin moiety and another ubiquitin moiety involves a different lysine residue (e.g., K6, K11, K27, K29, K33, K48, and/or K63) than the second lysine linkage between one ubiquitin moiety and another ubiquitin moiety.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "polyubiquitin" is defined as all species of native human and synthetic polymeric chains of ubiquitin which fall within human and synthetic classes of different polymeric linkages of ubiquitin, including, but not limited to, K6-linked polyubiquitin, K11-linked polyubiquitin, K27-linked polyubiquitin, K29-linked polyubiquitin, K33-linked polyubiquitin, K48-linked polyubiquitin and K63-linked polyubiquitin. Polyubiquitin may be of any length, and includes at least two ubiquitin moieties. Polyubiquitin is distinguished from tandem repeats of ubiquitin that are originally expressed as a single protein.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, the terms "ubiquitin" and "monoubiquitin" are used interchangeably, and refer to any native ubiquitin from any vertebrate source, including mammals such as primates (e.g. humans) and rodents (e.g., mice and rats), unless otherwise indicated. The term encompasses "full-length," unprocessed ubiquitin as well as any shortened or posttranslationally modified form of ubiquitin that results from processing in the cell, excepting molecules comprised of multiple ubiquitin moieties. The term also encompasses naturally occurring variants of ubiquitin, e.g., splice variants or allelic variants. The amino acid sequence of an exemplary human ubiquitin is shown in SEQ ID NO:1: MQIFVKTLTGKTITLEVEPSDTIENVKAKIQDKEGIPP-DQQRLIFA GKQLEDGRTLSDYNIQKESTLHLVLRL-RGG (SEQ ID NO: 1). Ubiquitin has at least one lysine residue at amino acid 6, amino acid 11, amino acid 27, amino acid 29, amino acid 33, amino acid 48, and/or amino acid 63 (marked in bold in SEQ ID NO: 1, above).

As used herein, the term "ubiquitin pathway" refers to a biochemical pathway in a cell or reconstituted in vitro that includes ubiquitin and/or polyubiquitin.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on the creation of antibodies that are capable of specifically recognizing a first polyubiquitin molecule containing a first polyubiquitin linkage but not specifically binding to a second polyubiquitin molecule containing a second polyubiquitin linkage. In certain embodiments, antibodies that specifically bind to K11-linked polyubiquitin are provided. Antibodies of the invention are useful both in research and, e.g., for the diagnosis or treatment, e.g., of diseases and disorders relating to aberrant cell cycle progression.

The unique properties of the anti-K11-linked polyubiquitin antibodies of the invention make them particularly useful for distinguishing between different lysine-linked forms of polyubiquitin in a cellular system without resorting to cumbersome and expensive genetic manipulation or biophysical methods such as mass spectrometry. The anti-K11-linked polyubiquitin antibodies of the invention can be used to characterize the function(s) and activities of specific K11-linked polyubiquitins both in vitro and in vivo. The anti-K11-linked polyubiquitin antibodies of the invention can also be used to determine the role of specific K11-linked polyubiquitins in the development and pathogenesis of disease. The anti-K11-linked polyubiquitin antibodies of the invention can further be used to treat diseases in which one or more specific lysine-linked polyubiquitins are aberrantly regulated or aberrantly functioning without interfering with the normal activity of polyubiquitins for which the anti-polyubiquitin antibodies are not specific.

The anaphase-promoting complex, APC/C, is known to act as the ubiquitinating E3 ligase responsible for the majority of the K11-linked polyubiquitin chains synthesized during mitosis. In particular, APC/C-mediated K11-linked polyubiquitination of mitotic proteins such as cyclins, geminin, and Plk1 results in subsequent degradation of those labeled proteins by the proteasome. When endogenous ubiquitin is mutated such that the lysine at position 11 is changed to an arginine and therefore cannot be used for the lysine linkage, the resulting mutant cells demonstrate an aberrant lack of degradation of important mitotic proteins and cell cycle arrest. In *Xenopus*, this mutation results in death of the embryo prior to gastrulation. The presence and accessibility of the K11-linked polyubiquitin label thus plays an important role in normal cell cycle progression, and the antibodies and Fabs of the invention provide a useful therapeutic means for modulation of disorders and disease states in which cell cycle regulation is aberrant. In one embodiment, the anti-K11-linked polyubiquitin antibodies of the invention are used to treat diseases and disorders where cell cycle progression is aberrantly upregulated, resulting in too much cell division, such as cancer. In another embodiment, the anti-K11-linked polyubiquitin antibodies of the invention are used to treat diseases and disorders where cell cycle progression is aberrantly downregulated, resulting in too little cell division and concomitant wasting or destruction of tissue. Examples of such diseases include, but are not limited to, degenerative muscle disorders and degenerative nerve disorders (including, but not limited to, Charcot Marie Tooth syndrome, poliomyelitis, amyotrophic lateral sclerosis, and Guillain-Barre syndrome).

As used herein, the terms "cell proliferative disorder" and "proliferative disorder" refer to disorders that are associated with some degree of abnormal cell proliferation. In one embodiment, the cell proliferative disorder is cancer.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, appendiceal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "tumor" as used herein refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "degenerative muscle disorder" refers to or describes the physiological condition in muscle-containing animals that is typically characterized by deterioration or weakening of skeletal and/or smooth muscle such that normal muscular function is reduced. Examples of degenerative muscular disorders include, but are not limited to, muscular dystrophy, myotonic dystrophy, myotonia congenita, cachexia, sarcopenia, multiple sclerosis, amyotrophic lateral sclerosis, Isaac's syndrome, stiff-person syndrome, familiar periodic paralyses, myopathy, myotonia, rhabdomyolyses, muscle atrophy, and various types of muscle weakness and muscle rigidity.

The term "degenerative nerve disorder" refers to or describes the physiological condition in nerve-containing animals that is typically characterized by deterioration of nervous tissue or deterioration of communication between cells in nervous tissue. Examples of degenerative nerve disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, amyotrophic lateral sclerosis, Guillian-Barre syndrome, Carcot Marie Tooth syndrome, striatonigral degeneration, and nervous cell/tissue destruction caused by or associated with tauopathies, prion diseases, bulbar palsy, motor neuron disease, dementia, and nervous system heterodegenerative disorders (including, but not limited to, Canavan disease, Huntington's disease, neuronal ceroidlipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome).

In another aspect, the anti-K11-linked polyubiquitin antibodies of the invention find utility as reagents for detection and isolation of K11-linked polyubiquitin, such as detection of polyubiquitin in various cell types and tissues, including the determination of polyubiquitin density and distribution in cell populations and within a given cell, and cell sorting based on the presence or amount of polyubiquitin. In yet another aspect, the present anti-K11-linked polyubiquitin antibodies are useful for the development of polyubiquitin antagonists with blocking activity patterns similar to those of the subject antibodies of the invention. As a further example, anti-K11-linked polyubiquitin antibodies of the invention can be used to identify other anti-polyubiquitin antibodies that bind substantially the same antigenic determinant(s) of polyubiquitin as the antibodies exemplified herein, including linear and conformational epitopes.

The anti-K11-linked polyubiquitin antibodies of the invention can be used in assays based on the physiological pathways in which polyubiquitin is involved to screen for small molecule antagonists of K11-linked polyubiquitin function. For example, since K11-linked polyubiquitin chains are known to be necessary for normal cell cycle progression through anaphase, (CITE), the activity of anti-K11-linked polyubiquitin antibodies to modulate (up- or down-regulate) cell cycle progression in treated cells or tissues may be compared to the activity of one or more potential small molecule antagonists of K11-linked polyubiquitin in modulating cell cycle progression.

A. Exemplary Anti-K11-Linked Polyubiquitin Antibodies

In one aspect, the invention provides isolated antibodies that bind to K11-linked polyubiquitin. In certain embodiments, an anti-K11-linked polyubiquitin antibody specifically binds to K11-linked polyubiquitin but does not specifically bind to monoubiquitin. In certain embodiments, an anti-K11-linked polyubiquitin antibody specifically binds to K11-linked polyubiquitin but does not specifically bind to polyubiquitin having any other lysine linkage (i.e., K6-, K27-, K29-, K33-, K48-, and/or K63-linkages).

In one aspect, the invention provides an anti-K11-linked polyubiquitin antibody comprising an HVR-H1 region comprising the sequence of at least one of SEQ ID NOs: 6-11 and 24. In one aspect, the invention provides an antibody comprising an HVR-H2 region comprising the sequence of at least one of SEQ ID NOs: 12-17, 25, 67, and 75. In one aspect, the invention provides an antibody comprising an HVR-H3 region comprising the sequence of at least one of SEQ ID NOs: 18-23, 26, 68, 69, and 76.

In one aspect, the invention provides an antibody comprising an HVR-H1 region comprising the sequence of at least one of SEQ ID NOs: 6-11 and 24, and an HVR-H2 region comprising the sequence of at least one of SEQ ID NOs: 12-17, 25, 67, and 75. In one aspect, the invention provides an antibody comprising an HVR-H1 region comprising the sequence of at least one of SEQ ID NOs: 6-11 and 24, and an HVR-H3 region comprising the sequence of at least one of SEQ ID NOs: 18-23, 26, 68, 69, and 76. In one aspect, the invention provides an antibody comprising an HVR-H2 region comprising the sequence of at least one of SEQ ID NOs: 12-17, 25, 67, and 75 and an HVR-H3 region comprising the sequence of at least one of SEQ ID NOs: 18-23, 26, 68, 69, and 76.

In one aspect, the invention provides an antibody comprising an HVR-L1 region comprising the sequence of at least one of SEQ ID NOs: 2, 57-60 and 73. In one aspect, the invention provides an antibody comprising an HVR-L2 region comprising the sequence of at least one of SEQ ID NOs: 3, 61, and 74. In one aspect, the invention provides an antibody comprising an HVR-L3 region comprising the sequence of SEQ ID NO: 4.

In one aspect, the invention provides an antibody comprising an HVR-L1 region comprising the sequence of at least one of SEQ ID NOs: 2, 57-60 and 73 and an HVR-L2 region comprising the sequence of at least one of SEQ ID NOs: 3, 61, and 74. In one aspect, the invention provides an antibody comprising an HVR-L1 region comprising the sequence of at least one of SEQ ID NOs: 2, 57-60 and 73 and an HVR-L3 sequence of SEQ ID NO: 4. In one aspect, the invention provides an antibody comprising an HVR-L2 region comprising the sequence of at least one of SEQ ID NOs: 3, 61, and 74 and an HVR-L3 sequence of SEQ ID NO: 4.

In one aspect, the invention provides an antibody comprising at least one, at least two, at least three, at least four, at least five or all six of the following:

(i) an HVR-H1 sequence comprising at least one sequence of SEQ ID NOs: 6-11 and 24;
(ii) an HVR-H2 sequence comprising at least one sequence of SEQ ID NOs: 12-17, 25, 67, and 75;
(iii) an HVR-H3 sequence comprising at least one sequence of SEQ ID NOs: 18-23, 26, 68, 69, and 76;
(iv) an HVR-L1 sequence comprising at least one sequence of SEQ ID NOs: 2, 57-60 and 73;
(v) an HVR-L2 sequence comprising at least one sequence of SEQ ID NOs: 3, 61, and 74; and
(vi) an HVR-L3 sequence of SEQ ID NO: 4.

In one aspect, the invention provides an antibody that specifically binds K11-linked polyubiquitin with high affinity but binds polyubiquitin some other lysine linkage with substantially reduced affinity, comprising at least one, at least two, at least three, at least four, at least five or all six of the following:

(i) an HVR-H1 sequence comprising at least one sequence of SEQ ID NOs: 6-11 and 24;
(ii) an HVR-H2 sequence comprising at least one sequence of SEQ ID NOs: 12-17, 25, 67, and 75;
(iii) an HVR-H3 sequence comprising at least one sequence of SEQ ID NOs: 18-23, 26, 68, 69, and 76;
(iv) an HVR-L1 sequence comprising at least one sequence of SEQ ID NOs: 2, 57-60 and 73;
(v) an HVR-L2 sequence comprising at least one sequence of SEQ ID NOs: 3, 61, and 74; and
(vi) an HVR-L3 sequence of SEQ ID NO: 4.

Figure 1B:
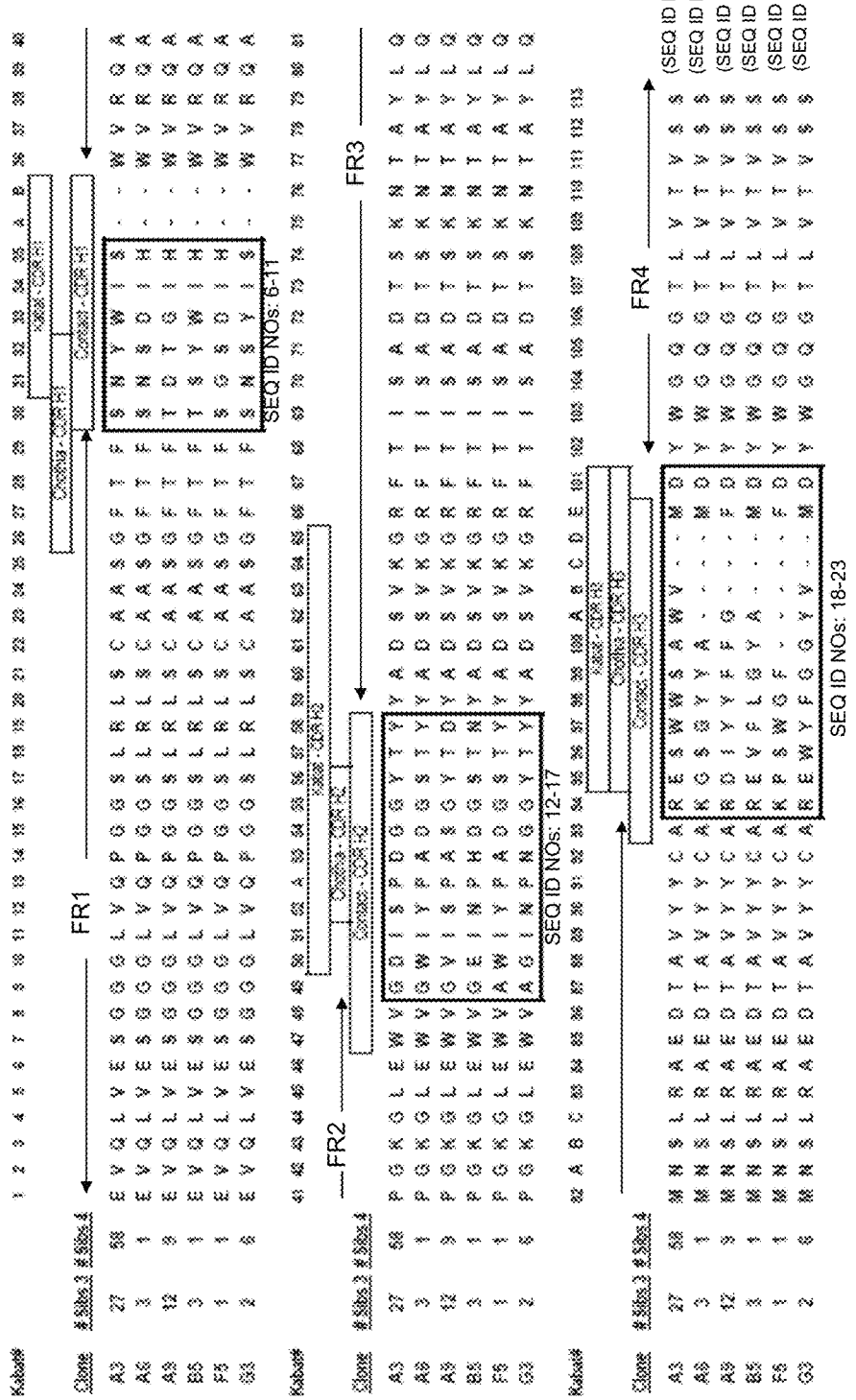
Figure 4A:
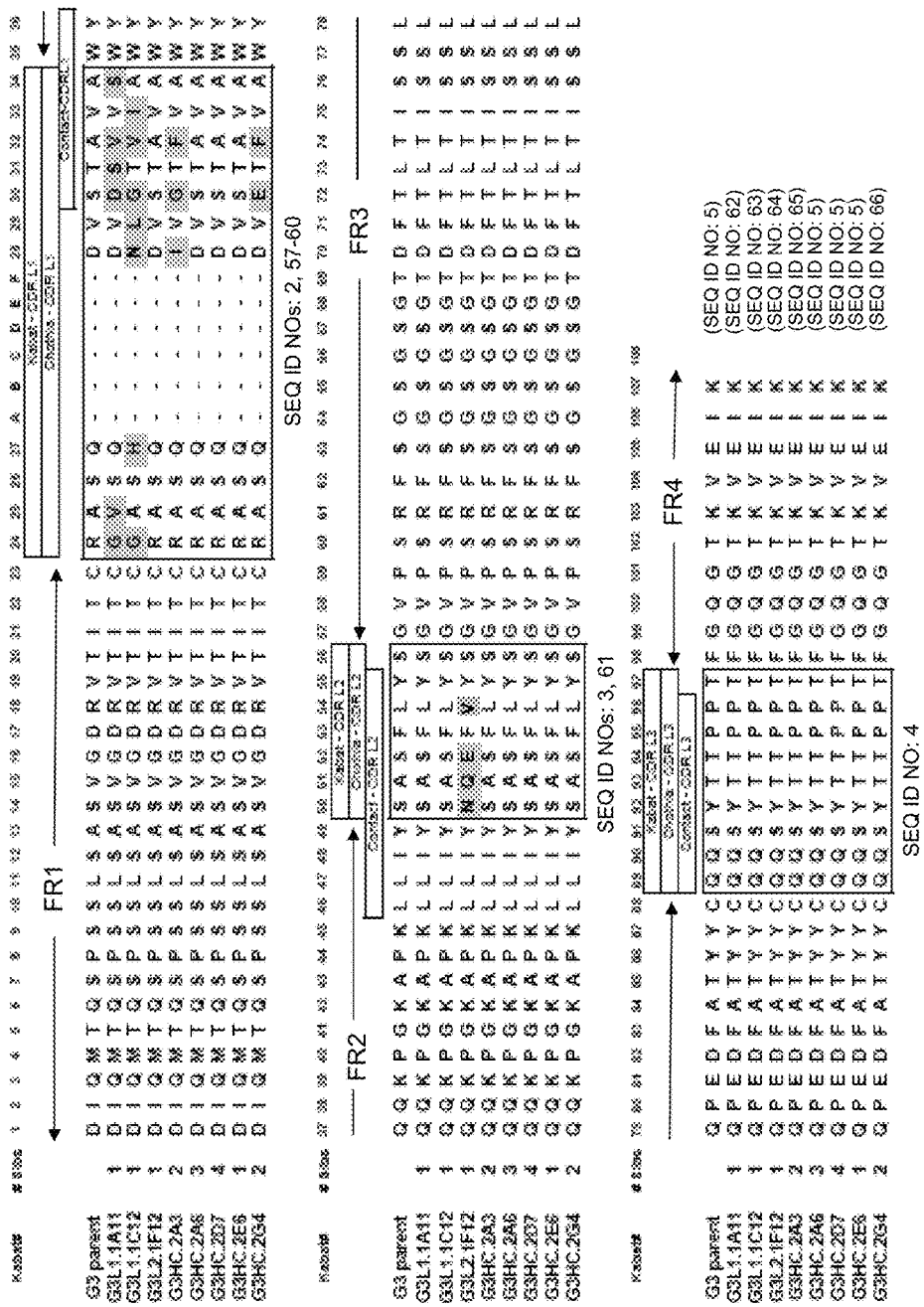
FIGS. 4A and 4B depict the light and heavy chain amino acid sequences of the affinity matured clones obtained in Example 2.
Figure 4B:
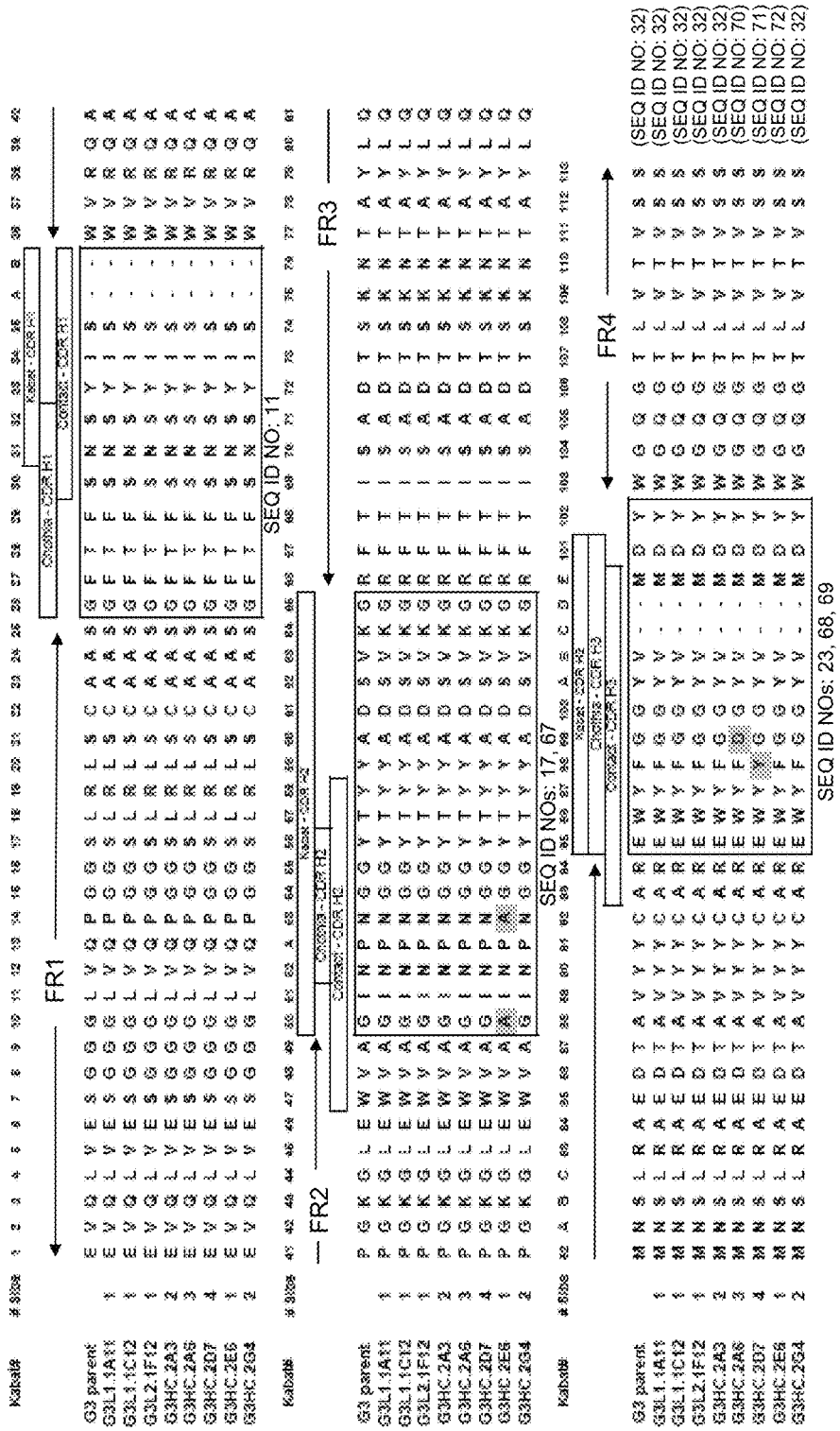
Figure 6A:
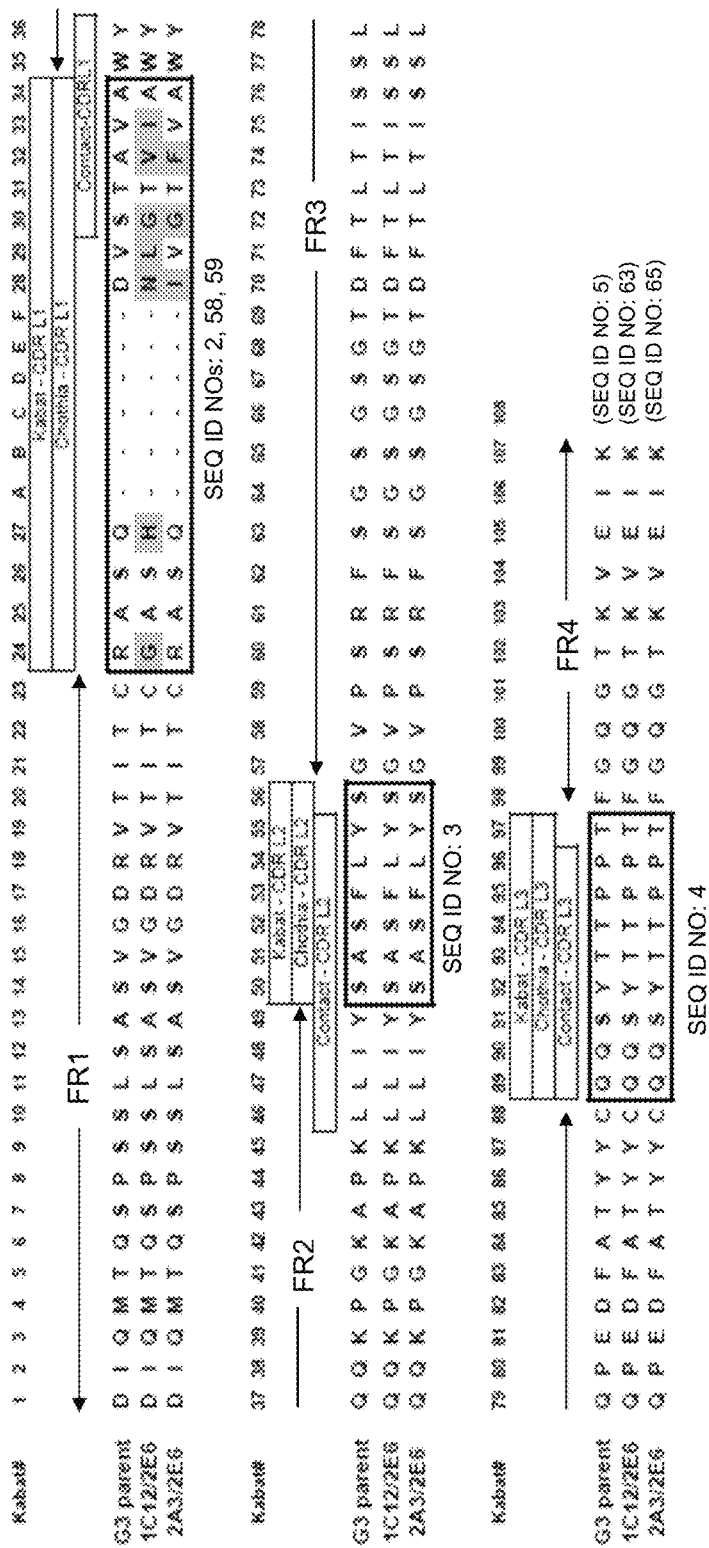
FIGS. 6A and 6B depict the light and heavy chain amino acid sequences of the hybrid clones obtained in Example 2.
Figure 6B:
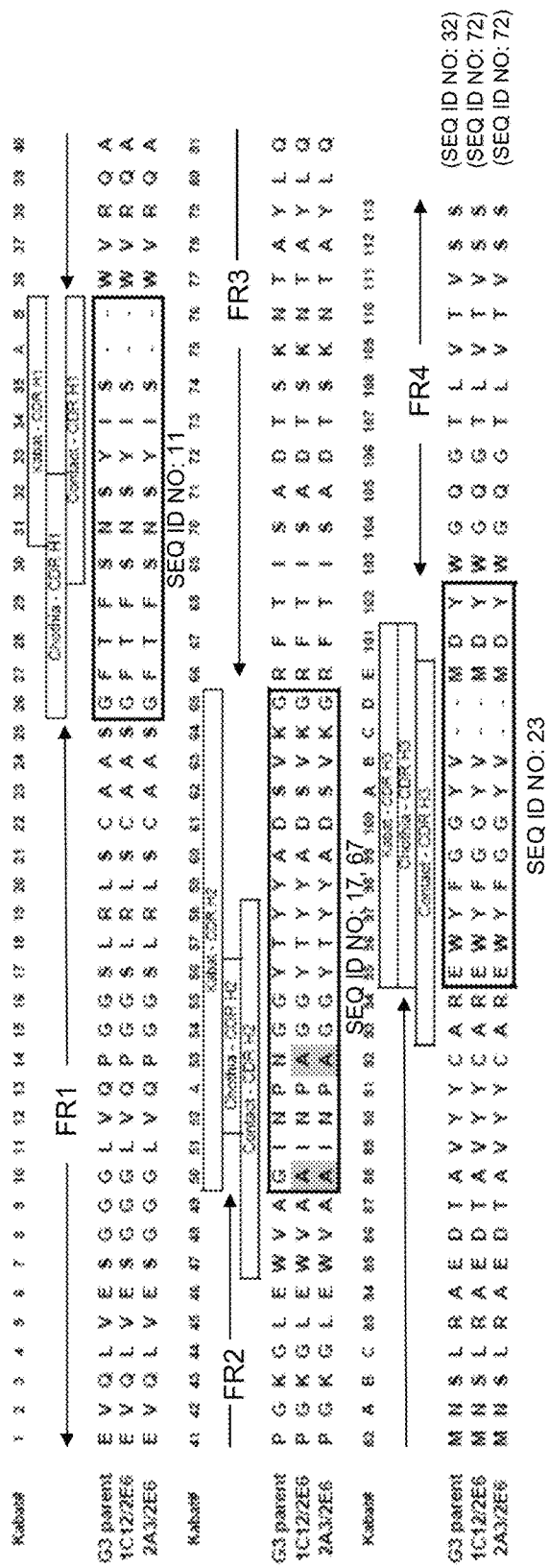

In one aspect, the invention provides antibodies comprising heavy chain HVR sequences as depicted in FIG. 1B, 4B, or 6B. In one embodiment, the antibodies comprise light chain HVR sequences as depicted in FIG. 1A, 4A, or 6A. In one embodiment, the antibodies comprise heavy chain HVR sequences as depicted in FIG. 1B, 4B or 6B and light chain HVR sequences as depicted in FIG. 1A, 4A, or 6A.

Some embodiments of antibodies of the invention comprise a light chain variable domain of humanized 4D5 antibody (huMAb4D5-8) (HERCEPTIN®, Genentech, Inc., South San Francisco, Calif., USA) (also referred to in U.S. Pat. No. 6,407,213 and Lee et al., J. Mol. Biol. (2004), 340(5):1073-93) as depicted in SEQ ID NO: 79 below.

```
                                          (SEQ ID NO: 79)
1 Asp Ile Gln Met Thr Gln Ser Pro Ser Ser Leu Ser

Ala Ser Val Gly Asp Arg Val Thr Ile Thr Cys Arg

Ala Ser Gln Asp Val Asn Thr Ala Val Ala Trp Tyr

Gln Gln Lys Pro Gly Lys Ala Pro Lys Leu Leu Ile

Tyr Ser Ala Ser Phe Leu Tyr Ser Gly Val Pro Ser

Arg Phe Ser Gly Ser Arg Ser Gly Thr Asp Phe Thr

Leu Thr Ile Ser Ser Leu Gln Pro Glu Asp Phe Ala

Thr Tyr Tyr Cys Gln Gln His Tyr Thr Thr Pro Pro

Thr Phe Gly Gln Gly Thr Lys Val Glu Ile Lys 107
(HVR residues are underlined)
```

In one embodiment, the huMAb4D5-8 light chain variable domain sequence is modified at one or more of positions 28, 30, 31, 53, 66, and 91 (Asp, Asn, Thr, Phe, Arg, and His as indicated in bold/italics above, respectively). In one embodiment, the modified huMAb4D5-8 sequence comprises Ser in position 28, Ser in position 30, Ser in position 31, Ser in position 53, Gly in position 66, and/or Ser in position 91. Accordingly, in one embodiment, an antibody of the invention comprises a light chain variable domain comprising the sequence depicted in SEQ ID NO: 80 below:

```
                                              (SEQ ID NO: 80)
1 Asp Ile Gln Met Thr Gln Ser Pro Ser Ser Leu Ser

Ala Ser Val Gly Asp Arg Val Thr Ile Thr Cys Arg

Ala Ser Gln Ser Val Ser Ser Ala Val Ala Trp Tyr

Gln Gln Lys Pro Gly Lys Ala Pro Lys Leu Leu Ile

Tyr Ser Ala Ser Ser Leu Tyr Ser Gly Val Pro Ser

Arg Phe Ser Gly Ser Gly Ser Gly Thr Asp Phe Thr

Leu Thr Ile Ser Ser Leu Gln Pro Glu Asp Phe Ala

Thr Tyr Tyr Cys Gln Gln Ser Tyr Thr Thr Pro Pro

Thr Phe Gly Gln Gly Thr Lys Val Glu Ile Lys 107
(HVR residues are underlined)
```

Substituted residues with respect to huMAb4D5-8 are indicated in bold/italics above.

Antibodies of the invention can comprise any suitable framework variable domain sequence, provided binding activity to K11-linked polyubiquitin is substantially retained. For example, in some embodiments, antibodies of the invention comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-93). In one embodiment, these antibodies further comprise a human κI light chain framework consensus sequence. In one embodiment, these antibodies comprise at least one, two or all of the light chain HVR sequences of SEQ ID NOs: 2-4, 57-61, 73 and 74. In one embodiment, these antibodies comprise light chain HVR sequences of huMAb4D5-8 as described in U.S. Pat. Nos. 6,407,213 & 5,821,337.) In one embodiment, these antibodies comprise light chain variable domain sequences of huMAb4D5-8 (SEQ ID NO: 783 and 784) (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-93).

In one embodiment, an antibody of the invention is affinity matured to obtain the target binding affinity desired. In one example, an affinity matured antibody of the invention which specifically binds to K11-linked polyubiquitin with high affinity but binds to polyubiquitin having other (non-K11) lysine linkages with substantially reduced affinity comprises substitution at HVR-H2 amino acid positions 60 and 63. In another example, an affinity matured antibody of the invention which specifically binds to K11-linked polyubiquitin with high affinity but binds to polyubiquitin having other (non-K11) lysine linkages with substantially reduced affinity comprises substitution at HVR-H3 amino acid positions 98 and 99. In another example, an affinity matured antibody of the invention which specifically binds to K11-linked polyubiquitin with high affinity but binds to polyubiquitin having other (non-K11) lysine linkages with substantially reduced affinity comprises substitution at HVR-L1 amino acid positions 24, 25, 27, and 28-34. In another example, an affinity matured antibody of the invention which specifically binds to K11-linked polyubiquitin with high affinity but binds to polyubiquitin having other (non-K11) lysine linkages with substantially reduced affinity comprises substitution at HVR-L2 amino acid positions 50-52 and 54.

In one embodiment, an antibody of the invention comprises at least one heavy chain variable domain sequence of SEQ ID NOs: 27-32 and 70-72. In one embodiment, an antibody of the invention comprises at least one light chain variable domain of SEQ ID NOs: 5 and 62-66. In one embodiment, an antibody of the invention comprises a heavy chain variable domain comprising at least one sequence of SEQ ID NOs: 27-32 and 70-72 and also comprises a light chain variable domain comprising at least one sequence of SEQ ID NOs: 5 and 62-66. In other embodiments, an antibody of the invention corresponding to a particular clone number comprises a heavy chain variable domain comprising an HVR-H1, HVR-H2, and HVR-H3 sequence as set forth in FIG. 1B, 4B or 6B for that clone number. In other embodiments, an antibody of the invention corresponding to a particular clone number comprises a light chain variable domain comprising an HVR-L1, HVR-L2 and HVR-L3 sequence as set forth in FIGS. 1A, 4A and 6A for that clone number. In other embodiments, an antibody of the invention corresponding to a particular clone number comprises a heavy chain variable domain comprising an HVR-H1, HVR-H2, and HVR-H3 sequence as set forth in FIG. 1B, 4B or 6B for that clone number and also comprises a light chain variable domain comprising an HVR-L1, HVR-L2 and HVR-L3 sequence as set forth in FIGS. 1A, 4A and 6A for that clone number.

In one aspect, the invention provides an antibody that competes with any of the above-mentioned antibodies for binding to K11-linked polyubiquitin. In one aspect, the invention provides an antibody that binds to the same antigenic determinant on K11-linked polyubiquitin as any of the above-mentioned antibodies.

As shown herein, the antibodies of the invention specifically bind to an isolated polyubiquitin having a specific lysine linkage. As shown herein, the antibodies of the invention also specifically bind to polyubiquitin having a specific lysine linkage when that polyubiquitin is attached to a heterologous protein.

In any of the above embodiments, an anti-K11-linked polyubiquitin antibody is humanized. In one embodiment, an anti-K11-linked polyubiquitin antibody comprises HVRs as in any of the above embodiments, and further comprises an acceptor human framework, e.g. a human immunoglobulin framework or a human consensus framework. In another embodiment, an anti-K11-linked polyubiquitin antibody comprises HVRs as in any of the above embodiments, and further comprises a VH comprising an FR1, FR2, FR3, or FR4 sequence of any of SEQ ID NOs: 27-32 and 70-72. In another embodiment, an anti-K11-linked polyubiquitin antibody comprises HVRs as in any of the above embodiments, and further comprises a VL comprising an FR1, FR2, FR3, or FR4 sequence of any of SEQ ID NOs: 5 and 62-66.

In another aspect, an anti-K11-linked polyubiquitin antibody comprises a heavy chain variable domain (VH) sequence having at least 90%, 91%, 92%, 93%, 94%, 95%, 96%, 97%, 98%, 99%, or 100% sequence identity to the amino acid sequence of any of SEQ ID NOs: 27-32 and 70-72. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-K11-linked polyubiquitin antibody comprising that sequence retains the ability to bind to K11-linked polyubiquitin. In certain embodiments, a total of 1 to 10 amino acids have been substituted, inserted and/or deleted in any one of SEQ ID NOs: 27-32 and 70-72. In certain embodiments, substitutions, insertions, or deletions occur in regions outside the HVRs (i.e., in the FRs). Optionally, the anti-K11-linked polyubiquitin antibody comprises the VH sequence of any of SEQ ID NOs: 27-32 and 70-72, including post-translational modifications of that sequence.

In another aspect, an anti-K11-linked polyubiquitin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of any of SEQ ID NOs: 5 and 62-66. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-K11-linked polyubiquitin antibody comprising that sequence retains the ability to bind to K11-linked polyubiquitin. In certain embodiments, a total of 1 to 10 amino acids have been substituted, inserted and/or deleted in any of SEQ ID NOs: 5 and 62-66. In certain embodiments, the substitutions, insertions, or deletions occur in regions outside the HVRs (i.e., in the FRs). Optionally, the anti-K11-linked polyubiquitin antibody comprises the VL sequence in any of SEQ ID NOs: 5 and 62-66, including post-translational modifications of that sequence.

In another aspect, an anti-K11-linked polyubiquitin antibody is provided, wherein the antibody comprises a VH as in any of the embodiments provided above, and a VL as in any of the embodiments provided above. In one embodiment, the antibody comprises the VH and VL sequences in any of SEQ ID NOs: 27-32 and 70-72 and SEQ ID NOs: 5 and 62-66, respectively, including post-translational modifications of those sequences.

In a further aspect of the invention, an anti-K11-linked polyubiquitin antibody according to any of the above embodiments is a monoclonal antibody, including a chimeric, humanized or human antibody. In one embodiment, an anti-K11-linked polyubiquitin antibody is an antibody fragment, e.g., a Fv, Fab, Fab', scFv, diabody, or F(ab')2 fragment. In another embodiment, the antibody is a full length antibody, e.g., an intact IgG1 antibody or other antibody class or isotype as defined herein.

Compositions comprising at least one anti-K11-linked polyubiquitin antibody or at least one polynucleotide comprising sequences encoding an anti-K11-linked polyubiquitin antibody are provided. In certain embodiments, a composition may be a pharmaceutical composition. As used herein, compositions comprise one or more antibodies that bind to one or more polyubiquitin and/or one or more polynucleotides comprising sequences encoding one or more antibodies that bind to one or more polyubiquitin. These compositions may further comprise suitable carriers, such as pharmaceutically acceptable excipients including buffers, which are well known in the art.

In a further aspect, an anti-K11-linked polyubiquitin antibody according to any of the above embodiments may incorporate any of the features, singly or in combination, as described in Sections 1-7 below:

1. Antibody Affinity

In certain embodiments, an antibody provided herein has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$M or less, e.g. from $10^{-8}$M to $10^{-13}$M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I] antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with, e.g., immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette. Other coupling chemistries for the target antigen to the chip surface (e.g., streptavidin/biotin, hydrophobic interaction, or disulfide chemistry) are also readily available instead of the amine coupling methodology (CM5 chip) described above, as will be understood by one of ordinary skill in the art.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing H$_U$M$_AB$® technology; U.S. Pat. No. 7,041,870 describing K-M MOUSE® technology, and U.S. Patent Application Publication No. US 2007/0061900, describing V$_ELOCI$-M$_OUSE$® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. *in Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J Mol. Biol.* 222: 581-597 (1992); Marks and Bradbury, in *Methods in Molecular Biology* 248:161-175 (Lo, ed., Human Press, Totowa, N.J., 2003); Sidhu et al., *J Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for K11-linked polyubiquitin and the other is for any other antigen. In certain embodiments, bispecific antibodies may bind to two different epitopes of K11-linked polyubiquitin. Bispecific antibodies may also be used to localize cytotoxic agents to cells which express K11-linked polyubiquitin. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to K11-linked polyubiquitin as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |

TABLE 1-continued

| Original Residue | Exemplary Substitutions | Preferred Substitutions |
|---|---|---|
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glermie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-K11-linked polyubiquitin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-K11-linked polyubiquitin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-K11-linked polyubiquitin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-K11-linked polyubiquitin antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with, e.g., any of Fabs A3, A6, A9, B5, F5, or G3, or antibodies G3, 1A11, 1C12, 1F12, 2A3, 2A6, 2D7, 2E6, 2G4, or hybrid antibodies 1C12/2E6 or 2A3/2E6 (as described herein) for binding to K11-linked polyubiquitin. In certain embodiments, such a competing antibody binds to the same epitope (e.g., a linear or a conformational epitope) that is bound by any of Fabs A3, A6, A9, B5, F5, or G3, or antibodies G3, 1A11, 1C12, 1F12, 2A3, 2A6, 2D7, 2E6, 2G4, or hybrid antibodies 1C12/2E6 or 2A3/2E6 (as described herein). Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized K11-linked polyubiquitin is incubated in a solution comprising a first labeled antibody that binds to K11-linked polyubiquitin (e.g., antibodies G3, 1A11, 1C12, 1F12, 2A3, 2A6, 2D7, 2E6, 2G4, or hybrid antibodies 1C12/2E6 or 2A3/2E6) and a second unlabeled antibody that is being tested for its ability to compete with the first antibody for binding to K11-linked polyubiquitin. The second antibody may be present in a hybridoma supernatant. As a control, immobilized K11-linked polyubiquitin is incubated in a solution comprising the first labeled antibody but not the second unlabeled antibody. After incubation under conditions permissive for binding of the first antibody to K11-linked polyubiquitin, excess unbound antibody is removed, and the amount of label associated with immobilized K11-linked polyubiquitin is measured. If the amount of label associated with immobilized K11-linked polyubiquitin is substantially reduced in the test sample relative to the control sample, then that indicates that the second antibody is competing with the first antibody for binding to K11-linked polyubiquitin. See Harlow and Lane (1988) Antibodies: A Laboratory Manual ch.14 (Cold Spring Harbor Laboratory, Cold Spring Harbor, N.Y.).

2. Activity Assays

In one aspect, assays are provided for identifying anti-K11-linked polyubiquitin antibodies thereof having biological activity. Biological activity may include, e.g., modulating the rate of degradation of K11-linked polyubiquitinated proteins in a cell or tissue, and modulating the rate of cell cycle progression of a cell. Antibodies having such biological activity in vivo and/or in vitro are also provided.

In certain embodiments, an antibody of the invention is tested for such biological activity.

D. Immunoconjugates

The invention also provides immunoconjugates comprising an anti-K11-linked polyubiquitin antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-K11-linked polyubiquitin antibodies provided herein is useful for detecting the presence of K11-linked polyubiquitin in a biological sample. The term "detecting" as used herein encompasses quantitative or qualitative detection. In certain embodiments, a biological sample comprises a cell or tissue, such as, but not limited to, a tumor cell, a muscle cell or a nerve cell.

In one embodiment, an anti-K11-linked polyubiquitin antibody for use in a method of diagnosis or detection is provided. In a further aspect, a method of detecting the presence of K11-linked polyubiquitin in a biological sample is provided. In certain embodiments, the method comprises contacting the biological sample with an anti-K11-linked polyubiquitin antibody as described herein under conditions permissive for binding of the anti-K11-linked polyubiquitin antibody to a polyubiquitin or polyubiquitinated protein, and detecting whether a complex is formed between the anti-K11-linked polyubiquitin antibody and the polyubiquitin or polyubiquitinated protein. Such method may be an in vitro or in vivo method. In one embodiment, an anti-K11-linked polyubiquitin antibody is used to select subjects eligible for therapy with an anti-K11-linked polyubiquitin antibody, e.g. where K11-linked polyubiquitin is a biomarker for selection of patients.

Exemplary disorders that may be diagnosed using an antibody of the invention include cell-cycle-related diseases or disorders, which may be a disease or disorder associated with aberrantly increased cell cycle progression or a disease or disorder associated with aberrantly decreased cell cycle progression. In one aspect, a disease or disorder associated with aberrantly increased cell cycle progression is cancer. In another aspect, a disease or disorder associated with aberrantly decreased cell cycle progression is, e.g., a degenerative muscle disorder or a degenerative nerve disorder.

In certain embodiments, labeled anti-K11-linked polyubiquitin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-K11-linked polyubiquitin antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide one or more chemotherapeutic agents. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-K11-linked polyubiquitin antibodies provided herein may be used in therapeutic methods.

In one aspect, an anti-K11-linked polyubiquitin antibody for use as a medicament is provided. In further aspects, an anti-K11-linked polyubiquitin antibody for use in treating disorders associated with aberrant cell cycle regulation (including, but not limited to, proliferation disorders such as cancer and hypotrophy disorders including, but not limited to, degenerative muscle disorders and degenerative nerve disorders) is provided. In certain embodiments, an anti-K11-linked polyubiquitin antibody for use in a method of treatment is provided. In certain embodiments, the invention provides an anti-K11-linked polyubiquitin antibody for use in a method of treating an individual having a disorder associated with aberrant cell cycle regulation, comprising administering to the individual an effective amount of the anti-K11-linked polyubiquitin antibody. In one such embodiment, the method further comprises administering to the individual an effective amount of at least one additional therapeutic agent, e.g., as described below. In further embodiments, the invention provides an anti-K11-linked polyubiquitin antibody for use in modulating cell cycle regulation such that the rate of cell cycle progression is adjusted. In certain embodiments, the invention provides an anti-K11-linked polyubiquitin antibody for use in a method of modulating the rate of cell cycle progression in an individual comprising administering to the individual an effective of the anti-K11-linked polyubiquitin antibody to modulate cell cycle progression and thereby adjust the rate of cell division. An "individual" according to any of the above embodiments is preferably a human.

In a further aspect, the invention provides for the use of an anti-K11-linked polyubiqutin antibody in the manufacture or preparation of a medicament. In one embodiment, the medicament is for treatment of disorders associated with aberrant cell cycle regulation (including, but not limited to, proliferation disorders such as cancer and hypotrophy disorders including, but not limited to, degenerative muscle disorders and degenerative nerve disorders). In a further embodiment, the medicament is for use in a method of treating a disorder associated with aberrant cell cycle regulation comprising administering to an individual having such a disorder an effective amount of the medicament. In one such embodiment, the method further comprises administering to the individual an effective amount of at least one additional therapeutic agent, e.g., as described below. In a further embodiment, the medicament is for modulating the rate of cell cycle progression. In a further embodiment, the medicament is for use in a method of modulating the rate of cell cycle progression in an individual comprising administering to the individual an amount effective of the medicament to adjust the rate of cellular division. An "individual" according to any of the above embodiments may be a human.

In a further aspect, the invention provides a method for treating a disorder associated with aberrant cell cycle regulation. In one embodiment, the method comprises administering to an individual having such a disorder associated with aberrant cell cycle regulation an effective amount of an anti-K11-linked polyubiquitin antibody. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the anti-K11-linked polyubiquitin antibodies provided herein, e.g., for use in any of the above therapeutic methods. In one embodiment, a pharmaceutical formulation comprises any of the anti-K11-linked polyubiquitin antibodies provided herein and a pharmaceutically acceptable carrier. In another embodiment, a pharmaceutical formulation comprises any of the anti-K11-linked polyubiquitin antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhôone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC ®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945. Intracellular expression of an intrabody is effected by introducing a nucleic acid encoding the desired antibody or antigen-binding portion thereof (lacking the wild-type leader sequence and secretory signals normally associated with the gene encoding that antibody of antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest. One or more nucleic acids encoding all or a portion of an anti-polyubiquitin antibody of the invention can be delivered to a target cell, such that one or more intrabodies are expressed which are capable of intracellular binding to a polyubiquitin and modulation of one or more polyubiquitin-mediated cellular pathways.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA 90: 7889-7893 (1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes. See, e.g., Chen et al., Proc. Natl. Acad. Sci. USA 96: 4325-4329 (1999).

When the binding target is located in the brain, certain embodiments of the invention provide for the antibody or antigen-binding fragment thereof to traverse the blood-brain barrier. Certain neurodegenerative diseases are associated with an increase in permeability of the blood-brain barrier, such that the antibody or antigen-binding fragment can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or antigen-binding fragment across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002); interstitial infusion/convection-enhanced delivery (see, e.g., Bobo et al., Proc. Natl. Acad. Sci. USA 91: 2076-2080 (1994)), and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, vols. 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or antigen-binding fragment across the blood-brain barrier include, but are not limited to, encapsulating the antibody or antigen-binding fragment in liposomes that are coupled to antibody binding fragments that bind to receptors on the vascular endothelium of the blood-brain barrier (see, e.g., U.S. Patent Application Publication No. 20020025313), and coating the antibody or antigen-binding fragment in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or antigen-binding fragment across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473); inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-K11-linked polyubiquitin antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-K11-linked polyubiquitin antibody.

III. Examples

The following are examples of methods and compositions of the invention. It is understood that various other embodiments may be practiced, given the general description provided above.

Example 1

Isolation and Characterization of Anti-K11-linked Polyubiquitin Antibodies

Phage display-based isolation of anti-K11-linked polyubiquitin antibodies was performed with several different libraries using standard techniques. Briefly, enzymatically synthesized full-length K11-linked diubiquitin (Michael Rape's lab, UC Berkeley) was immobilized on 96-well Maxisorb immunoplates (NUNC). Plates were coated overnight at 4° C. with 5 µg/mL K11 diubiquitin in 50 mM sodium carbonate buffer, pH 9.6. The coated plates were subsequently blocked with 200 µL/well of 2.5% milk in PBS containing 0.05% Tween 20 (PBST). The naïve phage library was precipitated from glycerol stocks with 1/5 volume of 20% PEG/2.5M NaCl and resuspended in 2.5% milk/PBST and incubated at 25° C. for one hour. The resuspended phage were added (100 µL/well) to the blocked plates and incubated at 25° C. for four hours with shaking. After binding, plates were washed ten times with PBST, and phage were eluted with 150 µL/well of 50 mM HCl/500 mM KCl for 30 minutes at 25° C. with shaking. The elution was neutralized with 150 µL/well 1M Tris, pH 7.5 and subsequently propagated in XL-1-Blue $E.$ $coli$ (Stratagene) with the addition of M13K07 helper phage.

Amplified phage were used for additional rounds of selection against K11-linked diubiquitin as above. In rounds two through four, soluble monoubiquitin or polyubiquitin of different linkage forms were added to the phage for counterselection. In the second round, 10 µg/mL of soluble monoubiquitin (Boston Biochem) was used. In the third and fourth rounds, 10 µg/mL each of soluble monoubiquitin, linear diubiquitin, K48-linked polyubiquitin 2-7, and K63-linked polyubiquitin 2-7 chains (all Boston Biochem) were used.

Ninety-six individual clones from both the third and the fourth rounds of sorting from each library were grown up in a 96-well format in 1 mL of 2YT broth containing 50 µg/mL carbenicillin and $10^{10}$ phage/mL M13K07 helper phage at 37° C. overnight with shaking. Cells were pelleted, and supernatants used in high-throughput phage spot ELISAs for binding to K11-linked diubiquitin, monoubiquitin, linear diubiquitin, K48-linked polyubiquitin 2-7, K63-linked polyubiquitin 2-7, an anti-gD antibody (Genentech), or an uncoated well. All of the Fab phage display libraries contained a carboxy-terminal gD tag on the light chain which permits assessment of display level by observing the binding of an anti-gD antibody. The panel of ubiquitin proteins was immobilized on 384-well Maxisorb immunoplates (NUNC) as above. Plates were coated overnight at 4° C. with 2 µg/mL of each ubiquitin protein in 50 mM sodium carbonate buffer, pH 9.6. The coated plates were subsequently blocked with 60 µL/well of 2.5% milk in PBST for one hour at 25° C. with shaking. After one hour, the blocking buffer was removed and 20 µL/well of PBST and 10 µL/well of phage supernatant were added. Plates were incubated at 25° C. for one hour with shaking. The plate was washed six times with PBST. Thirty microliters of a 1:5,000 dilution of an anti-M13 horseradish peroxidase-conjugated secondary antibody (GE Healthcare) in PBST was used for detection of phage binding. After washing, bound secondary antibody was detected using a TMB substrate (KPL) followed by quenching with an equal volume of 1 M phosphoric acid, and spectrophotometric readings at 450 nm.

A naïve anti-peptide Fab phage display library was subjected to four rounds of sorting against the above-referenced purified K11-linked diubiquitin (UC Berkeley) as described above. The anti-peptide Fab phage display library used contains randomized amino acids in all three heavy chain CDRs and light chain CDRL3, and was based on a modified humanized antibody 4D5 framework, with a longer CDRL1 and permitting CDRL2 sequence variation. No enrichment in specific anti-K11-linked diubiquitin binders was observed after four rounds of sorting.

Next, a naïve YSGX Fab phage display library was subjected to four rounds of sorting against the above-referenced purified K11-linked diubiquitin (UC Berkeley) as described above. The YSGX Fab phage display library used contains randomized amino acids in all three heavy chain CDRs and in light chain CDRL3 (see U.S. published patent application no. 2005-0106667 and Fellouse et al. 2007 J. Mol. Biol. 373: 924-40), and is based on humanized antibody 4D5. Only a modest three-fold enrichment in binders for K11-linked diubiquitin was observed after four rounds of sorting. Of these binders, all showed a weak signal for binding to K11-linked diubiquitin with additional weak binding to the other ubiquitin and polyubiquitin forms.

Figure 2:
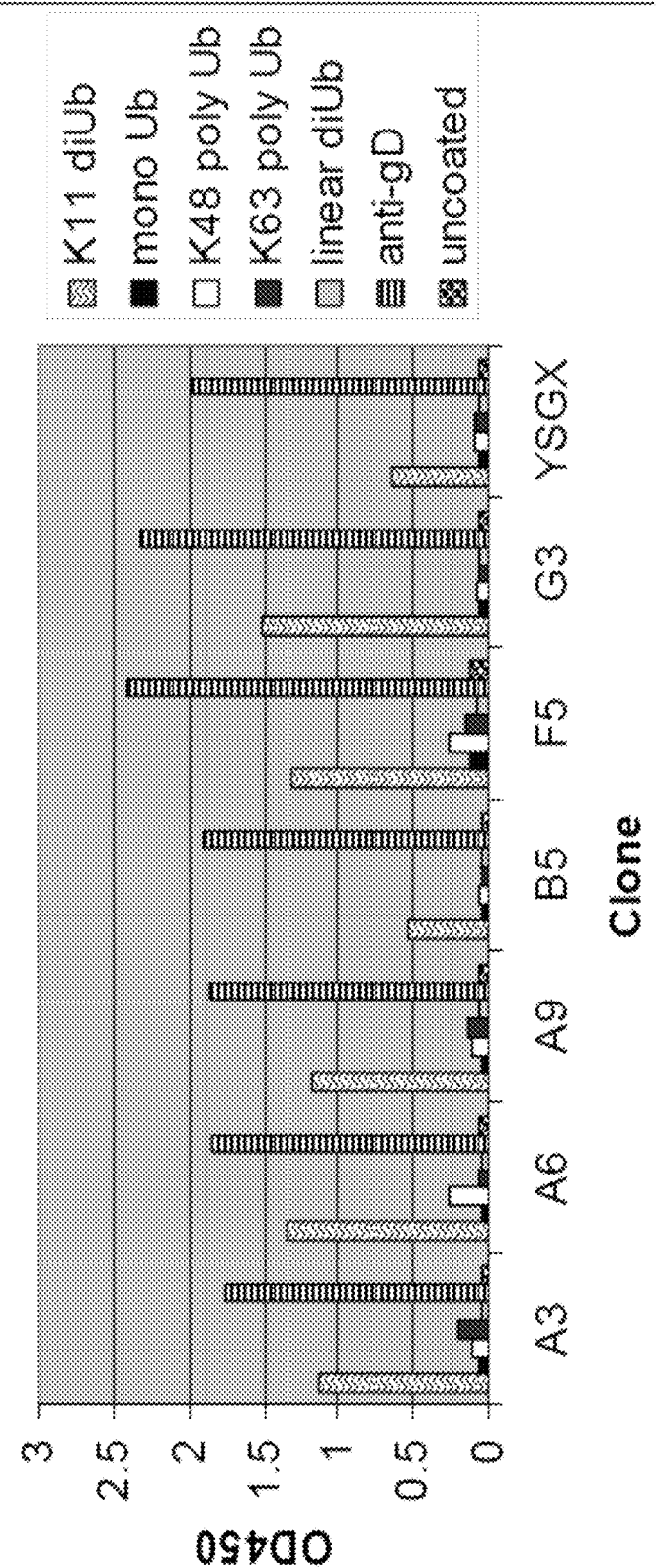
FIG. 2 depicts a phage spot ELISA demonstrating the relative binding signals at a wavelength of 450 nm for each obtained clone to a panel of ubiquitin proteins, as described in Example 1. Fab library clones each contained a gD tag and display of the Fab on phage was assessed by binding to an anti-gD antibody. An uncoated well was used as a negative control.

Finally, a naïve VH Fab phage display library was subjected to four rounds of sorting against the above-referenced K11-linked diubiquitin. The VH Fab phage display library contains randomized amino acids in all three heavy chain CDRs (see U.S. Published Patent Application No. US20050119455 and Lee C. W. et al. 2004 JMB 340: 1073-93), and is based on a humanized antibody 4D5. Twenty-four-fold enrichment was observed after four rounds of sorting. Strong K11-linked diubiquitin-specific binders were identified from this library sorting. The heavy chains of VH library clones from the third and fourth rounds of sorting were sequenced. The HVR H1, HVR H2, and HVR H3 sequences were expected to be clone-specific whereas the heavy chain framework sequences and the entire light chain sequence (HVR and framework regions) were expected to be invariant, based on the VH library design. The HVR L1 sequence was RASQDVSTAVA (SEQ ID NO: 2), the CDR L2 sequence was SASFLYS (SEQ ID NO: 3), and the HVR L3 sequence was QQSYTTPPT (SEQ ID NO: 4) (FIG. 1A). Six unique heavy chain sequences were identified (FIG. 1B), and given designators A3, A6, A9, B5, F5 and G3. Clone G3 was the strongest binder to K11-linked diubiquitin and the most specific in the phage spot ELISA assay described above; it showed no binding to monoubiquitin, linear diubiquitin, K48-linked polyubiquitin 2-7, or K63-linked polyubiquitin 1-7 (FIG. 2). The consensus amino acid sequences of the HVR regions of the heavy chains of these six Fabs were: HVR H1: X1 X2 X3 X4 Ile X5 (SEQ ID NO: 24), wherein X1 is selected from serine and threonine, X2 is selected from asparagine, aspartic acid, serine and glycine, X3 is selected from tyrosine, serine and threonine, X4 is selected from tryptophan, aspartic acid, glycine and tyrosine, and X5 is selected from serine and histidine; HVR H2: X6 X7 Ile X8 P X9 G X10 T X11 (SEQ ID NO: 25), wherein X6 is selected from glycine and alanine, X7 is selected from aspartic acid, tryptophan, glycine, glutamic acid and valine, X8 is selected from serine, tyrosine and asparagine, X9 is selected from aspartic acid, alanine, histidine and asparagine, X10 is selected from tyrosine and serine, and X11 is selected from tyrosine, aspartic acid and asparagine; and HVR H3: X12 X13 X14 X15 X16 X17 X18 X19 X20 X21 D (SEQ ID NO: 26), wherein X12 is selected from arginine and lysine, X13 is selected from glutamic acid, glycine, aspartic acid and proline, X14 is selected from serine, isoleucine, valine and tryptophan, X15 is selected from tryptophan, glycine, tyrosine and phenylalanine, X16 is selected from tryptophan, tyrosine, leucine, glycine and phenylalanine, X17 is selected from serine, tyrosine, phenylalanine and glycine, X18 is selected from alanine, phenylalanine, tyrosine and glycine, or is not present, X19 is selected from tryptophan, glycine, alanine and tyrosine, or is not present, X20 is valine or is not present, and X21 is selected from methionine and phenylalanine.

A. Production of the G3 Fab

Clones from the VH Fab phage display library were expressed under the control of the E. coli alkaline phosphatase (PhoA) promoter. Both the light chain and the heavy chain contained an amino-terminal bacterial stII signal sequence to allow secretion in E. coli and were expressed from a single phagemid vector. The heavy chain carboxyl terminus was fused in-frame to a leucine zipper followed by gene product III (gpIII) of the M13 bacteriophage, allowing for display of a bivalent Fab-zip fragment on phage. In order to express soluble Fab, a stop codon was introduced into the G3 phagemid between the end of the CH1 constant domain of the Fab and the start of the leucine zipper. Mutagenic oligonucleotides RF6471-1 (TCTTGTGACAAAACT-CACTAATAAC GCATGAAACAGCTAGAGG) (SEQ ID NO:33) and RF6471-2 (CCTCTAGCTGTTTCATGCG TTATTAGTGAGTTTTGTCACAAGA) (SEQ ID NO:34) were used to insert the stop codon using the QuikChange® Lightning Site-Directed Mutagenesis kit (Stratagene). The resulting soluble G3 Fab expression plasmid was transformed into the E. coli strain 62A7 (Genentech) and plated on solid agar containing carbenicillin. A single colony was used to inoculate 25 mL of 2YT broth containing 50 µg/mL carbenicillin. The culture was grown overnight at 37° C. and 5 mL were used to inoculate 500 mL of complete C.R.A.P. media (3.57 g $(NH_4)_2SO_4$, 0.71 g sodium citrate $2H_2O$, 1.07 g KCl, 5.36 g yeast extract (certified), 5.36 g Hycase SF (Sheffield), pH adjusted to 7.3 by addition of KOH and volume adjusted to 872 mL with ultrapure water, autoclaved, cooled to 55° C., to which was added (per L) 110 mL 1M MOPS pH 7.3, 11 mL 50% glucose, and 7 mL 1M $MgSO_4$) with 50 µg/mL carbenicillin. The cultures were grown at 30° C. for 24 hours with shaking. Cells were harvested by centrifugation and pellets were stored at −20° C. The Fab was purified by resuspending the cell pellet in 35 mL of cold wash buffer (Phosphate Buffered Saline (PBS)+150 mM NaCl) containing 10 µg/mL DNaseI (Invitrogen), 0.2 mg/mL lysozyme (USB), and 1 mM phenylmethylsulphonylfluoride (Calbiochem). The pellet was resuspended by vortexing rapidly for 45 minutes at 25° C. Cell debris was pelleted by centrifugation and lysate was loaded on 1 mL protein A-sepharose (GE Healthcare) column preequilibrated with cold wash buffer. The column was washed with 50 mL of cold wash buffer, eluted with 3 mL of 0.1 M acetic acid, and neutralized with 150 µL of 2 M Tris, pH 11.0. The Fab was concentrated using Amicon Ultra-15 centrifugal filter units (10 kDa cut-off, Millipore). The resulting Fab concentration was determined spectrophotometrically (1 $OD_{280}$=1.5 mg/mL).

B. Analysis of the G3 Fab

The affinity of the G3 Fab was determined by surface plasmon resonance (SPR) using a BIACORE™ 3000 (GE Healthcare). Approximately 60 resonance units (RUs) of K11-linked diubiquitin (Genentech), K48-linked diubiquitin (Boston Biochem), and K63-linked diubiquitin (Boston Biochem) were immobilized on separate flow cells of a CM5 chip using the amine coupling protocol supplied by the manufacturer. Two-fold serial dilutions (0.5-500 nM) of G3 Fab in 10 mM Hepes, pH 7.2, 150 mM NaCl, and 0.01% Tween 20 (HBST) were injected (60 µL total at a flow rate of 30 µL/minute) over each flow cell using HBST as the running buffer. The signal for each flow cell was recorded and the reference signal from an unconjugated and blocked flow cell was subtracted. Following a dissociation period of eight minutes, the chip surface was regenerated with 20 µL of 10 mM HCl. Data were fit to a 1:1 binding model with drifting baseline. Kinetic constants and binding constants were simultaneously calculated by nonlinear regression analysis, using software provided by the manufacturer, and are shown in Table 2, top row. The average (Avg.) and the standard deviation (Std. dev.) from three measurements of the kinetic constants ($k_a$ and $k_d$) and binding constant ($K_D$) of the G3 Fab are shown. G3 binds K11-linked diubiquitin with a binding constant of 105 nM. It demonstrates no detectable binding to K48-linked diubiquitin or K63-linked diubiquitin.

TABLE 2

Binding Properties of Anti-K11-Linked Polyubiquitin Fabs and Antibodies

| Fab | Avg. ka (1/Ms) | ka std dev (1/Ms) | K11 DiUb Avg. kd (1/s) | kd std dev (1/s) | Avg. KD (nM) | KD std dev (nM) | K48 DiUb | K63 DiUb | mutant CDRs |
|---|---|---|---|---|---|---|---|---|---|
| G3 WT     | 3.02E+05 | 4.34E+04 | 3.16E−02 | 3.87E−03 | 105 | 3.00E+00 | NDB | NDB |       |
| G3L1.1A11 | 3.46E+05 | 3.00E+04 | 2.66E−02 | 6.32E−03 | 76  | 1.48E+01 | NDB | NDB | L1    |
| G3L1.1C12 | 4.44E+05 | 1.61E+04 | 1.53E−02 | 6.43E−04 | 35  | 5.77E−01 | NDB | NDB | L1    |
| G3L2.1F12 | 3.43E+05 | 2.69E+04 | 2.63E−02 | 2.22E−03 | 74  | 9.07E+00 | NDB | NDB | L1    |
| G3HC.2A3  | 6.53E+05 | 5.32E+04 | 1.60E−02 | 1.51E−03 | 25  | 3.21E+00 | NDB | NDB | L1    |
| G3HC.2A6  | 2.43E+05 | 1.97E+04 | 1.50E−02 | 5.69E−04 | 62  | 3.06E+00 | NDB | NDB | H3    |
| G3HC.2D7  | 2.08E+05 | 1.14E+04 | 1.63E−02 | 1.14E−03 | 79  | 4.16E+00 | NDB | NDB | H3    |
| G3HC.2E6  | 3.60E+05 | 3.20E+04 | 1.69E−02 | 8.89E−04 | 47  | 4.36E+00 | NDB | NDB | H2    |
| G3HC.2G4  | 3.92E+05 | 3.61E+04 | 1.62E−02 | 1.15E−03 | 41  | 2.31E+00 | NDB | NDB | L1    |
| 1C12/2E6  | 5.46E+05 | 1.04E+04 | 6.71E−03 | 4.37E−04 | 12  | 5.77E−01 | NDB | NDB | L1/H2 |
| 2A3/2E6   | 6.48E+05 | 3.95E+04 | 7.45E−03 | 2.19E−04 | 12  | 1.15E+00 | NDB | NDB | L1/H2 |

NDB = no detectable binding observed

The purified G3 Fab was tested for binding to a panel of ubiquitin proteins by ELISA. K11-linked diubiquitin (UC Berkeley), monoubiquitin (Boston Biochem), linear diubiquitin (Boston Biochem), K48-linked diubiquitin (Boston Biochem), and K63-linked diubiquitin (Boston Biochem) were immobilized on 96-well Maxisorb immunoplates. Plates were coated at 25° C. for two hours with 5 μg/mL of each protein in 50 mM sodium carbonate buffer, pH 9.6 with shaking. The coated plates were blocked with 200 μL/well of 2.5% milk in PBST for one hour at 25° C. with shaking. Twelve two-fold serial dilutions of the G3 Fab were made in 2.5% milk in PBST from 1.0 μM to 0.5 nM. After one hour, the blocking buffer was removed and 100 μL/well of each G3 Fab dilution was added and incubated at 25° C. for one hour with shaking. The plate was then washed 12 times with PBST using a plate washer. A 1:5,000 dilution of an anti-human kappa light chain-specific HRP-conjugated secondary antibody (Sigma Aldrich) in PBST was used for detection of Fab binding. 100 μL/well of the secondary dilution was added and the plate was incubated at 25° C. for 30 minutes with shaking. The plate was then washed 12 times with PBST using a plate washer and twice with PBS manually. Bound secondary antibody was detected using a TMB substrate (KPL) followed by quenching with an equal volume of 1 M phosphoric acid. The absorbance was read at 450 nm. The G3 Fab showed concentration-dependent binding to only K11-linked diubiquitin, but not monoubiquitin, linear diubiquitin, K48-linked diubiquitin, or K63-linked diubiquitin (FIG. 3A). Thus, G3 is highly specific for K11-linked diubiquitin in an ELISA format.

The G3 Fab was further tested in an IC50 competition ELISA to get another estimate of affinity. An initial titer ELISA was performed to determine the concentration of Fab at which a signal of $OD_{450}=0.5$ would be achieved. K11-linked diubiquitin (Genentech) was immobilized on 96-well Maxisorb immunoplates by coating overnight at 4° C. at a concentration of 1 μg/mL in 50 mM sodium carbonate buffer, pH 9.6. The coated plates were blocked with 200 μL/well of 2.5% milk in PBST for one hour at 25° C. with shaking. Twelve two-fold serial dilutions of the G3 Fab were made in 2.5% milk in PBST from 1 μM to 0.5 nM. After one hour, the blocking buffer was removed and 100 μL/well of each G3 Fab dilution was added and incubated at 25° C. for 15 minutes with shaking. The plate was then washed six times with PBST using a plate washer. A 1:5,000 dilution of a goat anti-human Fab fragment-specific HRP-conjugated secondary antibody (Sigma Aldrich) in PBST was used for detection of Fab binding. 100 μL/well of the secondary dilution was added and the plate was incubated at 25° C. for 30 minutes with shaking. The plate was then washed 12 times with PBST using a plate washer and twice with PBS manually. Bound secondary antibody was detected using a TMB substrate (KPL) followed by quenching with an equal volume of 1 M phosphoric acid. The absorbance was read at 450 nm. The concentration of Fab at which an $OD_{450}=0.5$ was 94 nM. Two-fold serial dilutions of soluble K11-linked diubiquitin plus 94 nM of G3 Fab in 2.5% milk in PBST were incubated at 25° C. for one hour with shaking. The amount of unbound Fab at each K11-linked diubiquitin concentration was then measured by incubating the mixtures with a 96-well Maxisorb immunoplate that had been coated with 1 μg/mL K11-linked diubiquitin and blocked with 2.5% milk in PBST. The Fab/K11 mixture was incubated on the plate for 15 minutes at 25° C. with shaking. The plate was then washed six times with PBST using a plate washer. A 1:5,000 dilution of a goat anti-human Fab fragment-specific HRP-conjugated secondary antibody (Sigma Aldrich) in PBST was used for detection of Fab binding. 100 μL/well of the secondary dilution was added and the plate was incubated at 25° C. for 30 minutes with shaking. The plate was then washed 12 times with PBST using a plate washer and twice with PBS manually. Bound secondary antibody was detected using a TMB substrate (KPL) followed by quenching with an equal volume of 1 M phosphoric acid. The absorbance was read at 450 nm. The absorbance was plotted against K11-linked diubiquitin concentration and shows that the IC50 is 75 nM (FIG. 3B). This is consistent with the 105 nM $K_D$ determined by SPR, above.

The G3 Fab was also tested for its ability to specifically bind to K11-linked diubiquitin (UC Berkeley), monoubiquitin (Boston Biochem), linear diubiquitin (Boston Biochem), K48-linked diubiquitin (Boston Biochem), and K63-linked diubiquitin (Boston Biochem) in a Western blot. One μg of each protein in 1×LDS buffer (Invitrogen) with reducing agent was heated at 70° C. for ten minutes and run on 4-12% NuPAGE Bis Tris 1.0 mm gels in MES buffer (Invitrogen) in duplicate. One gel was stained by coomassie blue to detect all proteins. The other gel was transferred at constant 30 V for one hour by wet transfer in 10% methanol and 1×NuPAGE transfer buffer (Invitrogen) to 0.2 μm nitrocellulose (Invitrogen). Non-specific binding sites on the membrane were blocked by incubation in 5% milk in PBST for one hour at 25° C. with shaking. The membrane was then incubated in 5 μg/mL of G3 Fab in 5% milk in PBST for 1.5 hours at 25° C. with shaking. The membrane was washed three times in PBST with shaking. The G3 Fab was detected by incubating the membrane in a 1:10,000 dilution of a goat anti-human Fab fragment-specific HRP-conjugated secondary antibody (Sigma Aldrich) in 5% milk in PBST for one hour at 25° C. with shaking. The membrane was then washed three times in PBST followed by one wash in PBS. The secondary antibody was detected using Super Signal West Pico chemiluminescent substrate (Pierce Biotechnology) followed by exposure of the blots to film. The G3 Fab detected only the K11-linked diubiquitin but not monoubiquitin, linear diubiquitin, K48-linked diubiquitin, or K63-linked diubiquitin (see FIG. 3C). Thus, it is highly specific for K11-linked diubiquitin in a western blot format as well.

Example 2

Affinity Maturation of a K11 Linkage-Specific Fab

A. Conversion of the G3 Phagemid to Monovalent Fab Display and Stop Template Generation The G3 phagemid clone from the VH library was converted from bivalent Fab-zip format to monovalent Fab display for affinity maturation purposes. The leucine zipper between the end of the CH1 constant domain and gpIII was removed using Kunkel mutagenesis (see Kunkel, Proc. Natl. Acad. Sci. USA 82:488 (1985)). A TAA stop codon was simultaneously inserted separately into either CDR L1, CDR L2, CDR L3, CDR H3, or both CDRs L3 and H3 (resulting in L1, L2, L3, H3, and L3/H3 stop templates, respectively) for library synthesis. Stop codons force diversity within a particular CDR loop by requiring repair of the stop in order to obtain full length Fab expression and display on phage. Mutagenic oligonucleotide F220-delzip (TCTTGT-GACAAAACTCACAGTGGCGGTGGCTCTGGT) (SEQ ID NO: 35) was combined separately with each one of the stop codon mutagenic oligonucleotides listed below and 1 μg of G3 phagemid Kunkel DNA. The CDR L1 stop mutagenic oligonucleotide used to insert a TAA stop codon at position 24 (Kabat numbering) within CDR L1 of the light chain was 4D5LC1.stop (GTCACCATCACCTGC<u>TAA</u>GCCAGTCAGGATGTG) (SEQ ID NO:36). The CDR L2 stop mutagenic oligonucleotide used to insert a TAA stop codon at position 50 (Kabat numbering) within CDR L2 of the light chain was 4D5LC2.stop (GAAGCTTCTGATT-TAC<u>TAA</u>GCATCCTTCCTCTAC) (SEQ ID NO:37). The CDR L3 stop mutagenic oligonucleotide used to insert a TAA stop codon at position 89 (Kabat numbering) within CDR L3 of the light chain was 4D5LC3.stop (GCAACTT-ATTACTGT<u>TAA</u>CAATCTTATACTACTC) (SEQ ID NO:38). The CDR H3 stop mutagenic oligonucleotide used to insert a TAA stop codon at position 98 (Kabat numbering) within CDR H3 of the heavy chain was VH5CDRH3: 413Vh5SRo6 (GAGGACACTGCCGTCTATTATTGT-GCTCGTGAGGCCTCG<u>TAA</u>CTGCCCCCCTACGTTA TGGACTACTGGGGTCAAGGAACACTAGTC) (SEQ ID NO:39). The resulting monovalent Fab phagemid stop templates were used for affinity maturation library generation.

B. Affinity Maturation Library Generation

Two affinity maturation approaches were taken. In the first approach, libraries were generated which contained amino acid diversity only within the light chain. These "light chain" libraries allowed for soft randomization of each light chain CDR position, as described below. In the second approach, libraries were generated which contained amino acid diversity in both the heavy chain and light chain CDRs in various combinations. These "heavy chain" libraries contained either amino acid diversity found within naturally occurring human antibodies or soft randomization of mainly surface exposed residues, as described below.

All libraries were generated by Kunkel mutagenesis (see Kunkel, Proc. Natl. Acad. Sci. USA 82:488 (1985)). In the case of soft randomization, degenerate oligonucleotides were synthesized such that the wild-type residue would be retained 50% of the time and 50% of the time one of the remaining 19 amino acids would be encoded. To achieve soft randomization, oligonucleotides were designed such that certain nucleotide positions were occupied 70% of the time with the indicated base and 10% of the time occupied by one of the three other bases (Gallop et al., J. Med. Chem. 37:1233 (1994)). For those oligonucleotides where such soft randomization was included at a particular base, the presence of soft randomization is indicated by the presence of a number at that base position. The number "5" indicates that the base adenine is present 70% of the time at that position, while the bases guanine, cytosine, and thymine are each present 10% of the time. Similarly, the number "6" refers to guanine, "7" to cytosine, and "8" to thymine, where in each case, each of the other three bases is present only 10% of the time. In the case of hard randomization, degenerate oligonucleotides were synthesized such that amino acid diversity found at certain positions within natural human antibodies would be allowed. In this case degenerate codons were used where the letter "R" encodes for guanine or adenine, "Y" encodes for thymine or cytosine, "M" encodes for adenine or cytosine, "K" encodes for guanine or thymine, "S" encodes for guanine or cytosine, "W" encodes for adenine or thymine, "H" encodes for adenine, cytosine, or thymine, "B" encodes for guanine, thymine, or cytosine, "V" encodes for guanine, cytosine, or adenine, "D" encodes for guanine, adenine, or thymine, and "N" encodes for guanine, adenine, cytosine, or thymine.

Four "light chain" libraries were generated and designated L1, L2, L3, and L1/L2/L3. The L1 library had positions 24-34 (Kabat numbering) of the light chain soft randomized. Mutagenic oligonucleotide L1 (GATAGGGTCACCATCAC CTGC7686765677566586865675776766866T GGTAT-CAACAGAAACCAGGA) (SEQ ID NO:40) and 20 μg of Kunkel DNA of the L1 stop template (described in Example 2A) were used to generate the library by Kunkel mutagenesis. The L2 library had positions 50-56 (Kabat numbering) of the light chain soft randomized. Mutagenic oligonucleotide L2 (AAAGCTCCGAAGCTTCTGATT-TAC567676567887786857567 GGAGTCCCTTCTCGCT-TCTCT) (SEQ ID NO:41) and 20 μg of Kunkel DNA of the L2 stop template (described in Example 2A) were used to generate the library by Kunkel mutagenesis. The L3 library had positions 89-97 (Kabat numbering) of the light chain soft randomized. Mutagenic oligonucleotide L3 (GACT-TCGCAACTTATTACTGT75675656785757757777 6776577TTCGGACAGGGTACCAAGGTG) (SEQ ID NO:42) and 20 μg of Kunkel DNA of the L3 stop template (described in Example 2A) were used to generate the library by Kunkel mutagenesis. The L1/L2/L3 library had positions 24-34, 50-56, and 89-97 (Kabat numbering) of the light chain soft randomized. Mutagenic oligonucleotides L1 (SEQ ID NO:40), L2 (SEQ ID NO:41), and L3 (SEQ ID NO:42) described above and 20 µg of Kunkel DNA of the L3 stop template (described in Example 2A) were used to generate the library by Kunkel mutagenesis.

Six "heavy chain" libraries were also generated and designated L1/L2/L3hard, L3/H1/H2, L3/H3, L1/H3, H2/H3, and H3. The L1/L2/L3hard library had positions 28-33, 50, 53, 55, 91-94, and 96 (Kabat numbering) of the light chain hard randomized to allow for amino acid diversity found at these positions within natural human antibodies. The L1 mutagenic oligonucleotides F111-L1 (ACCTGCCGTGCCAGTCAGRDTRKTRVWANWTHTGTAGCCTGGTATCAAC AGAAAC) (SEQ ID NO:43) and F202-L1 (ACCTGCCGTGCCAGTCAGRDTRKTRVWANWTHTCTGGCCTGGTATCAACAGAAAC) (SEQ ID NO:44) were mixed at a 1:2 ratio, the L2 mutagenic oligonucleotides F201-L2 (CCGAAGCTTCTGATTTACKBGGCATCCAVCCTCT ACTCTGGAGTCCCT) (SEQ ID NO:45) and F203-L2 (CCGAAGCTTCTGATTTACKBGGCA TCCAVCCTCGMATCTGGAGTCCCTTCTCGC) (SEQ ID NO:46) were mixed at a 1:1 ratio, and the L3 mutagenic oligonucleotides F133a (GCAACTTATTACTGTCAGCAATMTDMCRVT NHTCCTYKGACGTTCGGACAGGGTACC) (SEQ ID NO:47), F133b (GCAACTTATTACTG TCAGCAATMTDMCRVTNHTCCTTWTACGTTCGGACAGGGTACC) (SEQ ID NO:48), F133c (GCAACTTATTACTGTCAGCAASRTDMCRVTNHTCCTYKGACGTTCGGACAG GGTACC) (SEQ ID NO:49), F133d (GCAACTTATTACTGTCAGCAASRTDMCRVTNHTCCTTWTACGTTCGGACAGGGTACC) (SEQ ID NO:50) were mixed at a 1:1:1:1 ratio. Equal amounts of each of these mixes and 20 µg of Kunkel DNA of the L3 stop template (described in Example 2A) were used to generate the library by Kunkel mutagenesis.

The L3/H1/H2 library had positions 91-94, 96 (Kabat numbering) of the light chain and positions 30-32, 50, 52 (but not 52a), 53, and 54 (Kabat numbering) of the heavy chain soft randomized. The L3 mutagenic oligonucleotides F563-L3soft1 (ACTTATTACTGTCAGCAA878857577577CCT777ACGTTCGGACAGGGTACC) (SEQ ID NO: 51), F564-L3soft2 (ACTTATTACTGTCAGCAA878857577577CCTTWTACGTTCGGACAGG GTACC) (SEQ ID NO: 52), and F565-L3soft3 (ACTTATTACTGTCAGCAA878857577577CCTYKGACGTTCGG ACAGGGTACC) (SEQ ID NO: 53) were mixed at a 1:0.5:1 ratio. Equal amounts of the L3 oligo mix and mutagenic oligonucleotides G3CDRHlsoft (GCAGCTTCTGGCTTCACCTTC87855887 8TATATTAGCTGGGTGCGTCAG) (SEQ ID NO: 54) and G3CDRH2soft (GGCCTGGAATGGGTTGCT668ATT558CCT558668GGTTATACTTACTATGCCG) (SEQ ID NO: 55) and 20 µg of Kunkel DNA of the L3 stop template (described in Example 2A) were used to generate the library by Kunkel mutagenesis.

The L3/H3 library had positions 91-94, 96 (Kabat numbering) of the light chain and positions 98-100 and 100b (Kabat numbering) of the heavy chain soft randomized. The L3 mutagenic oligonucleotides F563-L3soft1 (SEQ ID NO: 51), F564-L3soft2 (SEQ ID NO: 52), and F565-L3soft3 (SEQ ID NO: 53) described above were mixed at a 1:0.5:1 ratio. Equal amounts of the L3 oligo mix and mutagenic oligonucleotide G3CDRH3soft (GTCTATTATTGTGCTCGT GAGTGGTAC888668668TAC688ATGGAC TACTGGGGTCAAGGAACC) (SEQ ID NO: 56) and 20 µg of Kunkel DNA of the L3/H3 stop template (described in Example 2A) were used to generate the library by Kunkel mutagenesis.

The L1/H3 library had positions 28-33 (Kabat numbering) of the light chain hard randomized to allow for amino acid diversity found at these positions within natural human antibodies and positions 98-100 and 100b (Kabat numbering) of the heavy chain soft randomized. The L1 mutagenic oligonucleotides F111-L1 (SEQ ID NO: 43) and F202-L1 (SEQ ID NO: 44) were mixed at a 1:2 ratio. Equal amounts of the L1 oligo mix and mutagenic oligonucleotide G3CDRH3soft (SEQ ID NO: 56) and 20 µg of Kunkel DNA of the L1 stop template (described in Example 2A) were used to generate the library by Kunkel mutagenesis.

The H2/H3 library had positions 50, 52 (but not 52a), 53, 54, 98-100, and 100b (Kabat numbering) of the heavy chain soft randomized. Equal amounts mutagenic oligonucleotides G3CDRH2soft and G3CDRH3soft (SEQ ID NOs: 55 and 56) and 20 µg of Kunkel DNA of the H3 stop template (described in Example 2A) were used to generate the library by Kunkel mutagenesis.

The H3 library had positions 98-100 and 100b (Kabat numbering) of the heavy chain soft randomized. The mutagenic oligonucleotide G3CDRH3soft (SEQ ID NO: 56) and 20 µg of Kunkel DNA of the H3 stop template (described in Example 2A) were used to generate the library by Kunkel mutagenesis.

The mutagenesis reactions were electroporated into electrocompetent XL1-Blue (Stratagene) *E. coli* and recovered in 25 mL of SOC medium for 45 minutes at 37° C. with shaking. Twenty microliters were removed and ten-fold serial dilutions were plated onto solid agar plates containing carbenicillin and grown overnight at 37° C. to determine the library size. The remaining culture was transferred to 500 mL of 2YT broth containing 50 µg/mL carbenicillin and $10^{10}$ phage/mL M13K07 helper phage. The cells were infected at 37° C. for one hour with shaking. 50 µg/mL of kanamycin was added and the cultures were grown for another seven hours at 37° C. with shaking. The temperature was then shifted to 30° C. and the cultures were grown for another 22 hours. The libraries each contained at least ~3.5×$10^{10}$ colony forming units (CFUs). The phage were purified from the culture supernatant by two rounds of precipitation with 1/5 volume of 20% polyethylene glycol (PEG)/2.5M NaCl.

C. Affinity Maturation Library Sorting

The "light chain" libraries underwent four rounds of sorting. Each of the four libraries was sorted separately in parallel through all four rounds using the following protocol. The first round was plate-based sorting with K11-linked diubiquitin immobilized on a 96-well Maxisorb immunoplate (NUNC). Plates were coated overnight at 4° C. with 5 µg/mL K11-linked diubiquitin (UC Berkeley) in 50 mM sodium carbonate buffer, pH 9.6. The coated plates were blocked with 200 µL/well of 2.5% milk in PBS containing 0.05% Tween 20 (PBST) for one hour at 25° C. with shaking. The phage libraries were diluted to an OD=2.0 in 2.5% milk in PBST and 30 µg/mL of monoubiquitin was added for counterselection. After one hour, the blocking buffer was removed and 100 µL/well of the phage was added and incubated at 25° C. for two hours with shaking. After binding, the plate was washed 20 times with PBST by manually filling the wells and dumping off the buffer between washes. Phage were eluted with 150 µL/well of 50 mM HCl/500 mM KCl for 30 minutes at 25° C. with shaking. The elution was neutralized with 150 µL/well of 1 M Tris, pH 7.5 and subsequently propagated in XL1-Blue (Stratagene) *E. coli* with the addition of M13K07 helper phage.

Amplified phage were used for additional rounds of selection against K11-linked diubiquitin in solution-based sorting. K11-linked diubiquitin (UC Berkeley) was biotinylated with a three-fold molar excess of EZ-Link Sulfo-NHS-biotin (Pierce Biotechnology). In the second sort, neutravidin (Pierce Biotechnology) was immobilized on a 96-well Maxisorb immunoplate (NUNC). Plates were coated overnight at 4° C. with 5 µg/mL neutravidin in 50 mM sodium carbonate buffer, pH 9.6. The coated plates were blocked with 200 µL/well of 2.5% milk in PBST for one hour at 25° C. with shaking. Phage from the first round of sorting were diluted to an OD=1.0 in 2.5% milk in PBST with 250 nM of biotinylated K11-linked diubiquitin (UC Berkeley) and 10 µg/mL each of monoubiquitin, linear diubiquitin, K48 polyubiquitin 2-7, and K63 polyubiquitin 2-7 (all from Boston Biochem) for counterselection. Phage were allowed to bind the biotinylated K11-linked diubiquitin in solution for two hours at 25° C. with rotation. After binding the phage were diluted five-fold in 2.5% milk in PBST and phage bound to the biotinylated K11-linked diubiquitin were captured on the neutravidin plates for 10 minutes at 25° C. with shaking. After capture, the plate was washed 30 times with PBST by manually filling the wells and removing the buffer between washes. Phage were eluted with 100 µL/well of 50 mM HCl/500 mM KCl for 30 minutes at 25° C. with shaking. The elution was neutralized with 100 µL/well of 1 M Tris, pH 7.5 and subsequently propagated in XL1-Blue (Stratagene) *E. coli* with the addition of M13K07 helper phage.

The stringency of the later sorts was increased in three ways: by decreasing the amount of biotinylated K11-linked diubiquitin used in the sort; by increasing the number and duration of plate washes; and by decreasing the duration of phage binding. The third sort was performed identically to the second sort described above, except the number of plate washes was increased to 40. The fourth sort was performed identically to the third sort, except the amount of biotinylated K11-linked diubiquitin was decreased to 100 nM, the binding time was decreased to one hour, and four additional plate washes were added. These washes were incubated at 25° C. for 15 minutes each with shaking. Enrichment was calculated for each round by comparing the number of phage recovered with K11-linked diubiquitin compared to an uncoated well for plate sorting or a neutravidin coated well for solution sorting. Enrichment was observed in all four rounds for all four libraries (see Table 3).

After four rounds of sorting 48 individual clones were picked from each of the four libraries (total of 192) and grown up in 96-well format in 1 mL of 2YT broth containing 50 µg/mL carbenicillin and $10^{10}$ phage/mL M13K07 helper phage. Supernatants from those cultures were used in high-throughput phage spot ELISAs for binding to K11-linked diubiquitin (UC Berkeley), monoubiquitin (Boston Biochem), linear diubiqutin (Boston Biochem), K48-linked polyubiquitin 2-7 (Boston Biochem), K63-linked polyubiquitin 2-7 (Boston Biochem), an anti-gD antibody (Genentech), or an uncoated well (as described in Example 1). Thirty-two clones were identified that demonstrated specific binding to K11-linked diubiquitin.

TABLE 3

Enrichment of K11-linked Polyubiquitin Binders During Affinity Maturation
Fold Enrichment

| Light Chain Library | Round 1 | Round 2 | Round 3 | Round 4 |
|---|---|---|---|---|
| L1 | 120 | 14 | 24 | 12 |
| L2 | 130 | 38 | 12 | 5 |
| L3 | 20 | 29 | 9 | 13 |
| L1/L2/L3 | 6 | 9 | 14 | 4 |

| Heavy Chain Library | Round 1 | Round 2 pool | Round 3 pool | Round 4 (5, 1, 0.5 nM) |
|---|---|---|---|---|
| L1/L2/L3hard | 19 | 21 | 6 | 6, 0, 0 |
| L3/H1/H2 | 47 | 21 | 6 | 6, 0, 0 |
| L3/H3 | 5 | 21 | 6 | 6, 0, 0 |
| L1/H3 | 140 | 21 | 6 | 6, 0, 0 |
| H2/H3 | 60 | 21 | 6 | 6, 0, 0 |
| H3 | 330 | 21 | 6 | 6, 0, 0 |

The "heavy chain" libraries underwent four rounds of sorting. Each of the four libraries were sorted in parallel for the first round and then pooled for sorts two through four. Plate-based sorting was used in the first round exactly as described above for the "light chain" libraries. Amplified phage were used in later rounds of sorting. Stringency of the later sorts was increased in four ways: by decreasing the amount of biotinylated K11-linked diubiquitin used in the sort; by increasing the number and duration of plate washes; by decreasing the duration of phage binding; and by adding excess unbiotinylated K11-linked diubiquitin to compete for phage binding before capturing with neutravidin. The second sort was solution-based and performed as described above for the "light chain" libraries except 100 nM biotinylated K11-linked diubiquitin was used and phage from all six libraries was pooled and sorted together. The third sort was performed as described for the "light chain" libraries except 10 nM biotinylated K11-linked diubiquitin was used and binding time was decreased to one hour. The fourth sort was performed as described above for the "light chain" libraries except three parallel sorts were done with 5 nM, 1 nM, and 0.5 nM biotinylated K11-linked diubiquitin. In addition, after one hour of phage binding and before capture with neutravidin, 30 µg/mL of unbiotinylated K11-linked diubiquitin (UC Berkeley) was added and allowed to compete for phage binding for 30 minutes at 25° C. with rotation to select for clones with slower off-rates. Enrichment was calculated for each round as described above. Enrichment was observed in all four rounds (see Table 3).

After four rounds of sorting 192 clones were picked and grown up in 96-well format in 1 mL of 2YT broth containing 50 µg/mL carbenicillin and $10^{10}$ phage/mL M13K07 helper phage. Supernatants from those cultures were used in high-throughput phage spot ELISAs for binding to K11-linked diubiquitin, monoubiquitin, linear diubiqutn, K48-linked polyubiquitin 2-7, K63-linked polyubiquitin 2-7, an anti-gD antibody, or an uncoated well (as described in Example 1). Twenty-three clones were identified that demonstrated specific binding to K11-linked diubiquitin. Single spot competition phage ELISAs were performed to determine which clones had the biggest improvement in affinity over the parental G3 clone. The phage supernatants from the phage spot ELISAs (Example 2C) were used. The competition ELISA was performed as described for the IC50 ELISA (Example 1B) except phage supernatants were used instead of purified Fab and only a single concentration (50 nM) of soluble K11-linked diubiquitin (Genentech) was used. The competition was also performed for each clone without the addition of any soluble K11-linked diubiquitin to determine the phage binding signal in the absence of any competing antigen. The percent inhibition in binding in the presence of 50 nM K11-linked diubiquitin was calculated as [1−($OD_{450}$ for 50 nM K11/$OD_{450}$ for no K11)]×100%. The G3 parental clone showed on average 33 percent inhibition of binding in the presence of 50 nM K11-linked diubiquitin (see Table 4). Clones showing 60 percent inhibition or greater were selected for further analysis.

TABLE 4

IC50 Values for Affinity-Matured and Parental Anti-K11-Linked Polyubiquitin Fabs

| Clone* | OD450 no K11 | OD450 50 nM K11 | % inhibition | Comments |
| --- | --- | --- | --- | --- |
| G3 parental | 1.716 | 1.239 | 27.80 | |
| G3 parental | 1.76 | 1.216 | 30.91 | |
| G3L1.1A3 | 1.378 | 0.579 | 57.98 | |
| G3L1.1A11 | 1.169 | 0.422 | 63.90 | |
| G3L1.1C12 | 1.205 | 0.454 | 62.32 | |
| G3L2.1F12 | 1.143 | 0.446 | 60.98 | |
| G3L3.1B3 | 1.326 | 0.657 | 50.45 | |
| G3L1L2L3.1G12 | 1.596 | 1.071 | 32.89 | |
| G3HC.1B1 | 1.455 | 0.866 | 40.48 | G3 parental sequence |
| G3HC.1C1 | 1.538 | 0.993 | 35.44 | G3 parental sequence |
| G3HC.1C4 | 1.399 | 0.766 | 45.25 | |
| G3HC.1C9 | 1.342 | 0.978 | 27.12 | G3 parental sequence |
| G3HC.1D2 | 1.621 | 0.82 | 49.41 | |
| G3HC.2A3 | 0.792 | 0.15 | 81.06 | sib with 2E1 |
| G3HC.2A6 | 1.423 | 0.308 | 78.36 | sib with 2B4, 3G9 |
| G3HC.2A11 | 1.279 | 0.74 | 42.14 | |
| G3HC.2B4 | 1.809 | 0.781 | 56.83 | sib with 2A6, 3G9 |
| G3HC.2C8 | 1.486 | 0.968 | 34.86 | G3 parental sequence |
| G3HC.2C11 | 1.668 | 0.87 | 47.84 | sib with 2D7, 2H10, 3C6 |
| G3HC.2D7 | 1.368 | 0.485 | 64.55 | sib with 2C11, 2H10, 3C6 |
| G3HC.2D8 | 1.643 | 0.7 | 57.40 | |
| G3HC.2E1 | 0.807 | 0.166 | 79.43 | sib with 2A3 |
| G3HC.2E6 | 1.402 | 0.54 | 61.48 | |
| G3HC.2F10 | 1.753 | 0.947 | 45.98 | |
| G3HC.2G4 | 1.274 | 0.382 | 70.02 | sib with 3C12 |
| G3HC.2H5 | 1.387 | 0.569 | 58.98 | |
| G3HC.2H10 | 1.345 | 0.717 | 46.69 | sib with 2C11, 2D7, 3C6 |
| G3HC.3A4 | 1.425 | 0.801 | 43.79 | |
| G3HC.3C6 | 1.543 | 0.672 | 56.45 | sib with 2C11, 2D7, 2H10 |
| G3HC.3C12 | 1.24 | 0.309 | 75.08 | sib with 2G4 |
| G3HC.3D10 | 1.407 | 0.924 | 34.33 | G3 parental sequence |
| G3HC.3E2 | 1.496 | 0.78 | 47.86 | |
| G3HC.3F3 | 1.372 | 0.927 | 32.43 | G3 parental sequence |
| G3HC.3F12 | 1.204 | 0.725 | 39.78 | |
| G3HC.3G9 | 1.245 | 0.284 | 77.19 | sib with 2A6, 2B4 |
| G3HC.3H2 | 1.281 | 0.612 | 52.22 | |

*Clone names beginning with "G3L1", "G3L2", "G3L3", or "G3L1L2L3" indicate which "light chain" CDR affinity maturation libraries they came derived from. Clone names beginning with "G3HC" indicate that they came from the pooled "heavy chain" affinity maturation libraries.

D. Sequencing Affinity-Matured Clones

Both the light and heavy chains of the highest affinity clones identified in the single spot competition phage ELISA (example 2C) were sequenced. A total of eight unique affinity matured clones were identified (see FIGS. 4A and 4B) along with several identical siblings (see Table 4). Clones G3L1.1A11, G3L1.1C12, G3HC.2A3, and G3HC.2G4 contained mutations only within CDR L1. Clones G3HC.2A6 and G3HC.2D7 contained mutations within CDR H3. G3L2.1F12 contained mutations within CDR L2, including an amber stop codon that could be substituted with a glutamine when expressed in an amber suppressor strain such as the XL1-Blue *E. coli* that was used in this phage sorting. Clone G3HC.2E6 contained mutations only within CDR H2.

The consensus amino acid sequences of the light chain HVR regions that displayed variability in the above clones were: HVR L1: X22 X23 Ser X24 X25 X26 X27 X28 X29 X30 X31 (SEQ ID NO: 73), wherein X22 is selected from arginine and glycine, X23 is selected from alanine and valine, X24 is selected from glutamine and histidine, X25 is selected from aspartic acid, asparagine and isoleucine, X26 is selected from leucine and valine, X27 is selected from serine, aspartic acid, glycine and glutamic acid, X28 is selected from threonine and serine, X29 is selected from alanine, valine and phenylalanine, X30 is selected from valine and isoleucine, and X31 is selected from alanine and serine; and HVR L2: X32 X33 X34 Phe X35 Tyr Ser (SEQ ID NO: 74), wherein X32 is selected from serine and asparagine, X33 is selected from glutamine and alanine, X34 is selected from glutamic acid and serine, and X35 is selected from leucine and valine.

The consensus amino acid sequences of the heavy chain HVR regions that displayed variability in the above clones were: HVR H2: X36 Ile Asn Pro X37 Gly Gly Tyr Thr Tyr Tyr Ala Asp Ser Val Lys Gly (SEQ ID NO: 75), wherein X36 is selected from alanine and glycine and X37 is selected from alanine and asparagine; and HVR H3: Glu Trp Tyr X38 X39 Gly Tyr Val Met Asp Tyr (SEQ ID NO: 76), wherein X38 is selected from phenylalanine and tyrosine and X39 is selected from glycine and aspartic acid.

E. Phage Specificity ELISA

Figure 5A:
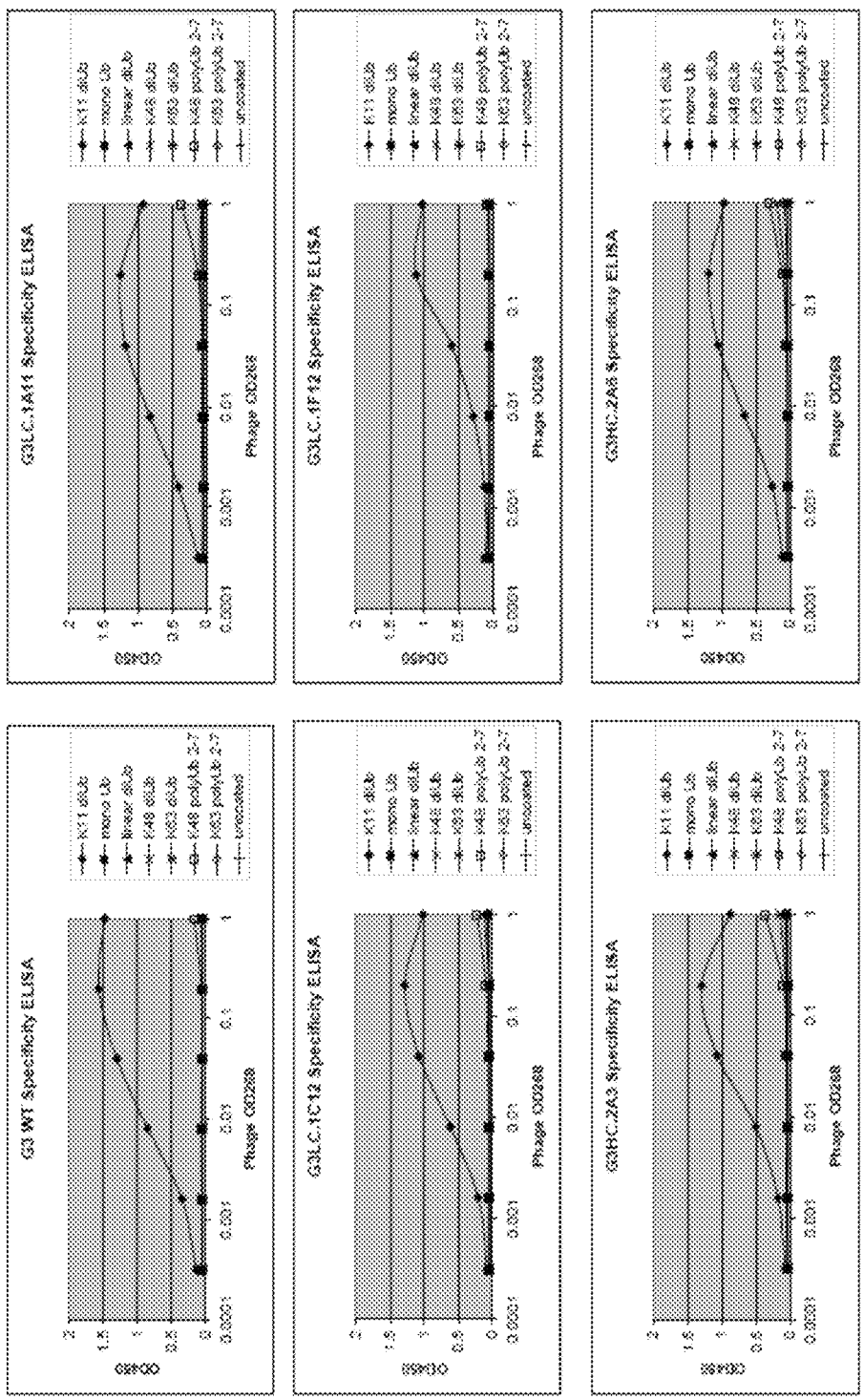
FIGS. 5A-5B depict the results of ELISA experiments performed to assess the binding of the parental G3 clone and the eight affinity-matured variants displayed on phage for binding to a panel of ubiquitin proteins, as described in Example 2E.
Figure 5B:
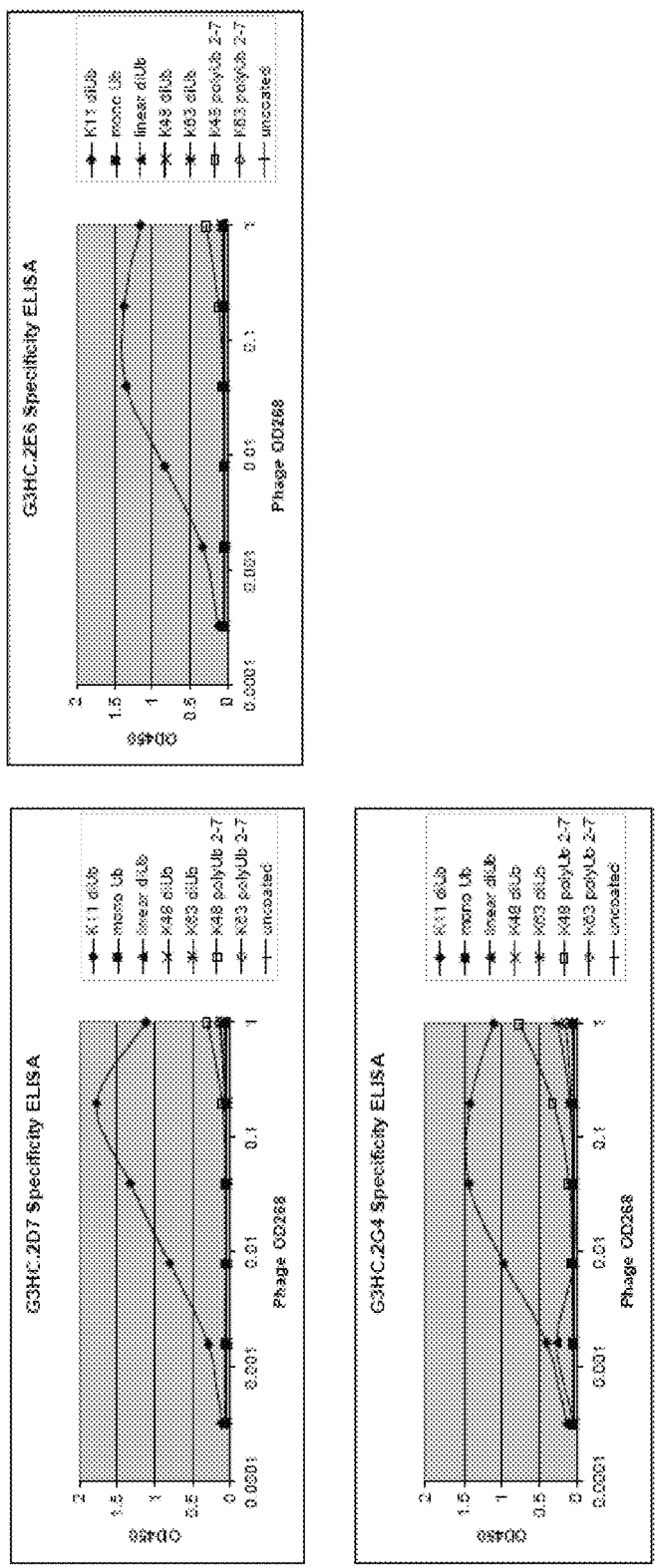

The specificity of the eight affinity matured clones for polyubiquitins of different linkages was assessed by phage ELISA. The phage ELISAs were performed as described in Example 1 except that instead of phage supernatants, six five-fold serial dilutions of purified phage starting at $OD_{268}$=1.0 were used. All of the affinity matured clones bound K11-linked diubiquitin in a phage concentration-dependent manner (FIG. 5). Only very weak binding to K48-linked polyubiquitin was seen at the highest phage concentration tested.

F. Fab Production, Affinity Analysis, and Hybrid Generation

The G3 parental and eight affinity matured Fab variable domains were cloned into a Fab expression plasmid lacking the gD tag on the light chain constant domain. In addition, the amber stop (TAG) within CDR L2 of clone G3L2.1F12 was mutated to CAG to encode glutamine. Mutagenic oligonucleotides 5'-G3LC1F12stopQ (CCGAAGCTTCT-GATTTACAACCAGGAA TTCGTGTACAGCGGAGTC) (SEQ ID NO: 77) and 3'-G2LCF12stopQ (GACTCCGCT-GTA CACGAATTCCTGGTTGTAAATCAGAAGCT-TCGG) (SEQ ID NO: 78) were used to replace the TAG codon with a CAG codon using the QuikChange® Lightning Site-Directed Mutagenesis kit (Stratagene). The resulting plasmids were transformed into *E. coli* strain 64B4 (Genentech), expressed as soluble Fabs, and purified using Protein A-sepharose as described in Example 1. Purified Fabs were used in SPR experiments to determine their affinities as described in Example 1 using the same chip. All eight clones showed improved dissociation constants ($K_D$) for K11-linked diubiquitin relative to the parental molecule and no detectable binding to either K48-linked or K63-linked diubiquitin (see Table 2).

The highest affinity clones with mutations in the light chain were G3L1.1C12 and G3HC.2A3, with dissociation constants of 35 nM and 25 nM, respectively. Both contained only CDR L1 changes (see FIGS. 4A and 4B), and improvements in both the on rates ($k_a$) and the off rates ($k_d$) (see Table 2) relative to the parental G3 clone were observed. The highest affinity clone with mutations in the heavy chain was G3HC.2E6, with a dissociation constant of 47 nM. This clone contained only CDR H2 changes, and only off rate improvement was observed.

Due to the affinity maturation library designs described in Example 2B there was no combination of CDR mutants that would have allowed both CDR L1 and CDR H2 changes. Therefore hybrid Fab phagemids were generated using standard restriction digest cloning methods which combined the light chain of G3L1.1C12 and the heavy chain of G3HC.2E6 (resulting in clone 1C12/2E6) or the light chain of G3HC.2A3 and the heavy chain of G3HC.2E6 (resulting in clone 2A3/2E6) (see FIGS. 6A and 6B). These hybrids were also expressed as soluble Fabs, purified, and analyzed by SPR as described in Examples 1C and 1D. The combinations of these heavy and light chains resulted in additive affinity improvements (see Table 2). Both 1C12/2E6 and 2A3/2E6 had dissociation constants of 12 nM for K11-linked diubiquitin corresponding to nearly a nine-fold improvement in affinity compared to the G3 parental Fab, which was due to both improvements in on and off rates for both hybrids. In addition, neither 1C12/2E6 nor 2A3/2E6 demonstrated detectable binding to either K48-linked or K63-linked diubiquitin.

G. Conversion to IgG Format and Affinity Analysis

The parental Fab (G3) and the two affinity-matured hybrid Fabs (1C12/2E6 and 2A3/2E6) were expressed in 293 cells as human immunoglobulins (IgGs). Expression constructs were generated by cloning the Fab variable domains into pRK mammalian expression constructs encoding the heavy and light chains of human kappa IgG1 (Gorman et al., DNA Prot. Eng. Tech. 2:3-10 (1990)). IgGs were purified by affinity chromatography on protein A-sepharose columns by standard methodologies (as described for the Fab purification in Example 1) and buffer-exchanged into PBS using PD10 desalting columns (GE Healthcare).

The affinities of the hybrid Fabs were initially determined by SPR using amine coupling of the antigen directly on a CM5 chip (Example 2F). This involved the primary amines of available lysine side chains on the antigen. Lysines involved in isopeptide bonds linking two ubiquitin monomers together to form diubiquitin would be unavailable for coupling. Since K11, K48, and K63-linked diubiquitin have different lysine residues participating in the isopeptide bond, the lysines available for coupling to the chip are also different and therefore different epitopes may be available or unavailable for antibody binding, accordingly.

To avoid potentially confounding effects of lysines coupled to the chip, the affinities of the IgGs generated in this example were tested in SPR using an IgG capture method on a BIACORE™ 3000 (GE Healthcare). Approximately 11,500 resonance units (RUs) of an anti-human Fc capture antibody (GE Healthcare) were immobilized on flow cells one and two of a CM5 chip using the amine coupling protocol supplied by the manufacturer. Sixty µL of 0.5 µg/mL IgG in 10 mM Hepes, pH 7.2, 150 mM NaCl, and 0.01% Tween 20 (HBST) was injected at a flow rate of 30 µL/minute over flow cell two, resulting in capture of approximately 800 RUs of IgG. Flow cell one had only the capture antibody on it to serve as a reference subtraction. Two-fold serial dilutions (0.5-500 nM) of K11-linked diubiquitin (Genentech), K48-linked diubiquitin (Boston Biochem), or K63-linked diubiquitin (Boston Biochem) in HBST were injected (60 µL total at a flow rate of 30 µL/minute) over flow cells one and two. The signal for each flow cell was recorded and the reference signal was subtracted. Following a dissociation period of four minutes, the chip surface was regenerated with 15 µL of 3M $MgCl_2$. Data were fit to a 1:1 binding model with mass transfer for the G3 IgG or a 1:1 binding model with drifting baseline for 1C12/2E6 and 2A3/2E6 IgGs. Kinetic constants and binding constants were simultaneously calculated by nonlinear regression analysis, using software provided by the manufacturer, and are shown in Table 5.

The G3 IgG had a $K_D$ for binding K11 diubiquitin of 129 nM, whereas both the 1C12/2E6 and 2A3/2E6 IgGs bound with a $K_D$ of 20 nM. These affinities were consistent and within the acceptable two-fold range of error of the binding constants measured for the same Fabs using the direct coupling of antigen method (see Table 2). In addition, no detectable binding to K48-linked diubiquitin or K63-linked diubiquitin was observed.

TABLE 5

SPR Binding of hybrid IgGs to Polyubiquitin Molecules of Different Lysine Linkages

| IgG | ka (1/Ms) | K11 DiUb kd (1/s) | KD (nM) | K48 DiUb | K63 DiUb |
|---|---|---|---|---|---|
| G3 WT | 7.95E+05 | 1.03E−01 | 129 | NDB | NDB |
| 1C12/2E6 | 4.00E+05 | 7.83E−03 | 20 | NDB | NDB |
| 2A3/2E6 | 5.03E+05 | 1.03E−02 | 20 | NDB | NDB |

NDB = no detectable binding observed

Example 3

Characterization of the Affinity Matured Hybrid Anti-K11 Antibodies

A. IgG Specificity ELISAs

The specificity of the G3 parental, 1C12/2E6, and 2A3/2E6 IgGs were tested for binding to a panel of ubiquitin proteins by ELISA. K11-linked diubiquitin (Genentech), monoubiquitin, linear diubiquitin, K48-linked diubiquitin, K63-linked diubiquitin, K48-linked polyubiquitin, K63-linked polyubiquitin (all from Boston Biochem) were immobilized on 96-well Maxisorb immunoplates. Plates were coated at 25° C. for two hours with 1 µg/mL of each protein in 50 mM sodium carbonate buffer, pH 9.6 with shaking. The coated plates were blocked with 200 µL/well of 2.5% milk in PBST for one hour at 25° C. with shaking. Eleven two-fold serial dilutions of the G3 parental, 1C12/2E6, and 2A3/2E6 IgGs were made in 2.5% milk in PBST from 20 µg/mL to 0.02 µg/mL. After one hour, the blocking buffer was removed and 100 µL/well of each IgG dilution was added and incubated at 25° C. for one hour with shaking. The plate was then washed six times with PBST using a plate washer. A 1:5,000 dilution of a goat anti-human Fcγ-specific HRP-conjugated F(ab')2 secondary antibody (Jackson Immunoresearch) in PBST was used for detection of IgG binding. One hundred µL/well of the secondary antibody dilution was added and the plate was incubated at 25° C. for 30 minutes with shaking. The plate was then washed 12 times with PBST using a plate washer and twice with PBS manually. Bound secondary antibody was detected using a TMB substrate (KPL) followed by quenching with an equal volume of 1 M phosphoric acid. The absorbance was read at 450 nm. All three IgGs recognized K11-linked diubiquitin, even at very low concentrations of IgG. Approximately the same signal for K11-linked diubiquitin binding was observed for G3, 1C12/2E6, and 2A3/2E6 at each IgG concentration, despite the fact that there is a seven to nine-fold difference in affinity between them. Thus, this ELISA format was not able to distinguish between the affinities of the parental IgG and the affinity matured variants. In addition, at low IgG concentrations all three IgGs were highly specific, however, upon increasing the IgG concentration towards 20 μg/mL, some limited nonspecific binding to K48-linked polyubiquitin, K63-linked diubiquitin, and K63-linked polyubiquitin could be seen for both 1C12/2E6 and 2A3/2E6 in this assay format.

Figure 7A:
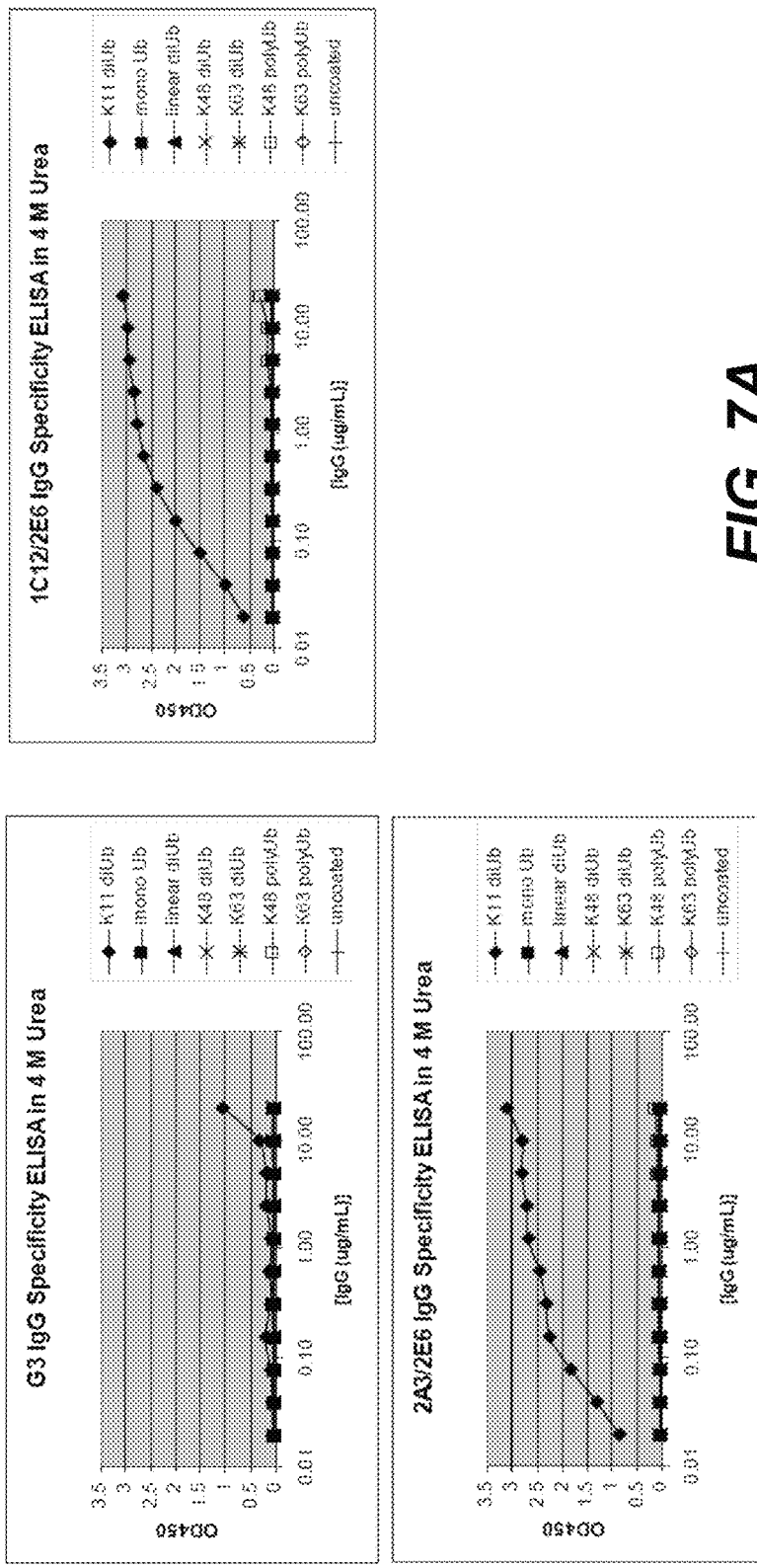
FIGS. 7A-7D depict the results of studies assessing the binding characteristics of the hybrid IgGs in comparison to the parental G3 clone and controls, as described in Example 3.

To identify a more stringent condition that would allow one to distinguish between the affinities of the different IgGs and provide more specific recognition of K11-linked diubiquitin in this assay format, the ELISAs were performed again in a buffer containing 4 M urea (4 M urea, 20 mM Tris, pH 7.5, 135 mM NaCl, 1% Triton X-100, 10% glycerol, 1 mM EDTA, 1.5 mM $MgCl_2$). Under these stringent conditions, very little binding to K11-linked diubiquitin was observed for the G3 parental IgG, except at the highest concentration of IgG tested (20 μg/mL) (FIG. 7A). In contrast, for the affinity matured variants 1C12/2E6 and 2A3/2E6, strong binding was seen at all concentrations, including the lowest IgG concentration of 0.02 μg/mL. In addition, the use of 4 M urea buffer allows a high degree of specificity for K11-linked diubiquitin to be maintained. Only 1C12/2E6 showed very weak binding to K48-linked polyubiquitin at the highest concentration of IgG tested. 2A3/2E6 shows no binding to any of the ubiquitin forms other than K11-linked diubiquitin, even at the highest concentration of IgG tested (20 μg/mL). Therefore, under these stringent conditions an increased affinity translates to increased function of the antibodies in the ELISA.

B. IgG Western Blot Analyses

The G3 parental, 1C12/2E6, and 2A3/2E6 IgGs were first tested for their ability to detect pure diubiquitin chains in a western blot. Seven two-fold serial dilutions of K11-linked diubiquitin (Genentech) from 1 μg to 15 ng and 1 μg each of monoubiquitin, linear diubiquitin, K48-linked diubiquitin, and K63-linked diubiquitin (all from Boston Biochem) in 1×LDS buffer (Invitrogen) were heated at 70° C. for ten minutes and run on 4-12% Bis Tris NuPAGE 1.0 mm gels (Invitrogen) under non-reducing conditions in MES buffer (Invitrogen) in quadruplicate. One gel was stained by Coomassie to detect all proteins. The other three gels were transferred at 30 V constant for one hour by wet transfer in 10% methanol and 1×NuPAGE transfer buffer (Invitrogen) to 0.2 μm nitrocellulose (Invitrogen). Non-specific binding sites on the membranes were blocked by incubation in 5% milk in PBST for one hour at 25° C. with shaking. The membranes were then incubated in 1 μg/mL of G3, 1C12/ 2E6, or 2A3/2E6 IgG in 5% milk in PBST for one hour at 25° C. with shaking. The membrane was washed three times in PBST with shaking. The IgGs were detected by incubating the membrane in a 1:10,000 dilution of a goat anti-human Fcγ-specific HRP-conjugated F(ab')2 secondary antibody (Jackson Immunoresearch) in 5% milk in PBST for one hour at 25° C. with shaking. The membrane was then washed three times in PBST followed by one wash in PBS. The secondary antibody was detected using Super Signal West Pico chemiluminescent substrate (Pierce Biotechnology) followed by exposure of the blots to film.

Figures 7B, 7C:
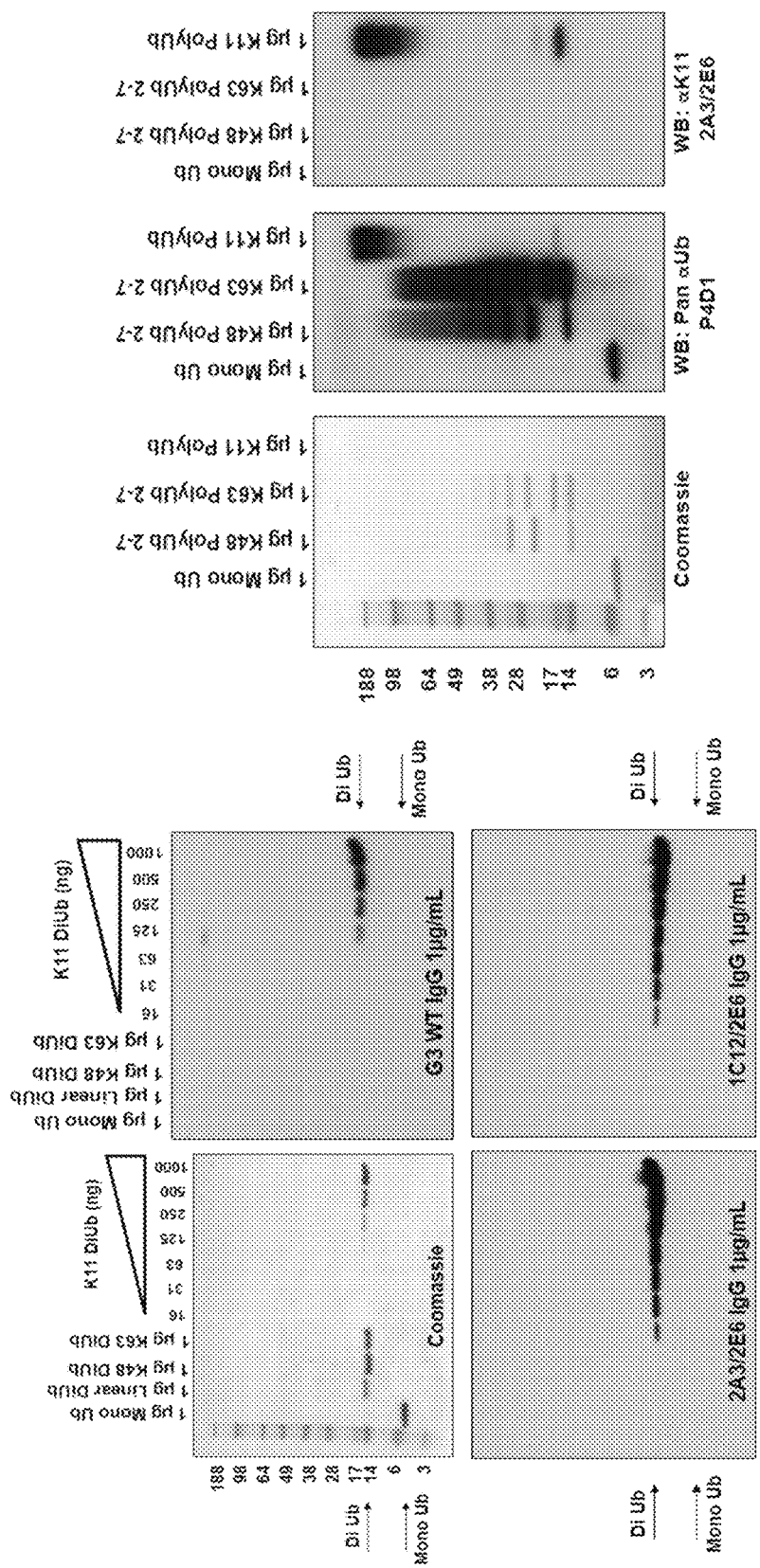

All three IgGs detected only K11-linked diubiquitin but not monoubiquitin, linear diubiquitin, K48-linked diubiquitin, or K63-linked diubiquitin, indicating that they are highly specific for K11-linked diubiquitin in a western blot context (see FIG. 7B). In addition, the affinity matured variants were much more sensitive than the G3 parental IgG in that they were able to detect as little as 15 ng of K11-linked diubiquitin, whereas the G3 IgG limit of detection was 125 ng in this particular blot exposure. Therefore, the approximately seven to nine-fold improvement in affinity of the hybrids over the parental antibody translated into improved function in a western blot in recognition of K11-linked diubiquitin. Despite increased affinity for the desired antigen, specificity is maintained and there was no detectable binding of either 1C12/2E6 or 2A3/2E6 IgG to any of the other ubiquitin forms tested. Since the 1C12/2E6 and 2A3/2E6 affinity-matured variants behaved identically in SPR analysis, specificity IgG ELISAs and western blots for diubiquitin described above, only 2A3/2E6 was used in further testing.

The K11 linkage-specific antibodies were generated against a K11-linked diubiquitin antigen so they presumably recognized either the linkage itself, or more likely, the surrounding surface residues on the donor and acceptor ubiquitins that are placed in close proximity due to the conformation of diubiquitin which results from the K11 linkage. Since diubiquitin is the smallest recognition unit of antigen and K11-linked polyubiquitin is a polymer chain with diubiquitin as the repeating "monomer" unit, the antibodies should also bind longer polyubiquitin chains joined by K11 linkages. To examine this, the 2A3/2E6 IgG was tested for its ability to detect pure polyubiquitin chains in a western blot. 1 μg each of monoubiquitin (Boston Biochem), K48-linked polyubiquitin 2-7 (Boston Biochem), K63-linked polyubiquitin 2-7 (Boston Biochem), and K11-linked polyubiquitin (Genentech) in 1×LDS buffer (Invitrogen) with reducing agent was heated at 70° C. for ten minutes and run on 4-12% Bis Tris NuPAGE 1.0 mm gels (Invitrogen) under reducing conditions in MES buffer (Invitrogen) in triplicate. One gel was stained by SimplyBlue coomassie stain (Invitrogen) to detect all proteins. The remainder of the western blot was performed as above, except that the transfer to 0.45 μm nitrocellulose (Invitrogen) was performed at 30V for two hours. Whereas the control pan-ubiquitin antibody, P4D1, recognized monoubiquitin, K48-linked polyubiquitin 2-7, K63-linked polyubiquitin 2-7, and K11-linked polyubiquitin, the 2A3/2E6 IgG recognized only K11-linked polyubiquitin (see FIG. 7C). Thus, just as with K11-linked diubiquitin, the 2A3/2E6 antibody can detect polyubiquitin chains containing the K11 linkage, but does not recognize polyubiquitin chains of other linkages.

Since the 2A3/2E6 antibody could specifically bind to pure K11-linked polyubiquitin chains the 2A3/2E6 IgG was next tested for its ability to detect K11-linked polyubiquitin chains from both mammalian and yeast whole cell lysates. 293T cells were grown in high glucose Dulbecco's Modified Eagle Media (DMEM) supplemented with 10% fetal bovine serum (FBS) and 2 mM L-glutamine. Cells were scraped from the plates, spun down at 2000 rpm for ten minutes at 4° C., washed with 20 mL of cold PBS, and repelleted. Cells were lysed in buffer containing 8 M urea, 50 mM Tris, pH 7.5, and 25 mM NaCl, 10 μL/mL of 100× Halt protease and phosphatase inhibitors (Pierce Biotechnology), 5 mM EDTA (Pierce Biotechnology), and 2 mM N-ethylmalemide (NEM, Pierce Biotechnology) and then briefly sonicated to reduce the viscosity. The lysate was diluted two-fold to 4 M urea in immunoprecipitation (IP) buffer (20 mM Tris, pH 7.5, 135 mM NaCl, 1% Triton X-100, 10% glycerol, 1 mM EDTA, 1.5 mM $MgCl_2$). *Saccharomyces cerevisiae* strain YRG-2 (Stratagene) was grown in YEPD media at 30° C. overnight. 18 mL of cells were pelleted at 3000 rpm for 5 minutes, washed in water, and repelleted resulting in a 400 mg cell pellet. Cells were lysed according to the manufacturer's instructions in 1 mL of Y-PER (Pierce Biotechnology) supplemented with 25 μM MG132 (Cayman Chemical), 2 mM NEM (Pierce Biotechnology, 1 mM PMSF (Calbiochem), and 5 mM dithiolthreitol (DTT).

Figure 7D:
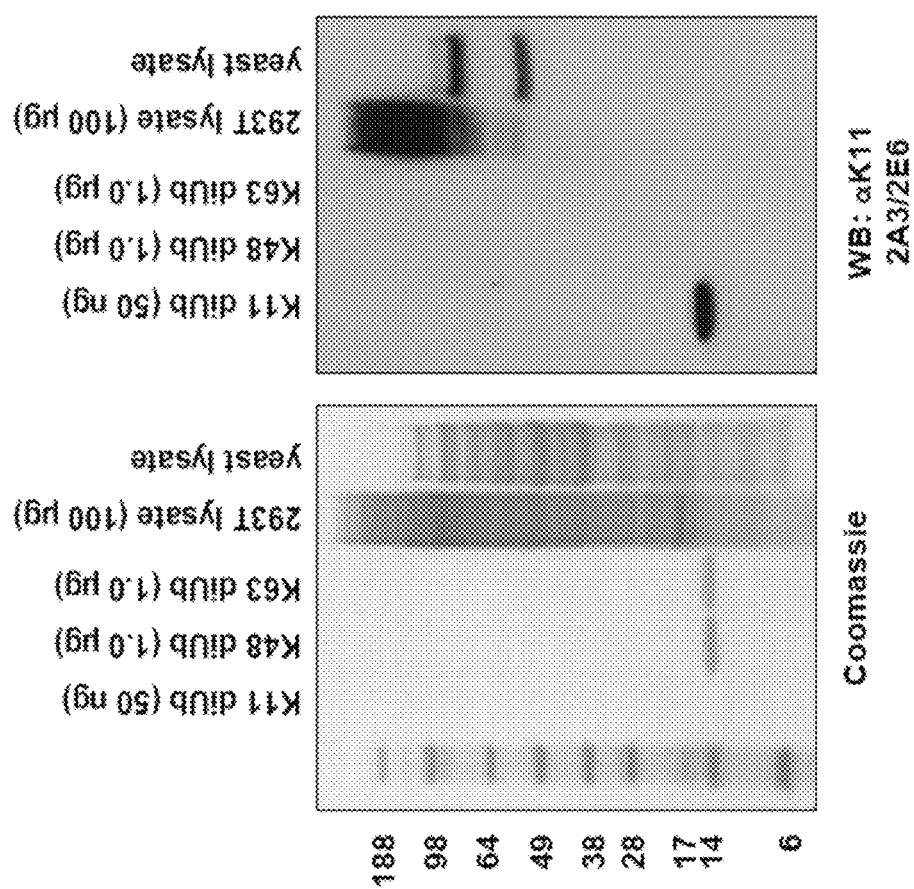

Fifty nanograms of K11-linked diubiquitin (Genentech), 1 μg of K48-linked diubiquitin (Boston Biochem), 1 μg of K63-linked diubiquitin (Boston Biochem), 100 μg of total protein from the 293T cell lysate, and 22 μL of the *S. cerevisiae* cell lysate in 1×LDS buffer (Invitrogen) with reducing agent was heated at 70° C. for ten minutes and run on 4-12% Bis Tris NuPAGE 1.0 mm gels (Invitrogen) under reducing conditions in MES buffer (Invitrogen) in duplicate. The gel transfer and western blots were performed as described above, except that the transfer to 0.45 μm nitrocellulose (Invitrogen) was performed at 30V for two hours. The 2A3/2E6 IgG detected the positive control, K11-linked diubiquitin, but neither of the negative controls, K48-linked diubiquitin or K63-linked diubiquitin (FIG. 7D). In addition, 2A3/2E6 was able to recognize a high molecular weight smear characteristic of polyubiquitination from the 293T cell lysate as well as several high molecular weight bands from the yeast cell lysate. Thus, this IgG also was capable of detecting K11-linked polyubiquitin chains from whole cell lysates.

C. Immunoprecipitation of Autoubiquitinated MuRF1

To further characterize the specificity of the antibody and determine whether it could be used for immunoprecipitations (IPs), a MuRF1 autoubiquitination reaction was used to generate a pure substrate modified with polyubiquitin chains of multiple linkages. MuRF1 is an E3 ubiquitin ligase that is known to autoubiquitinate itself in the absence of substrate with K11-linked, K48-linked, and K63-linked polyubiquitin chains when combined with the E1 ubiquitin-activating enzyme, Ube1 and the E2 ubiquitin-conjugating enzyme, UbcH5c (Kim, H. T. et al. 2007 JBC 282:17375-86). Autoubiquitination reactions were carried out with 100 nM recombinant human $His_6$-Ube1 (Boston Biochem), 5 μM recombinant human UbcH5c (Boston Biochem), 1 μM recombinant human $His_6$-MuRF1 (Boston Biochem), 100 μM recombinant human ubiquitin (Boston Biochem), 20 mM Tris, pH 7.5, 20 mM KCl, 5 mM $MgCl_2$, 2 mM adenosine triphosphate (ATP), and 1 mM DTT in a total volume of 40 μL at 37° C. for 1.5 hours. The reactions were performed with both wild-type ubiquitin as well as K11R mutant ubiquitin (Boston Biochem) to prevent the formation of K11-linked chains in order to probe the specificity of the antibody. Six microliters of each reaction was diluted 100-fold with IP buffer (20 mM Tris, pH 7.5, 135 mM NaCl, 1% Triton X-100, 10% glycerol, 1 mM EDTA, 1.5 mM $MgCl_2$) containing 4 M, 2 M, 1 M, 0.5 M, or 0 M urea. Each IP reaction was precleared with 50 μL of Protein A Dynabeads (Invitrogen) at 25° C. for one hour with rotation. Beads were captured with a magnet and supernatants were transferred to new tubes. Twenty micrograms of 2A3/2E6 IgG was added to each IP and incubated at 25° C. overnight with rotation. The next day the IgG was captured with 100 μL of Protein A Dynabeads per IP by incubating at 25° C. for 15 minutes with rotation. Beads were captured and washed three times with 1 mL of lysis buffer containing the appropriate amount of urea and then twice with 1 mL of PBS, capturing between each wash. During the final wash the beads were transferred to a new tube. The IP material was eluted by resuspending the beads in 20 μL of 1×LDS sample buffer (Invitrogen) with reducing agent and incubating at 70° C. for ten minutes.

Figures 8A, 8B, 8C:
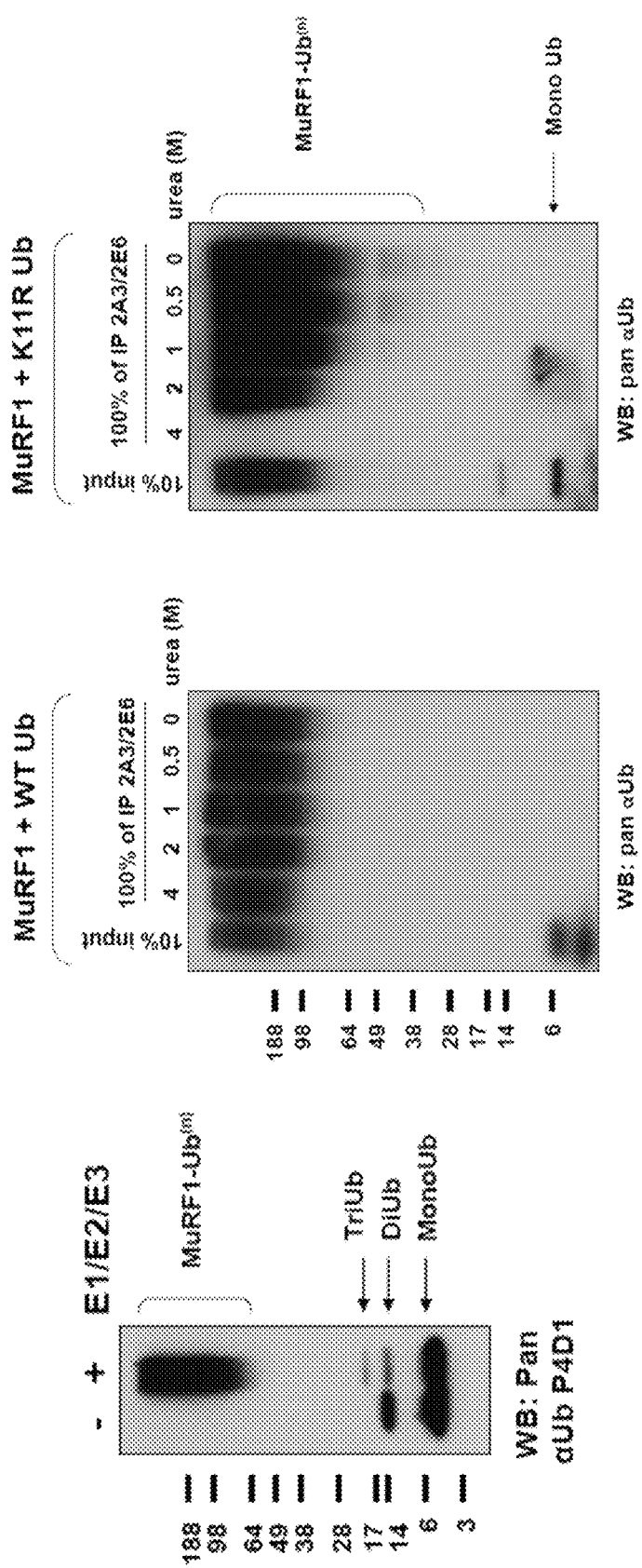
FIGS. 8A-8E show the results of experiments testing the ability of hybrid antibody 2A3/2E6 to specifically recognize and/or immunoprecipitate K11-linked polyubiquitinated proteins from in vitro ubiquitination reactions.

Ten percent of each input reaction and 100% of the IP material was run on 4-12% Bis Tris NuPAGE 1.0 mm gels (Invitrogen) under reducing conditions in MES buffer (Invitrogen). Western blots were carried out as described above with the pan-ubiquitin P4D1 antibody. The results demonstrated that under all tested concentrations of urea, the 2A3/2E6 antibody was capable of immunoprecipitating the autoubiquitinated MuRF1 when wild-type ubiquitin was used in the autoubiquitination reaction (FIGS. 8A and 8B). In addition, no IP of residual monoubiquitin present in the input lane was seen.

When K11R mutant ubiquitin is used it blocks the ability of MuRF1 to generate K11-linked polyubiquitin chains; however, the autoubiquitination still generates K48-linked and K63-linked chains. Therefore, one would expect that if the 2A3/2E6 IgG is specific for K11-linked chains then no IP of autoubiquitinated MuRF1 should be observed when K11R mutant ubiquitin is used. Indeed this was the case when the IP was performed in the presence of 4 M urea, indicating that the 2A3/2E6 IgG is highly specific for K11-linked chains under those conditions (FIG. 8C). This specificity was lost when the urea concentration is reduced to 2 M. This is consistent with the increased specificity seen with 4 M urea in the ELISAs shown in Example 3A as well as the specificity seen under 4 M urea in IPs with other ubiquitin linkage-specific antibodies generated against the K48 and K63 linkages (see, e.g., the antibodies described in published patent application US20070218069).

To further probe the specificity of the IgG in IPs, four MuRF1 autoubiquitination reactions were performed using recombinant human wild-type, K11R mutant, K48R mutant, and K63R mutant ubiquitin (Boston Biochem) as described above. Use of the lysine to arginine mutants prevents polyubiquitin linkages from being formed through those specific lysines. The four reactions were then split and equal portions were subjected to IP by the 2A3/2E6 IgG and a human kappa IgG1 isotype control antibody that does not specifically bind to any form of ubiquitin (Genentech). The input material from each autoubiquitination reaction, as well each immunoprecipitated sample were separated by parallel SDS-PAGE gels for Coomassie staining and western blot analysis with the pan-ubiquitin P4D1 antibody as described above.

Figures 8D, 8E:
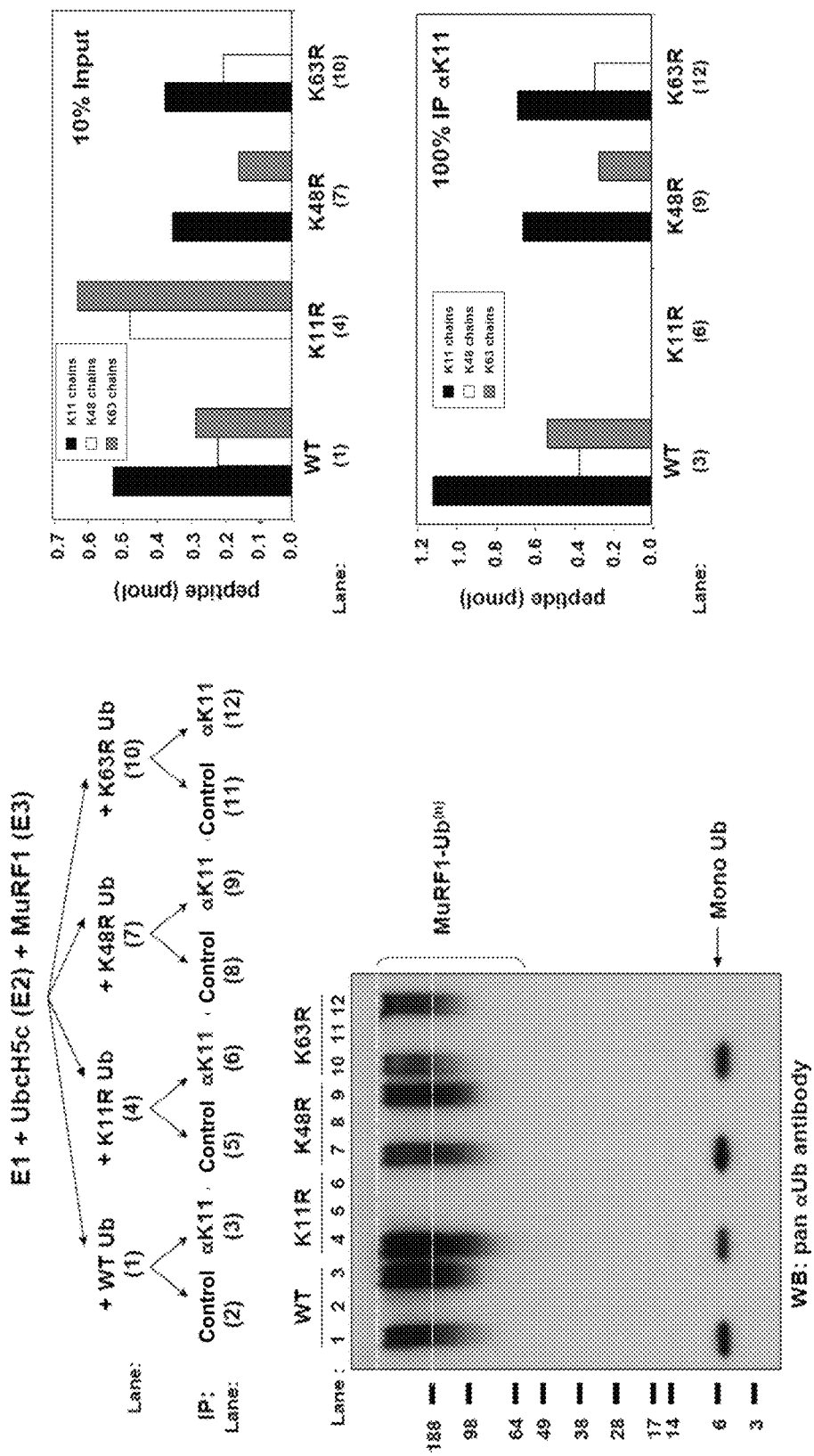

As shown in FIG. 8D the 2A3/2E6 IgG was able to IP autoubiquitinated MuRF1 only when K11-linked chains were present (when wild-type, K48R, or K63R mutant ubiquitin was used). When the K11R mutant ubiquitin used MuRF1 was not able to assemble K11-linked chains (see mass spectrometry confirmation below), and the 2A3/2E6 IgG was unable to IP any autoubiquitinated MuRF1 under those conditions. In contrast, the isotype control antibody was unable to IP any autoubiquitinated MuRF1 from any of the four autoubiquitination reactions.

Guided by the pan-ubiquitin western blot signal, mass spectrometry analysis was performed on the high molecular weight gel region (>188 kDa). Briefly, the portion of the gel corresponding to this region was excised and subjected to in-gel tryptic digestion. Gel pieces were destained using 50 mM ammonium bicarbonate/50% methanol and then desiccated with acetonitrile (ACN). To permit effective uptake of trypsin, gel pieces were incubated on ice for 2 hours with 20 ng/μL modified sequencing grade trypsin (Promega) diluted in 50 mM ammonium bicarbonate/5% ACN. Digests were performed overnight at 37° C. and stopped by the addition of 50% ACN/5% formic acid (FA). Isotope-labeled internal standard peptides (1 pmol) were added to each sample prior to two rounds of extraction. Extracted peptides were dried completely, and resuspended in 10% ACN/5% FA/0.01% hydrogen peroxide at least 30 minutes prior to mass spectrometric analysis. Samples were loaded directly onto a Thermo AQUASIL C18 column (2.1×150 mm) and separated using an Agilent 1200 capillary LC at a flow rate of 200 µL/min over a 26 minute gradient of 5% to 90% buffer B (98% ACN/0.1% FA). Mass spectrometric detection was performed on an ABI 4000 QTRAP using a segmented multiple reaction monitoring (MRM) method for detecting both labeled and unlabeled peptides covering the sequence of ubiquitin. Quantitation was performed by comparing peak areas between labeled and unlabeled versions of each peptide using ABI Multiquant 1.1 software.

Input samples from the wild-type ubiquitin reaction showed a mixture of K11, K48, and K63-linked polyubiquitin chains, while reactions with ubiquitin mutants K11R, K48R and K63R were deficient in K11, K48, and K63 linkages, respectively (FIG. 8E). In the sample immunoprecipitated by the 2A3/2E6 IgG from the reaction using wild-type ubiquitin, the polyubiquitin linkage profiles remained similar to the input material (see FIG. 8E), suggesting that the majority of substrate molecules carry each of the three primary linkages (K11, K48 and K63). Similar results were obtained during characterization of anti-K48 and anti-K63 linkage-specific antibodies (Newton, K. et al. 2008 Cell 134:668-678). Immunoprecipitation with the 2A3/2E6 IgG from the K48R and K63R mutant ubiquitin reactions pulled down autoubiquitinated MuRF1 with polyubiquitin linkage profiles similar to their corresponding inputs. By contrast, the 2A3/2E6 IgG failed to immunoprecipitate polyubiquitin from K11R mutant ubiquitin reactions, due to the lack of the target linkage. This indicates that the 2A3/2E6 IgG is highly specific for K11-linked chains in IPs. As expected, the isotype control antibody was unable to pull down ubiquitin from any of the four reactions.

D. Immunoprecipitation from Cell Lysates

The 2A3/2E6 IgG was also tested for its ability to IP K11-linked polyubiquitin chains from whole cell lysates. 293T cells were grown in high glucose Dulbecco's Modified Eagle Media (DMEM) supplemented with 10% fetal bovine serum (FBS) and 2 mM L-glutamine. Cells were transfected with plasmids to over-express human wild-type ubiquitin, K0 mutant ubiquitin (all seven lysines mutated to arginine), or were mock transfected (FIG. 9A). Transfections were performed according to the manufacturer's instructions using 25 µg of DNA and 75 µL of Lipofectamine 2000 (Invitrogen) per five 10 cm plates. Forty-eight hours after transfection the cells were harvested and lysed as described above. The total protein concentration of each lysate was adjusted to 10 mg/mL in 8 M urea. Lysates were then diluted to 4 M urea with IP buffer (20 mM Tris, pH 7.5, 135 mM NaCl, 1% Triton X-100, 10% glycerol, 1 mM EDTA, 1.5 mM $MgCl_2$) resulting in a total protein concentration of 5 mg/mL. A volume of 1 mL (5 mg of total protein) was used per IP reaction.

In addition to IPs performed with the 2A3/2E6 IgG, a human kappa IgG1 isotype control antibody that does not specifically bind to any form of ubiquitin (Genentech) was also used. Each IP reaction was precleared with 100 µL of Protein A Dynabeads (Invitrogen) at 25° C. for two hours with rotation followed by centrifugation at 14,000 rpm for 2 minutes to remove precipitated material. Beads were captured with a magnet and supernatants were transferred to new tubes. Forty µg of 2A3/2E6 or control IgG was added to each IP and incubated at 25° C. overnight with rotation. The next day the IgG was captured with 200 µL of Protein A Dynabeads per IP by incubating at 25° C. for 15 minutes with rotation. Beads were captured and washed five times with 1 mL of 4 M urea IP buffer (4 M urea, 20 mM Tris, pH 7.5, 135 mM NaCl, 1% Triton X-100, 10% glycerol, 1 mM EDTA, 1.5 mM $MgCl_2$) and then five times with 1 mL of PBS, capturing between each wash. During the final wash the beads were transferred to a new tube. The IP material was eluted by resuspending the beads in 15 µL of 1×LDS sample buffer (Invitrogen) with reducing agent and incubating at 70° C. for ten minutes. For western blot analysis 0.1% of the 5 mg/mL whole cell lysate (input) and 10% of the IP material was run on a 4-12% Bis Tris NuPAGE 1.0 mm gel (Invitrogen) under reducing conditions in MES buffer (Invitrogen). Western blots were carried out as described above, using the pan-ubiquitin P4D1 antibody. For mass spectrometry analysis, 10% of the 5 mg/mL whole cell lysate (input) and 90% of the IP material was run a 4-12% Bis Tris NuPAGE 1.0 mm gel (Invitrogen) under reducing conditions in MES buffer (Invitrogen). The gel was stained with SimplyBlue stain (Invitrogen).

In the mock transfected lysate relatively little polyubiquitin was present and immunoprecipitated by 2A3/2E6 (FIG. 9A). When wild-type ubiquitin was overexpressed polyubiquitin chains within the whole cell lysate were greatly increased along with polyubiquitin chains pulled down by 2A3/2E6, suggesting that K11-linked polyubiquitin chains are upregulated upon ubiquitin over-expression. Surprisingly, when the K0 mutant ubiquitin (which has all lysine residues mutated to arginines and therefore cannot form polyubiquitin chains containing isopeptide bonds) is overexpressed, polyubiquitin chains are also highly upregulated. This suggests that over-expression of K0 leads to increased synthesis of polyubiquitin chains containing endogenous ubiquitin. A large portion of these chains must have been K11-linked since 2A3/2E6 was able to IP them. To determine whether that was indeed the case, mass spectrophotometric analysis was performed as described above, with the exception that gel pieces were incubated on ice for 45 minutes with 20 ng/µL modified sequencing grade trypsin (Promega) diluted in 50 mM ammonium bicarbonate/5% ACN and then the trypsin solution was removed and replaced with 50 mM ammonium bicarbonate/5% ACN prior to overnight digestion at 37° C. Two molecular weight regions from the coomassie stained polyacrylamide gel corresponding to >188 kDa were analyzed (FIGS. 9B and 9C).

Quantitative analysis of these samples showed enrichment of K11 linkages in the immunoprecipitations relative to the percentage of K11 linkages present in the input lysates (FIGS. 9C and 9D). The detection of significant levels of K48 and K63 linkages suggested that individual substrates commonly carry ubiquitin chains of different linkages either as heterogeneous mixed-linkage chains, or possibly as homogenous chains on separate substrate lysines. Immunoprecipitations performed with an isotype control Ab revealed negligible amounts of ubiquitin in chains in all cases (data not shown), consistent with the western blot results in FIG. 9A.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A nucleic acid encoding an antibody that binds K11-linked polyubiquitin wherein the antibody comprises an HVR-L1 sequence selected from SEQ ID NOs: 2 and 57 to 60, an HVR-L2 sequence selected from SEQ ID NOs: 3 and 61, an HVR-L3 sequence of SEQ ID NO: 4, an HVR-H1 sequence selected from SEQ ID NOs: 6 to 11, an HVR-H2 sequence selected from SEQ ID NOs: 12 to 17 and 67, and an HVR-H3 sequence selected from SEQ ID NOs: 18 to 23, 68 and 69.

2. The nucleic acid of claim 1, wherein the antibody comprises an HVR-L1 sequence selected from SEQ ID NOs: 2 and 57 to 60, an HVR-L2 sequence selected from SEQ ID NOs: 3 and 61, an HVR-L3 sequence of SEQ ID NO: 4, an HVR-H1 sequence of SEQ ID NO: 11, an HVR-H2 sequence selected from SEQ ID NOs: 17 and 67, and an HVR-H3 sequence selected from SEQ ID NOs: 23, 68 and 69.

3. The nucleic acid of claim 1, wherein the antibody comprises an HVR-L1 sequence selected from SEQ ID NOs: 58 and 59, an HVR-L2 sequence of SEQ ID NO: 3, an HVR-L3 sequence of SEQ ID NO: 4, an HVR-H1 sequence of SEQ ID NO: 11, an HVR-H2 sequence of SEQ ID NO: 67, and an sequence of SEQ ID NO: 23.

4. The nucleic acid of claim 1, wherein the antibody comprises comprising an HVR-L1 sequence of SEQ ID NO: 59, an HVR-L2 sequence of SEQ ID NO: 3, an HVR-L3 sequence of SEQ NO: 4, an HVR-H1 sequence of SEQ ID NO: 11, an HVR-H2 sequence of SEQ ID NO: 67, and an HVR-H3 sequence of SEQ ID NO: 23.

5. The nucleic acid of claim 1, wherein the antibody comprises a heavy chain variable region comprising a sequence with at least 95% sequence identity to SEQ ID NO: 72 and a light chain variable region comprising a sequence with at least 95% sequence identity to SEQ ID NO: 65.

6. The nucleic acid of claim 1, wherein the antibody comprises a heavy chain variable region comprising the sequence of SEQ ID NO: 72 and a light chain variable region comprising the sequence of SEQ ID NO: 65.

7. The nucleic acid of claim 1, wherein the antibody comprises light chain and heavy chain amino acid sequences with at least 95% sequence identity to the amino acid sequences of one of the following combinations of sequences: SEQ ID NOs: 5 and 32; SEQ ID NOs: 63 and 32; SEQ ID NOs: 65 and 32; SEQ ID NOs: 5 and 72; SEQ ID NOs: 63 and 72; and SEQ ID NOs: 65 and 72; SEQ ID NOs: 62 and 32; SEQ ID NOs: 64 and 32; SEQ ID NOs: 5 and 70; SEQ ID NOs: 5 and 71; SEQ ID NOs: 66 and 32.

8. The nucleic acid of claim 1, wherein the antibody comprises light chain and heavy chain amino acid sequences of one of the following combinations of sequences: SEQ ID NOs: 5 and 32; SEQ ID NOs: 63 and 32; SEQ ID NOs: 65 and 32; SEQ ID NOs: 5 and 72; SEQ ID NOs: 63 and 72; and SEQ ID NOs: 65 and 72; SEQ ID NOs: 62 and 32; SEQ ID NOs: 64 and 32; SEQ ID NOs: 5 and 70; SEQ ID NOs: 5 and 71; SEQ ID NOs: 66 and 32.

9. The nucleic acid of claim 1, wherein the antibody specifically binds to a K11-linked polyubiquitinated protein.

10. The nucleic acid of claim 1, wherein the antibody is a human antibody, a humanized antibody, a chimeric antibody, or an antibody fragment that binds K11-linked polyubiquitin.

11. A vector comprising the nucleic acid of claim 1.

12. A host cell comprising the nucleic acid of claim 1.

13. A method of producing an antibody that specifically binds a first polyubiquitin comprising a K11 lysine linkage comprising culturing the host cell of claim 12 under conditions wherein the antibody is produced.

14. The method of claim 13, further comprising recovering the antibody from the host cell.

15. An isolated host cell comprising a first polynucleotide sequence encoding the light chain of an antibody that binds K11-linked polyubiquitin and a second polynucleotide sequence encoding the heavy chain of an antibody that binds K11-linked polyubiquitin, wherein the light chain comprises an HVR-L1 sequence selected from SEQ ID NOs: 2 and 57 to 60, an HVR-L2 sequence selected from SEQ ID NOs: 3 and 61, an HVR-L3 sequence of SEQ ID NO: 4; and the heavy chain comprises an HVR-H1 sequence selected from SEQ ID NOs: 6 to 11, an HVR-H2 sequence selected from SEQ ID NOs: 12 to 17 and 67, and an HVR-H3 sequence selected from SEQ ID NOs: 18 to 23, 68 and 69.

16. The host cell of claim 15, wherein the light chain comprises an HVR-L1 sequence selected from SEQ ID NOs: 2 and 57 to 60, an HVR-L2 sequence selected from SEQ ID NOs: 3 and 61, an HVR-L3 sequence of SEQ ID NO: 4; and the heavy chain comprises an HVR-H1 sequence of SEQ ID NO: 11, an HVR-H2 sequence selected from SEQ ID NOs: 17 and 67, and an HVR-H3 sequence selected from SEQ ID NOs: 23, 68 and 69.

17. The host cell of claim 15, wherein the light chain comprises an HVR-L1 sequence selected from SEQ ID NOs: 58 and 59, an HVR-L2 sequence of SEQ ID NO: 3, an HVR-L3sequence of SEQ ID NO: 4; and the heavy chain comprises an HVR-H1 sequence of SEQ ID NO: 11, an HVR-H2 sequence of SEQ ID NO: 67, and an HVR-H3 sequence of SEQ ID NO: 23.

18. The host cell of claim 15, wherein the light chain comprises comprising an HVR-L1 sequence of SEQ ID NO: 59, an HVR-L2 sequence of SEQ ID NO: 3, an HVR-L3 sequence of SEQ ID NO: 4; and the heavy chain comprises an HVR-H1 sequence of SEQ ID NO: 11, an HVR-H2 sequence of SEQ ID NO: 67, and an HVR-H3 sequence of SEQ ID NO: 23.

19. The host cell of claim 15, wherein the heavy chain variable region comprising a sequence with at least 95% sequence identity to SEQ ID NO: 72 and the light chain variable region comprising a sequence with at least 95% sequence identity to SEQ ID NO: 65.

20. The host cell of claim 15, wherein the heavy chain variable region comprising the sequence of SEQ ID NO: 72 and the light chain variable region comprising the sequence of SEQ ID NO: 65.

21. The host cell of claim 15, wherein the light chain variable region and heavy chain variable region amino acid sequences have at least 95% sequence identity to the amino acid sequences of one of the following combinations of sequences: SEQ ID NOs: 5 and 32; SEQ ID NOs: 63 and 32; SEQ ID NOs: 65 and 32; SEQ ID NOs: 5 and 72; SEQ ID NOs: 63 and 72; and SEQ ID NOs: 65 and 72; SEQ ID NOs: 62 and 32; SEQ ID NOs: 64 and 32; SEQ ID NOs: 5 and 70; SEQ ID NOs: 5 and 71; SEQ ID NOs: 66 and 32.

22. The host cell of claim 15, wherein the light chain variable region and heavy chain variable region amino acid sequences are selected from the following combinations of sequences: SEQ ID NOs: 5 and 32; SEQ ID NOs: 63 and 32; SEQ ID NOs: 65 and 32; SEQ ID NOs: 5 and 72; SEQ ID NOs: 63 and 72; and SEQ ID NOs: 65 and 72; SEQ ID NOs: 62 and 32; SEQ ID NOs: 64 and 32; SEQ ID NOs: 5 and 70; SEQ ID NOs: 5 and 71; SEQ ID NOs: 66 and 32.

23. A method of producing an antibody that specifically binds a first polyubiquitin comprising a K11 lysine linkage comprising culturing the host cell of claim 22 under conditions wherein the antibody is produced.

24. The method of claim 23, further comprising recovering the antibody from the host cell.

* * * * *

SEQUENCE LISTING

<160> NUMBER OF SEQ ID NOS: 80

<210> SEQ ID NO 1
<211> LENGTH: 76
<212> TYPE: PRT
<213> ORGANISM: Homo sapiens

<400> SEQUENCE: 1

Met Gln Ile Phe Val Lys Thr Leu Thr Gly Lys Thr Ile Thr Leu
1               5                   10                  15

Glu Val Glu Pro Ser Asp Thr Ile Glu Asn Val Lys Ala Lys Ile
                20                  25                  30

Gln Asp Lys Glu Gly Ile Pro Pro Asp Gln Gln Arg Leu Ile Phe
                35                  40                  45

Ala Gly Lys Gln Leu Glu Asp Gly Arg Thr Leu Ser Asp Tyr Asn
                50                  55                  60

Ile Gln Lys Glu Ser Thr Leu His Leu Val Leu Arg Leu Arg Gly
                65                  70                  75

Gly

<210> SEQ ID NO 2
<211> LENGTH: 11
<212> TYPE: PRT
<213> ORGANISM: Artificial sequence
<220> FEATURE:
<223> OTHER INFORMATION: sequence is synthesized

<400> SEQUENCE: 2

Arg Ala Ser Gln Asp Val Ser Thr Ala Val Ala
1               5                   10

<210> SEQ ID NO 3
<211> LENGTH: 7
<212> TYPE: PRT
<213> ORGANISM: Artificial sequence
<220> FEATURE:
<223> OTHER INFORMATION: sequence is synthesized

<400> SEQUENCE: 3

Ser Ala Ser Phe Leu Tyr Ser
1               5

<210> SEQ ID NO 4
<211> LENGTH: 9
<212> TYPE: PRT
<213> ORGANISM: Artificial sequence
<220> FEATURE:
<223> OTHER INFORMATION: sequence is synthesized

<400> SEQUENCE: 4

Gln Gln Ser Tyr Thr Thr Pro Pro Thr
1               5

<210> SEQ ID NO 5
<211> LENGTH: 107
<212> TYPE: PRT
<213> ORGANISM: Artificial sequence
<220> FEATURE:
<223> OTHER INFORMATION: sequence is synthesized

<400> SEQUENCE: 5

Asp Ile Gln Met Thr Gln Ser Pro Ser Ser Leu Ser Ala Ser Val
1               5                   10                  15

```
Gly Asp Arg Val Thr Ile Thr Cys Arg Ala Ser Gln Asp Val Ser
             20                  25                  30

Thr Ala Val Ala Trp Tyr Gln Gln Lys Pro Gly Lys Ala Pro Lys
         35                  40                  45

Leu Leu Ile Tyr Ser Ala Ser Phe Leu Tyr Ser Gly Val Pro Ser
     50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
             80                  85                  90

Ser Tyr Thr Thr Pro Pro Thr Phe Gly Gln Gly Thr Lys Val Glu
             95                 100                 105

Ile Lys
```

<210> SEQ ID NO 6
<211> LENGTH: 6
<212> TYPE: PRT
<213> ORGANISM: Artificial sequence
<220> FEATURE:
<223> OTHER INFORMATION: sequence is synthesized

<400> SEQUENCE: 6

```
Ser Asn Tyr Trp Ile Ser
 1               5
```

<210> SEQ ID NO 7
<211> LENGTH: 6
<212> TYPE: PRT
<213> ORGANISM: Artificial sequence
<220> FEATURE:
<223> OTHER INFORMATION: sequence is synthesized

<400> SEQUENCE: 7

```
Ser Asn Ser Asp Ile His
 1               5
```

<210> SEQ ID NO 8
<211> LENGTH: 6
<212> TYPE: PRT
<213> ORGANISM: Artificial sequence
<220> FEATURE:
<223> OTHER INFORMATION: sequence is synthesized

<400> SEQUENCE: 8

```
Thr Asp Thr Gly Ile His
 1               5
```

<210> SEQ ID NO 9
<211> LENGTH: 6
<212> TYPE: PRT
<213> ORGANISM: Artificial sequence
<220> FEATURE:
<223> OTHER INFORMATION: sequence is synthesized

<400> SEQUENCE: 9

```
Thr Ser Tyr Trp Ile His
 1               5
```

<210> SEQ ID NO 10
<211> LENGTH: 6
<212> TYPE: PRT
<213> ORGANISM: Artificial sequence
<220> FEATURE:
<223> OTHER INFORMATION: sequence is synthesized

```
<400> SEQUENCE: 10

Ser Gly Ser Asp Ile His
 1               5

<210> SEQ ID NO 11
<211> LENGTH: 6
<212> TYPE: PRT
<213> ORGANISM: Artificial sequence
<220> FEATURE:
<223> OTHER INFORMATION: sequence is synthesized

<400> SEQUENCE: 11

Ser Asn Ser Tyr Ile Ser
 1               5

<210> SEQ ID NO 12
<211> LENGTH: 11
<212> TYPE: PRT
<213> ORGANISM: Artificial sequence
<220> FEATURE:
<223> OTHER INFORMATION: sequence is synthesized

<400> SEQUENCE: 12

Gly Asp Ile Ser Pro Asp Gly Gly Tyr Thr Tyr
 1               5                  10

<210> SEQ ID NO 13
<211> LENGTH: 11
<212> TYPE: PRT
<213> ORGANISM: Artificial sequence
<220> FEATURE:
<223> OTHER INFORMATION: sequence is synthesized

<400> SEQUENCE: 13

Gly Trp Ile Tyr Pro Ala Asp Gly Ser Thr Tyr
 1               5                  10

<210> SEQ ID NO 14
<211> LENGTH: 11
<212> TYPE: PRT
<213> ORGANISM: Artificial sequence
<220> FEATURE:
<223> OTHER INFORMATION: sequence is synthesized

<400> SEQUENCE: 14

Gly Val Ile Ser Pro Ala Ser Gly Tyr Thr Asp
 1               5                  10

<210> SEQ ID NO 15
<211> LENGTH: 11
<212> TYPE: PRT
<213> ORGANISM: Artificial sequence
<220> FEATURE:
<223> OTHER INFORMATION: sequence is synthesized

<400> SEQUENCE: 15

Gly Glu Ile Asn Pro His Asp Gly Ser Thr Asn
 1               5                  10

<210> SEQ ID NO 16
<211> LENGTH: 11
<212> TYPE: PRT
<213> ORGANISM: Artificial sequence
<220> FEATURE:
<223> OTHER INFORMATION: sequence is synthesized
```

```
<400> SEQUENCE: 16

Ala Trp Ile Tyr Pro Ala Asp Gly Ser Thr Tyr
 1               5                   10

<210> SEQ ID NO 17
<211> LENGTH: 11
<212> TYPE: PRT
<213> ORGANISM: Artificial sequence
<220> FEATURE:
<223> OTHER INFORMATION: sequence is synthesized

<400> SEQUENCE: 17

Ala Gly Ile Asn Pro Asn Gly Gly Tyr Thr Tyr
 1               5                   10

<210> SEQ ID NO 18
<211> LENGTH: 11
<212> TYPE: PRT
<213> ORGANISM: Artificial sequence
<220> FEATURE:
<223> OTHER INFORMATION: sequence is synthesized

<400> SEQUENCE: 18

Arg Glu Ser Trp Trp Ser Ala Trp Val Met Asp
 1               5                   10

<210> SEQ ID NO 19
<211> LENGTH: 9
<212> TYPE: PRT
<213> ORGANISM: Artificial sequence
<220> FEATURE:
<223> OTHER INFORMATION: sequence is synthesized

<400> SEQUENCE: 19

Lys Gly Ser Gly Tyr Tyr Ala Met Asp
 1               5

<210> SEQ ID NO 20
<211> LENGTH: 10
<212> TYPE: PRT
<213> ORGANISM: Artificial sequence
<220> FEATURE:
<223> OTHER INFORMATION: sequence is synthesized

<400> SEQUENCE: 20

Arg Asp Ile Tyr Tyr Phe Phe Gly Phe Asp
 1               5                   10

<210> SEQ ID NO 21
<211> LENGTH: 10
<212> TYPE: PRT
<213> ORGANISM: Artificial sequence
<220> FEATURE:
<223> OTHER INFORMATION: sequence is synthesized

<400> SEQUENCE: 21

Arg Glu Val Phe Leu Gly Tyr Ala Met Asp
 1               5                   10

<210> SEQ ID NO 22
<211> LENGTH: 8
<212> TYPE: PRT
<213> ORGANISM: Artificial sequence
<220> FEATURE:
<223> OTHER INFORMATION: sequence is synthesized

<400> SEQUENCE: 22
```

```
Lys Pro Ser Trp Gly Phe Phe Asp
  1               5
```

<210> SEQ ID NO 23
<211> LENGTH: 11
<212> TYPE: PRT
<213> ORGANISM: Artificial sequence
<220> FEATURE:
<223> OTHER INFORMATION: sequence is synthesized

<400> SEQUENCE: 23

```
Arg Glu Trp Tyr Phe Gly Gly Tyr Val Met Asp
  1               5                  10
```

<210> SEQ ID NO 24
<211> LENGTH: 6
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: 1
<223> OTHER INFORMATION: X is selected from serine and threonine
<220> FEATURE:
<221> NAME/KEY: Variant
<222> LOCATION: 2
<223> OTHER INFORMATION: X is selected from asparagine, aspartic acid,
      serine and glycine
<220> FEATURE:
<221> NAME/KEY: Variant
<222> LOCATION: 3
<223> OTHER INFORMATION: X is selected from tyrosine, serine and
      threonine
<220> FEATURE:
<221> NAME/KEY: Variant
<222> LOCATION: 4
<223> OTHER INFORMATION: X is selected from tryptophan, aspartic acid
      and glycine and tyrosine
<220> FEATURE:
<221> NAME/KEY: Variant
<222> LOCATION: 6
<223> OTHER INFORMATION: X is selected from serine and histidine

<400> SEQUENCE: 24

```
Xaa Xaa Xaa Xaa Ile Xaa
  1               5
```

<210> SEQ ID NO 25
<211> LENGTH: 10
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 1
<223> OTHER INFORMATION: X is selected from glycine and alanine
<220> FEATURE:
<221> NAME/KEY: variant
<222> LOCATION: 2
<223> OTHER INFORMATION: X is selected from aspartic acid, tryptophan,
      glycine, glutamic acid and valine
<220> FEATURE:
<221> NAME/KEY: variant
<222> LOCATION: 4
<223> OTHER INFORMATION: X is selected from serine, tyrosine and
      asparagine
<220> FEATURE:
<221> NAME/KEY: variant
<222> LOCATION: 6
<223> OTHER INFORMATION: X is selected from aspartic acid, alanine,
      histidine and asparagine

```
<220> FEATURE:
<221> NAME/KEY: variant
<222> LOCATION: 8
<223> OTHER INFORMATION: X is selected from tyrosine and serine
<220> FEATURE:
<221> NAME/KEY: variant
<222> LOCATION: 10
<223> OTHER INFORMATION: X is selected from tyrosine, aspartic acid and
      asparagine

<400> SEQUENCE: 25

Xaa Xaa Ile Xaa Pro Xaa Gly Xaa Thr Xaa
 1               5                  10

<210> SEQ ID NO 26
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 1
<223> OTHER INFORMATION: X is selected from arginine and lysine
<220> FEATURE:
<221> NAME/KEY: variant
<222> LOCATION: 2
<223> OTHER INFORMATION: X is selected from glutamic acid, glycine,
      aspartic acid and proline
<220> FEATURE:
<221> NAME/KEY: variant
<222> LOCATION: 3
<223> OTHER INFORMATION: X is selected from serine, isoleucine, valine
      and tryptophan
<220> FEATURE:
<221> NAME/KEY: variant
<222> LOCATION: 4
<223> OTHER INFORMATION: X is selected from tryptophan, glycine,
      tyrosine and phenylalanine
<220> FEATURE:
<221> NAME/KEY: variant
<222> LOCATION: 5
<223> OTHER INFORMATION: X is selected from tryptophan, tyrosine,
      leucine, glycine and phenylalanine
<220> FEATURE:
<221> NAME/KEY: variant
<222> LOCATION: 6
<223> OTHER INFORMATION: X is selected from serine, tyrosine,
      phenylalanine and glycine
<220> FEATURE:
<221> NAME/KEY: variant
<222> LOCATION: 7
<223> OTHER INFORMATION: X is selected from alanine, phenylalanine,
      tyrosine and glycine, or is not present
<220> FEATURE:
<221> NAME/KEY: variant
<222> LOCATION: 8
<223> OTHER INFORMATION: X is selected from tryptophan, glycine, alanine
      and tyrosine, or is not present
<220> FEATURE:
<221> NAME/KEY: variant
<222> LOCATION: 9
<223> OTHER INFORMATION: X is valine or is not present
<220> FEATURE:
<221> NAME/KEY: variant
<222> LOCATION: 10
<223> OTHER INFORMATION: X is selected from methionine and phenylalanine

<400> SEQUENCE: 26

Xaa Xaa Xaa Xaa Xaa Xaa Xaa Xaa Xaa Xaa Asp
 1               5                  10

<210> SEQ ID NO 27
<211> LENGTH: 120
<212> TYPE: PRT
```

<213> ORGANISM: Artificial sequence
<220> FEATURE:
<223> OTHER INFORMATION: sequence is synthesized

<400> SEQUENCE: 27

Glu Val Gln Leu Val Glu Ser Gly Gly Gly Leu Val Gln Pro Gly
 1               5                  10                  15
Gly Ser Leu Arg Leu Ser Cys Ala Ala Ser Gly Phe Thr Phe Ser
            20                  25                  30
Asn Tyr Trp Ile Ser Trp Val Arg Gln Ala Pro Gly Lys Gly Leu
        35                  40                  45
Glu Trp Val Gly Asp Ile Ser Pro Asp Gly Gly Tyr Thr Tyr Tyr
    50                  55                  60
Ala Asp Ser Val Lys Gly Arg Phe Thr Ile Ser Ala Asp Thr Ser
65                  70                  75
Lys Asn Thr Ala Tyr Leu Gln Met Asn Ser Leu Arg Ala Glu Asp
                80                  85                  90
Thr Ala Val Tyr Tyr Cys Ala Arg Glu Ser Trp Trp Ser Ala Trp
            95                 100                 105
Val Met Asp Tyr Trp Gly Gln Gly Thr Leu Val Thr Val Ser Ser
        110                 115                 120

<210> SEQ ID NO 28
<211> LENGTH: 118
<212> TYPE: PRT
<213> ORGANISM: Artificial sequence
<220> FEATURE:
<223> OTHER INFORMATION: sequence is synthesized

<400> SEQUENCE: 28

Glu Val Gln Leu Val Glu Ser Gly Gly Gly Leu Val Gln Pro Gly
 1               5                  10                  15
Gly Ser Leu Arg Leu Ser Cys Ala Ala Ser Gly Phe Thr Phe Ser
            20                  25                  30
Asn Ser Asp Ile His Trp Val Arg Gln Ala Pro Gly Lys Gly Leu
        35                  40                  45
Glu Trp Val Gly Trp Ile Tyr Pro Ala Asp Gly Ser Thr Tyr Tyr
    50                  55                  60
Ala Asp Ser Val Lys Gly Arg Phe Thr Ile Ser Ala Asp Thr Ser
65                  70                  75
Lys Asn Thr Ala Tyr Leu Gln Met Asn Ser Leu Arg Ala Glu Asp
                80                  85                  90
Thr Ala Val Tyr Tyr Cys Ala Lys Gly Ser Gly Tyr Tyr Ala Met
            95                 100                 105
Asp Tyr Trp Gly Gln Gly Thr Leu Val Thr Val Ser Ser
        110                 115

<210> SEQ ID NO 29
<211> LENGTH: 119
<212> TYPE: PRT
<213> ORGANISM: Artificial sequence
<220> FEATURE:
<223> OTHER INFORMATION: sequence is synthesized

<400> SEQUENCE: 29

Glu Val Gln Leu Val Glu Ser Gly Gly Gly Leu Val Gln Pro Gly
 1               5                  10                  15
Gly Ser Leu Arg Leu Ser Cys Ala Ala Ser Gly Phe Thr Phe Thr
            20                  25                  30

```
Asp Thr Gly Ile His Trp Val Arg Gln Ala Pro Gly Lys Gly Leu
            35                  40                  45

Glu Trp Val Gly Val Ile Ser Pro Ala Ser Gly Tyr Thr Asp Tyr
        50                  55                  60

Ala Asp Ser Val Lys Gly Arg Phe Thr Ile Ser Ala Asp Thr Ser
65                  70                  75

Lys Asn Thr Ala Tyr Leu Gln Met Asn Ser Leu Arg Ala Glu Asp
            80                  85                  90

Thr Ala Val Tyr Tyr Cys Ala Arg Asp Ile Tyr Tyr Phe Phe Gly
        95                  100                 105

Phe Asp Tyr Trp Gly Gln Gly Thr Leu Val Thr Val Ser Ser
                110                 115

<210> SEQ ID NO 30
<211> LENGTH: 119
<212> TYPE: PRT
<213> ORGANISM: Artificial sequence
<220> FEATURE:
<223> OTHER INFORMATION: sequence is synthesized

<400> SEQUENCE: 30

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Thr
            20                  25                  30

Ser Tyr Trp Ile His Trp Val Arg Gln Ala Pro Gly Lys Gly Leu
            35                  40                  45

Glu Trp Val Gly Glu Ile Asn Pro His Asp Gly Ser Thr Asn Tyr
        50                  55                  60

Ala Asp Ser Val Lys Gly Arg Phe Thr Ile Ser Ala Asp Thr Ser
65                  70                  75

Lys Asn Thr Ala Tyr Leu Gln Met Asn Ser Leu Arg Ala Glu Asp
            80                  85                  90

Thr Ala Val Tyr Tyr Cys Ala Arg Glu Val Phe Leu Gly Tyr Ala
        95                  100                 105

Met Asp Tyr Trp Gly Gln Gly Thr Leu Val Thr Val Ser Ser
                110                 115

<210> SEQ ID NO 31
<211> LENGTH: 117
<212> TYPE: PRT
<213> ORGANISM: Artificial sequence
<220> FEATURE:
<223> OTHER INFORMATION: sequence is synthesized

<400> SEQUENCE: 31

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

Gly Ser Asp Ile His Trp Val Arg Gln Ala Pro Gly Lys Gly Leu
            35                  40                  45

Glu Trp Val Ala Trp Ile Tyr Pro Ala Asp Gly Ser Thr Tyr Tyr
        50                  55                  60

Ala Asp Ser Val Lys Gly Arg Phe Thr Ile Ser Ala Asp Thr Ser
65                  70                  75

Lys Asn Thr Ala Tyr Leu Gln Met Asn Ser Leu Arg Ala Glu Asp
```

```
                      80                  85                  90
Thr Ala Val Tyr Tyr Cys Ala Lys Pro Ser Trp Gly Phe Phe Asp
                          95                 100                 105
Tyr Trp Gly Gln Gly Thr Leu Val Thr Val Ser Ser
                         110                 115

<210> SEQ ID NO 32
<211> LENGTH: 120
<212> TYPE: PRT
<213> ORGANISM: Artificial sequence
<220> FEATURE:
<223> OTHER INFORMATION: sequence is synthesized

<400> SEQUENCE: 32

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Ser
                 20                  25                  30

Asn Ser Tyr Ile Ser Trp Val Arg Gln Ala Pro Gly Lys Gly Leu
                 35                  40                  45

Glu Trp Val Ala Gly Ile Asn Pro Asn Gly Gly Tyr Thr Tyr Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Glu Trp Tyr Phe Gly Gly Tyr
                 95                 100                 105

Val Met Asp Tyr Trp Gly Gln Gly Thr Leu Val Thr Val Ser Ser
                110                 115                 120

<210> SEQ ID NO 33
<211> LENGTH: 43
<212> TYPE: DNA
<213> ORGANISM: Artificial sequence
<220> FEATURE:
<223> OTHER INFORMATION: sequence is synthesized

<400> SEQUENCE: 33
tcttgtgaca aaactcacta ataacgcatg aaacagctag agg                    43

<210> SEQ ID NO 34
<211> LENGTH: 43
<212> TYPE: DNA
<213> ORGANISM: Artificial sequence
<220> FEATURE:
<223> OTHER INFORMATION: sequence is synthesized

<400> SEQUENCE: 34
cctctagctg tttcatgcgt tattagtgag ttttgtcaca aga                    43

<210> SEQ ID NO 35
<211> LENGTH: 36
<212> TYPE: DNA
<213> ORGANISM: Artificial sequence
<220> FEATURE:
<223> OTHER INFORMATION: sequence is synthesized

<400> SEQUENCE: 35
tcttgtgaca aaactcacag tggcggtggc tctggt                            36
```

<210> SEQ ID NO 36
<211> LENGTH: 33
<212> TYPE: DNA
<213> ORGANISM: Artificial sequence
<220> FEATURE:
<223> OTHER INFORMATION: sequence is synthesized

<400> SEQUENCE: 36
gtcaccatca cctgctaagc cagtcaggat gtg                          33

<210> SEQ ID NO 37
<211> LENGTH: 34
<212> TYPE: DNA
<213> ORGANISM: Artificial sequence
<220> FEATURE:
<223> OTHER INFORMATION: sequence is synthesized

<400> SEQUENCE: 37
gaagcttctg atttactaag catccttcct ctac                         34

<210> SEQ ID NO 38
<211> LENGTH: 34
<212> TYPE: DNA
<213> ORGANISM: Artificial sequence
<220> FEATURE:
<223> OTHER INFORMATION: sequence is synthesized

<400> SEQUENCE: 38
gcaacttatt actgttaaca atcttatact actc                         34

<210> SEQ ID NO 39
<211> LENGTH: 87
<212> TYPE: DNA
<213> ORGANISM: Artificial sequence
<220> FEATURE:
<223> OTHER INFORMATION: sequence is synthesized

<400> SEQUENCE: 39
gaggacactg ccgtctatta ttgtgctcgt gaggcctcgt aactgccccc        50
ctacgttatg gactactggg gtcaaggaac actagtc                      87

<210> SEQ ID NO 40
<211> LENGTH: 75
<212> TYPE: DNA
<213> ORGANISM: Artificial sequence
<220> FEATURE:
<223> OTHER INFORMATION: sequence is synthesized
<220> FEATURE:
<221> NAME/KEY: modified base
<222> LOCATION: 22-54
<223> OTHER INFORMATION: a, c, g or t
<220> FEATURE:
<221> NAME/KEY: Misc-feature
<222> LOCATION: 22-54
<223> OTHER INFORMATION: see specification as filed for detailed
      description of substitutions and specific embodiments

<400> SEQUENCE: 40
gatagggtca ccatcacctg cnnnnnnnnn nnnnnnnnn nnnnnnnnn          50 nnnntggtat caacagaaac cagga                                   75

<210> SEQ ID NO 41
<211> LENGTH: 66
<212> TYPE: DNA
<213> ORGANISM: Artificial sequence
<220> FEATURE:
<223> OTHER INFORMATION: sequence is synthesized

```
<220> FEATURE:
<221> NAME/KEY: modified base
<222> LOCATION: 25-45
<223> OTHER INFORMATION: a, c, g or t
<220> FEATURE:
<221> NAME/KEY: Misc-feature
<222> LOCATION: 25-45
<223> OTHER INFORMATION: see specification as filed for detailed
      description of substitutions and specific embodiments

<400> SEQUENCE: 41
aaagctccga agcttctgat ttacnnnnnn nnnnnnnnnn nnnnggagt              50 cccttctcgc ttctct                                                  66

<210> SEQ ID NO 42
<211> LENGTH: 69
<212> TYPE: DNA
<213> ORGANISM: Artificial sequence
<220> FEATURE:
<223> OTHER INFORMATION: sequence is synthesized
<220> FEATURE:
<221> NAME/KEY: modified base
<222> LOCATION: 22-48
<223> OTHER INFORMATION: a, c, g or t
<220> FEATURE:
<221> NAME/KEY: Misc-feature
<222> LOCATION: 22-48
<223> OTHER INFORMATION: see specification as filed for detailed
      description or substitutions and specific embodiments

<400> SEQUENCE: 42
gacttcgcaa cttattactg tnnnnnnnnn nnnnnnnnnn nnnnnnnntt              50
cggacagggt accaaggtg                                                69

<210> SEQ ID NO 43
<211> LENGTH: 55
<212> TYPE: DNA
<213> ORGANISM: Artificial sequence
<220> FEATURE:
<223> OTHER INFORMATION: sequence is synthesized
<220> FEATURE:
<221> NAME/KEY: variant
<222> LOCATION: 19
<223> OTHER INFORMATION: N is guanine or adenine
<220> FEATURE:
<221> NAME/KEY: variant
<222> LOCATION: 20
<223> OTHER INFORMATION: N is guanine, adenine, or thymine
<220> FEATURE:
<221> NAME/KEY: variant
<222> LOCATION: 22
<223> OTHER INFORMATION: N is guanine or adenine
<220> FEATURE:
<221> NAME/KEY: variant
<222> LOCATION: 23
<223> OTHER INFORMATION: N is guanine or thymine
<220> FEATURE:
<221> NAME/KEY: variant
<222> LOCATION: 25
<223> OTHER INFORMATION: N is guanine or adenine
<220> FEATURE:
<221> NAME/KEY: variant
<222> LOCATION: 26
<223> OTHER INFORMATION: N is guanine, cytosine, or adenine
<220> FEATURE:
<221> NAME/KEY: variant
<222> LOCATION: 27
<223> OTHER INFORMATION: N is adenine or thymine
<220> FEATURE:
<221> NAME/KEY: variant
<222> LOCATION: 29
<223> OTHER INFORMATION: N is guanine, adenine, cytosine, or thymine
<220> FEATURE:
```

```
<221> NAME/KEY: variant
<222> LOCATION: 30
<223> OTHER INFORMATION: N is adenine or thymine
<220> FEATURE:
<221> NAME/KEY: variant
<222> LOCATION: 32
<223> OTHER INFORMATION: N is adenine, cytosine, or thymine

<400> SEQUENCE: 43
acctgccgtg ccagtcagnn tnntnnnann tntgtagcct ggtatcaaca            50
gaaac                                                             55

<210> SEQ ID NO 44
<211> LENGTH: 55
<212> TYPE: DNA
<213> ORGANISM: Artificial sequence
<220> FEATURE:
<223> OTHER INFORMATION: sequence is synthesized
<220> FEATURE:
<221> NAME/KEY: variant
<222> LOCATION: 19
<223> OTHER INFORMATION: N is guanine or adenine
<220> FEATURE:
<221> NAME/KEY: variant
<222> LOCATION: 20
<223> OTHER INFORMATION: N is guanine, adenine, or thymine
<220> FEATURE:
<221> NAME/KEY: variant
<222> LOCATION: 22
<223> OTHER INFORMATION: N is guanine or adenine
<220> FEATURE:
<221> NAME/KEY: variant
<222> LOCATION: 23
<223> OTHER INFORMATION: N is guanine or thymine
<220> FEATURE:
<221> NAME/KEY: variant
<222> LOCATION: 25
<223> OTHER INFORMATION: N is guanine or adenine
<220> FEATURE:
<221> NAME/KEY: variant
<222> LOCATION: 26
<223> OTHER INFORMATION: N is guanine, cytosine, or adenine
<220> FEATURE:
<221> NAME/KEY: variant
<222> LOCATION: 27
<223> OTHER INFORMATION: N is adenine or thymine
<220> FEATURE:
<221> NAME/KEY: variant
<222> LOCATION: 29
<223> OTHER INFORMATION: N is guanine, adenine, cytosine, or thymine
<220> FEATURE:
<221> NAME/KEY: variant
<222> LOCATION: 30
<223> OTHER INFORMATION: N is adenine or thymine
<220> FEATURE:
<221> NAME/KEY: variant
<222> LOCATION: 32
<223> OTHER INFORMATION: N is adenine, cytosine, or thymine

<400> SEQUENCE: 44
acctgccgtg ccagtcagnn tnntnnnann tntctggcct ggtatcaaca            50
gaaac                                                             55

<210> SEQ ID NO 45
<211> LENGTH: 48
<212> TYPE: DNA
<213> ORGANISM: Artificial sequence
<220> FEATURE:
<223> OTHER INFORMATION: sequence is synthesized
<220> FEATURE:
<221> NAME/KEY: variant
<222> LOCATION: 19
<223> OTHER INFORMATION: N is guanine or thymine
```

```
<220> FEATURE:
<221> NAME/KEY: variant
<222> LOCATION: 20
<223> OTHER INFORMATION: N is guanine, thymine, or cytosine
<220> FEATURE:
<221> NAME/KEY: variant
<222> LOCATION: 29
<223> OTHER INFORMATION: N is guanine, cytosine, or adenine

<400> SEQUENCE: 45
ccgaagcttc tgatttacnn ggcatccanc ctctactctg gagtccct          48

<210> SEQ ID NO 46
<211> LENGTH: 54
<212> TYPE: DNA
<213> ORGANISM: Artificial sequence
<220> FEATURE:
<223> OTHER INFORMATION: sequence is synthesized
<220> FEATURE:
<221> NAME/KEY: variant
<222> LOCATION: 19
<223> OTHER INFORMATION: N is guanine or thymine
<220> FEATURE:
<221> NAME/KEY: variant
<222> LOCATION: 20
<223> OTHER INFORMATION: N is guanine, thymine, or cytosine
<220> FEATURE:
<221> NAME/KEY: variant
<222> LOCATION: 29
<223> OTHER INFORMATION: N is guanine, cytosine, or adenine
<220> FEATURE:
<221> NAME/KEY: variant
<222> LOCATION: 35
<223> OTHER INFORMATION: N is adenine or cytosine

<400> SEQUENCE: 46
ccgaagcttc tgatttacnn ggcatccanc ctcgnatctg gagtcccttc         50
tcgc                                                          54

<210> SEQ ID NO 47
<211> LENGTH: 57
<212> TYPE: DNA
<213> ORGANISM: Artificial sequence
<220> FEATURE:
<223> OTHER INFORMATION: sequence is synthesized
<220> FEATURE:
<221> NAME/KEY: variant
<222> LOCATION: 23
<223> OTHER INFORMATION: N is adenine or cytosine
<220> FEATURE:
<221> NAME/KEY: variant
<222> LOCATION: 25
<223> OTHER INFORMATION: N is guanine, adenine, or thymine
<220> FEATURE:
<221> NAME/KEY: variant
<222> LOCATION: 26
<223> OTHER INFORMATION: N is adenine or cytosine
<220> FEATURE:
<221> NAME/KEY: variant
<222> LOCATION: 28
<223> OTHER INFORMATION: N is guanine or adenine
<220> FEATURE:
<221> NAME/KEY: variant
<222> LOCATION: 29
<223> OTHER INFORMATION: N is guanine, cytosine, or adenine
<220> FEATURE:
<221> NAME/KEY: variant
<222> LOCATION: 31
<223> OTHER INFORMATION: N is guanine, adenine, cytosine, or thymine
<220> FEATURE:
<221> NAME/KEY: variant
<222> LOCATION: 32
<223> OTHER INFORMATION: N is adenine, cytosine, or thymine
<220> FEATURE:
```

<221> NAME/KEY: variant
<222> LOCATION: 37
<223> OTHER INFORMATION: N is thymine or cytosine
<220> FEATURE:
<221> NAME/KEY: variant
<222> LOCATION: 38
<223> OTHER INFORMATION: N is guanine or thymine

<400> SEQUENCE: 47
gcaacttatt actgtcagca atntnncnnt nntcctnnga cgttcggaca    50
gggtacc    57

<210> SEQ ID NO 48
<211> LENGTH: 57
<212> TYPE: DNA
<213> ORGANISM: Artificial sequence
<220> FEATURE:
<223> OTHER INFORMATION: sequence is snythesized
<220> FEATURE:
<221> NAME/KEY: variant
<222> LOCATION: 23
<223> OTHER INFORMATION: N is adenine or cytosine
<220> FEATURE:
<221> NAME/KEY: variant
<222> LOCATION: 25
<223> OTHER INFORMATION: N is guanine, adenine, or thymine
<220> FEATURE:
<221> NAME/KEY: variant
<222> LOCATION: 26
<223> OTHER INFORMATION: N is adenine or cytosine
<220> FEATURE:
<221> NAME/KEY: variant
<222> LOCATION: 28
<223> OTHER INFORMATION: N is guanine or adenine
<220> FEATURE:
<221> NAME/KEY: variant
<222> LOCATION: 29
<223> OTHER INFORMATION: N is guanine, cytosine, or adenine
<220> FEATURE:
<221> NAME/KEY: variant
<222> LOCATION: 31
<223> OTHER INFORMATION: N is guanine, adenine, cytosine, or thymine
<220> FEATURE:
<221> NAME/KEY: variant
<222> LOCATION: 32
<223> OTHER INFORMATION: N is adenine cytosine or thymine
<220> FEATURE:
<221> NAME/KEY: variant
<222> LOCATION: 38
<223> OTHER INFORMATION: N is adenine or thymine

<400> SEQUENCE: 48
gcaacttatt actgtcagca atntnncnnt nntccttnta cgttcggaca    50
gggtacc    57

<210> SEQ ID NO 49
<211> LENGTH: 57
<212> TYPE: DNA
<213> ORGANISM: Artificial sequence
<220> FEATURE:
<223> OTHER INFORMATION: sequence is synthesized
<220> FEATURE:
<221> NAME/KEY: variant
<222> LOCATION: 22
<223> OTHER INFORMATION: N is guanine or cytosine
<220> FEATURE:
<221> NAME/KEY: variant
<222> LOCATION: 23
<223> OTHER INFORMATION: N is guanine or adenine
<220> FEATURE:
<221> NAME/KEY: variant
<222> LOCATION: 25
<223> OTHER INFORMATION: N is guanine, adenine, or thymine

```
<220> FEATURE:
<221> NAME/KEY: variant
<222> LOCATION: 26
<223> OTHER INFORMATION: N is adenine or cytosine
<220> FEATURE:
<221> NAME/KEY: variant
<222> LOCATION: 28
<223> OTHER INFORMATION: N is guanine or adenine
<220> FEATURE:
<221> NAME/KEY: variant
<222> LOCATION: 29
<223> OTHER INFORMATION: N is guanine, cytosine, or adenine
<220> FEATURE:
<221> NAME/KEY: variant
<222> LOCATION: 31
<223> OTHER INFORMATION: N is guanine, adenine, cytosine or thymine
<220> FEATURE:
<221> NAME/KEY: variant
<222> LOCATION: 32
<223> OTHER INFORMATION: N is adenine, cytosine, or thymine
<220> FEATURE:
<221> NAME/KEY: variant
<222> LOCATION: 37
<223> OTHER INFORMATION: N is thymine or cytosine
<220> FEATURE:
<221> NAME/KEY: variant
<222> LOCATION: 38
<223> OTHER INFORMATION: N is guanine or thymine

<400> SEQUENCE: 49
gcaacttatt actgtcagca anntnncnnt nntcctnnga cgttcggaca           50
gggtacc                                                         57

<210> SEQ ID NO 50
<211> LENGTH: 57
<212> TYPE: DNA
<213> ORGANISM: Artificial sequence
<220> FEATURE:
<223> OTHER INFORMATION: sequence is snythesized
<220> FEATURE:
<221> NAME/KEY: variant
<222> LOCATION: 22
<223> OTHER INFORMATION: N is guanine or cytosine
<220> FEATURE:
<221> NAME/KEY: variant
<222> LOCATION: 23
<223> OTHER INFORMATION: N is guanine or adenine
<220> FEATURE:
<221> NAME/KEY: variant
<222> LOCATION: 25
<223> OTHER INFORMATION: N is guanine, adenine, or thymine
<220> FEATURE:
<221> NAME/KEY: variant
<222> LOCATION: 26
<223> OTHER INFORMATION: N is adenine or cytosine
<220> FEATURE:
<221> NAME/KEY: variant
<222> LOCATION: 28
<223> OTHER INFORMATION: N is guanine or adenine
<220> FEATURE:
<221> NAME/KEY: variant
<222> LOCATION: 29
<223> OTHER INFORMATION: N is guanine, cytosine, or adenine
<220> FEATURE:
<221> NAME/KEY: variant
<222> LOCATION: 31
<223> OTHER INFORMATION: N is guanine, adenine, cytosine, or thymine
<220> FEATURE:
<221> NAME/KEY: variant
<222> LOCATION: 32
<223> OTHER INFORMATION: N is adenine, cytosine, or thymine
<220> FEATURE:
<221> NAME/KEY: variant
<222> LOCATION: 38
<223> OTHER INFORMATION: N is adenine or thymine
```

```
<400> SEQUENCE: 50
gcaacttatt actgtcagca anntnncnnt nntccttnta cgttcggaca       50
gggtacc                                                      57

<210> SEQ ID NO 51
<211> LENGTH: 54
<212> TYPE: DNA
<213> ORGANISM: Artificial sequence
<220> FEATURE:
<223> OTHER INFORMATION: sequence is synthesized
<220> FEATURE:
<221> NAME/KEY: modified base
<222> LOCATION: 19-30
<223> OTHER INFORMATION: a, c, g or t
<220> FEATURE:
<221> NAME/KEY: Misc-feature
<222> LOCATION: 19-30 and 34-36
<223> OTHER INFORMATION: see specification as filed for detailed
      description of substitutions and specific embodiments
<220> FEATURE:
<221> NAME/KEY: modified base
<222> LOCATION: 34-36
<223> OTHER INFORMATION: a, c, g or t

<400> SEQUENCE: 51
acttattact gtcagcaann nnnnnnnnnn cctnnnacgt tcggacaggg       50
tacc                                                         54

<210> SEQ ID NO 52
<211> LENGTH: 54
<212> TYPE: DNA
<213> ORGANISM: Artificial sequence
<220> FEATURE:
<223> OTHER INFORMATION: sequence is synthesized
<220> FEATURE:
<221> NAME/KEY: modified base
<222> LOCATION: 19-30
<223> OTHER INFORMATION: a, c, g or t
<220> FEATURE:
<221> NAME/KEY: Misc-feature
<222> LOCATION: 19-30
<223> OTHER INFORMATION: see specification as filed for detailed
      description of substitutions and specific embodiments

<400> SEQUENCE: 52
acttattact gtcagcaann nnnnnnnnnn ccttwtacgt tcggacaggg       50
tacc                                                         54

<210> SEQ ID NO 53
<211> LENGTH: 54
<212> TYPE: DNA
<213> ORGANISM: Artificial sequence
<220> FEATURE:
<223> OTHER INFORMATION: sequence is synthesized
<220> FEATURE:
<221> NAME/KEY: modified base
<222> LOCATION: 19-30, 34-35
<223> OTHER INFORMATION: a, c, g or t
<220> FEATURE:
<221> NAME/KEY: Misc-feature
<222> LOCATION: 19-30, 34-35
<223> OTHER INFORMATION: see specification as filed for detailed
      description of substitutions and specific embodiments

<400> SEQUENCE: 53
acttattact gtcagcaann nnnnnnnnnn cctnngacgt tcggacaggg       50
tacc                                                         54
```

<210> SEQ ID NO 54
<211> LENGTH: 51
<212> TYPE: DNA
<213> ORGANISM: Artificial sequence
<220> FEATURE:
<223> OTHER INFORMATION: sequence is synthesized
<220> FEATURE:
<221> NAME/KEY: modified base
<222> LOCATION: 22-30
<223> OTHER INFORMATION: a, c, g or t
<220> FEATURE:
<221> NAME/KEY: Misc-feature
<222> LOCATION: 22-30
<223> OTHER INFORMATION: see specification as filed for detailed description of substitutions and specific embodiments

<400> SEQUENCE: 54
gcagcttctg gcttcacctt cnnnnnnnnn tatattagct gggtgcgtca          50
g                                                              51

<210> SEQ ID NO 55
<211> LENGTH: 55
<212> TYPE: DNA
<213> ORGANISM: Artificial sequence
<220> FEATURE:
<223> OTHER INFORMATION: sequence is synthesized
<220> FEATURE:
<221> NAME/KEY: modified base
<222> LOCATION: 19-21
<223> OTHER INFORMATION: a, c, g or t
<220> FEATURE:
<221> NAME/KEY: Misc-feature
<222> LOCATION: 19-21, 25-27 and 31-36
<223> OTHER INFORMATION: see specification as filed for detailed description of substitutions and specific embodiments
<220> FEATURE:
<221> NAME/KEY: modified base
<222> LOCATION: 25-27
<223> OTHER INFORMATION: a, c, g or t
<220> FEATURE:
<221> NAME/KEY: modified base
<222> LOCATION: 31-36
<223> OTHER INFORMATION: a, c, g or t

<400> SEQUENCE: 55
ggcctggaat gggttgctnn nattnnncct nnnnnnggtt atacttacta          50
tgccg                                                          55

<210> SEQ ID NO 56
<211> LENGTH: 66
<212> TYPE: DNA
<213> ORGANISM: Artificial sequence
<220> FEATURE:
<223> OTHER INFORMATION: sequence is synthesized
<220> FEATURE:
<221> NAME/KEY: modified base
<222> LOCATION: 28-36
<223> OTHER INFORMATION: a, c, g or t
<220> FEATURE:
<221> NAME/KEY: Misc-feature
<222> LOCATION: 28-36 and 40-42
<223> OTHER INFORMATION: see specification as filed for detailed description of substitutions and specific embodiments
<220> FEATURE:
<221> NAME/KEY: modified base
<222> LOCATION: 40-42
<223> OTHER INFORMATION: a, c, g or t

<400> SEQUENCE: 56
gtctattatt gtgctcgtga gtggtacnnn nnnnnntacn nnatggacta          50

```
ctggggtcaa ggaacc                                                     66
```

<210> SEQ ID NO 57
<211> LENGTH: 11
<212> TYPE: PRT
<213> ORGANISM: Artificial sequence
<220> FEATURE:
<223> OTHER INFORMATION: sequence is synthesized

<400> SEQUENCE: 57

Gly Val Ser Gln Asp Val Asp Ser Val Val Ser
 1               5                  10

<210> SEQ ID NO 58
<211> LENGTH: 11
<212> TYPE: PRT
<213> ORGANISM: Artificial sequence
<220> FEATURE:
<223> OTHER INFORMATION: sequence is synthesized

<400> SEQUENCE: 58

Gly Ala Ser His Asn Leu Gly Thr Val Ile Ala
 1               5                  10

<210> SEQ ID NO 59
<211> LENGTH: 11
<212> TYPE: PRT
<213> ORGANISM: Artificial sequence
<220> FEATURE:
<223> OTHER INFORMATION: sequence is synthesized

<400> SEQUENCE: 59

Arg Ala Ser Gln Ile Val Gly Thr Phe Val Ala
 1               5                  10

<210> SEQ ID NO 60
<211> LENGTH: 11
<212> TYPE: PRT
<213> ORGANISM: Artificial sequence
<220> FEATURE:
<223> OTHER INFORMATION: sequence is synthesized

<400> SEQUENCE: 60

Arg Ala Ser Gln Asp Val Glu Thr Phe Val Ala
 1               5                  10

<210> SEQ ID NO 61
<211> LENGTH: 7
<212> TYPE: PRT
<213> ORGANISM: Artificial sequence
<220> FEATURE:
<223> OTHER INFORMATION: sequence is synthesized

<400> SEQUENCE: 61

Asn Gln Glu Phe Val Tyr Ser
 1               5

<210> SEQ ID NO 62
<211> LENGTH: 107
<212> TYPE: PRT
<213> ORGANISM: Artificial sequence
<220> FEATURE:
<223> OTHER INFORMATION: sequence is synthesized

<400> SEQUENCE: 62

Asp Ile Gln Met Thr Gln Ser Pro Ser Ser Leu Ser Ala Ser Val
 1               5                  10                  15

```
Gly Asp Arg Val Thr Ile Thr Cys Gly Val Ser Gln Asp Val Asp
                20                  25                  30

Ser Val Val Ser Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
    65                  70                  75

Ser Ser Leu Gln Pro Glu Asp Phe Ala Thr Tyr Tyr Cys Gln Gln
80                  85                  90

Ser Tyr Thr Thr Pro Pro Thr Phe Gly Gln Gly Thr Lys Val Glu
                95                 100                 105

Ile Lys

<210> SEQ ID NO 63
<211> LENGTH: 107
<212> TYPE: PRT
<213> ORGANISM: Artificial sequence
<220> FEATURE:
<223> OTHER INFORMATION: sequence is synthesized

<400> SEQUENCE: 63

Asp Ile Gln Met Thr Gln Ser Pro Ser Ser Leu Ser Ala Ser Val
1               5                  10                  15

Gly Asp Arg Val Thr Ile Thr Cys Gly Ala Ser His Asn Leu Gly
                20                  25                  30

Thr Val Ile Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
    65                  70                  75

Ser Ser Leu Gln Pro Glu Asp Phe Ala Thr Tyr Tyr Cys Gln Gln
80                  85                  90

Ser Tyr Thr Thr Pro Pro Thr Phe Gly Gln Gly Thr Lys Val Glu
                95                 100                 105

Ile Lys

<210> SEQ ID NO 64
<211> LENGTH: 107
<212> TYPE: PRT
<213> ORGANISM: Artificial sequence
<220> FEATURE:
<223> OTHER INFORMATION: sequence is synthesized

<400> SEQUENCE: 64

Asp Ile Gln Met Thr Gln Ser Pro Ser Ser Leu Ser Ala Ser Val
1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

Leu Leu Ile Tyr Asn Gln Glu Phe Val Tyr Ser Gly Val Pro Ser
        50                  55                  60

Arg Phe Ser Gly Ser Gly Ser Gly Thr Asp Phe Thr Leu Thr Ile
    65                  70                  75
```

```
Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
                95                 100                 105

Ile Lys

<210> SEQ ID NO 65
<211> LENGTH: 107
<212> TYPE: PRT
<213> ORGANISM: Artificial sequence
<220> FEATURE:
<223> OTHER INFORMATION: sequence is synthesized

<400> SEQUENCE: 65

Asp Ile Gln Met Thr Gln Ser Pro Ser Ser Leu Ser Ala Ser Val
 1                5                  10                  15

Gly Asp Arg Val Thr Ile Thr Cys Arg Ala Ser Gln Ile Val Gly
                20                  25                  30

Thr Phe Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
                95                 100                 105

Ile Lys

<210> SEQ ID NO 66
<211> LENGTH: 107
<212> TYPE: PRT
<213> ORGANISM: Artificial sequence
<220> FEATURE:
<223> OTHER INFORMATION: sequence is synthesized

<400> SEQUENCE: 66

Asp Ile Gln Met Thr Gln Ser Pro Ser Ser Leu Ser Ala Ser Val
 1                5                  10                  15

Gly Asp Arg Val Thr Ile Thr Cys Arg Ala Ser Gln Asp Val Glu
                20                  25                  30

Thr Phe Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
                95                 100                 105

Ile Lys

<210> SEQ ID NO 67
<211> LENGTH: 17
<212> TYPE: PRT
<213> ORGANISM: Artificial sequence
```

```
<220> FEATURE:
<223> OTHER INFORMATION: sequence is synthesized

<400> SEQUENCE: 67

Ala Ile Asn Pro Ala Gly Gly Tyr Thr Tyr Tyr Ala Asp Ser Val
 1               5                  10                  15

Lys Gly

<210> SEQ ID NO 68
<211> LENGTH: 11
<212> TYPE: PRT
<213> ORGANISM: Artificial sequence
<220> FEATURE:
<223> OTHER INFORMATION: sequence is synthesized

<400> SEQUENCE: 68

Glu Trp Tyr Phe Asp Gly Tyr Val Met Asp Tyr
 1               5                  10

<210> SEQ ID NO 69
<211> LENGTH: 11
<212> TYPE: PRT
<213> ORGANISM: Artificial sequence
<220> FEATURE:
<223> OTHER INFORMATION: sequence is synthesized

<400> SEQUENCE: 69

Glu Trp Tyr Tyr Gly Gly Tyr Val Met Asp Tyr
 1               5                  10

<210> SEQ ID NO 70
<211> LENGTH: 120
<212> TYPE: PRT
<213> ORGANISM: Artificial sequence
<220> FEATURE:
<223> OTHER INFORMATION: sequence is synthesized

<400> SEQUENCE: 70

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Asn Ser Tyr Ile Ser Trp Val Arg Gln Ala Pro Gly Lys Gly Leu
                35                  40                  45

Glu Trp Val Ala Gly Ile Asn Pro Asn Gly Gly Tyr Thr Tyr Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ala Arg Glu Trp Tyr Phe Asp Gly Tyr
                95                 100                 105

Val Met Asp Tyr Trp Gly Gln Gly Thr Leu Val Thr Val Ser Ser
               110                 115                 120

<210> SEQ ID NO 71
<211> LENGTH: 120
<212> TYPE: PRT
<213> ORGANISM: Artificial sequence
<220> FEATURE:
<223> OTHER INFORMATION: sequence is synthesized

<400> SEQUENCE: 71
```

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

Asn Ser Tyr Ile Ser Trp Val Arg Gln Ala Pro Gly Lys Gly Leu
            35                  40                  45

Glu Trp Val Ala Gly Ile Asn Pro Asn Gly Gly Tyr Thr Tyr Tyr
            50                  55                  60

Ala Asp Ser Val Lys Gly Arg Phe Thr Ile Ser Ala Asp Thr Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Glu Trp Tyr Tyr Gly Gly Tyr
            95                  100                 105

Val Met Asp Tyr Trp Gly Gln Gly Thr Leu Val Thr Val Ser Ser
            110                 115                 120

<210> SEQ ID NO 72
<211> LENGTH: 120
<212> TYPE: PRT
<213> ORGANISM: Artificial sequence
<220> FEATURE:
<223> OTHER INFORMATION: sequence is synthesized

<400> SEQUENCE: 72

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

Asn Ser Tyr Ile Ser Trp Val Arg Gln Ala Pro Gly Lys Gly Leu
            35                  40                  45

Glu Trp Val Ala Ala Ile Asn Pro Ala Gly Gly Tyr Thr Tyr Tyr
            50                  55                  60

Ala Asp Ser Val Lys Gly Arg Phe Thr Ile Ser Ala Asp Thr Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Glu Trp Tyr Phe Gly Gly Tyr
            95                  100                 105

Val Met Asp Tyr Trp Gly Gln Gly Thr Leu Val Thr Val Ser Ser
            110                 115                 120

<210> SEQ ID NO 73
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 1
<223> OTHER INFORMATION: X is selected from arginine and glycine
<220> FEATURE:
<221> NAME/KEY: variant
<222> LOCATION: 2
<223> OTHER INFORMATION: X is selected from alanine and valine
<220> FEATURE:
<221> NAME/KEY: variant
<222> LOCATION: 4
<223> OTHER INFORMATION: X is selected from glutamine and histidine
<220> FEATURE:

```
<221> NAME/KEY: variant
<222> LOCATION: 5
<223> OTHER INFORMATION: X is selected from aspartic acid, asparagine
      and isoleucine
<220> FEATURE:
<221> NAME/KEY: variant
<222> LOCATION: 6
<223> OTHER INFORMATION: X is selected from leucine and valine
<220> FEATURE:
<221> NAME/KEY: variant
<222> LOCATION: 7
<223> OTHER INFORMATION: X is selected from serine, aspartic acid,
      glycine and glutamic acid
<220> FEATURE:
<221> NAME/KEY: variant
<222> LOCATION: 8
<223> OTHER INFORMATION: X is selected from threonine and serine
<220> FEATURE:
<221> NAME/KEY: variant
<222> LOCATION: 9
<223> OTHER INFORMATION: X is selected from alanine, valine and
      phenylalanine
<220> FEATURE:
<221> NAME/KEY: variant
<222> LOCATION: 10
<223> OTHER INFORMATION: X is selected from valine and isoleucine
<220> FEATURE:
<221> NAME/KEY: variant
<222> LOCATION: 11
<223> OTHER INFORMATION: X is selected from alanine and serine

<400> SEQUENCE: 73

Xaa Xaa Ser Xaa Xaa Xaa Xaa Xaa Xaa Xaa Xaa
 1               5                  10

<210> SEQ ID NO 74
<211> LENGTH: 7
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 1
<223> OTHER INFORMATION: X is selected from serine and asparagine
<220> FEATURE:
<221> NAME/KEY: variant
<222> LOCATION: 2
<223> OTHER INFORMATION: X is selected from glutamine and alanine
<220> FEATURE:
<221> NAME/KEY: variant
<222> LOCATION: 3
<223> OTHER INFORMATION: X is selected from glutamic acid and serine
<220> FEATURE:
<221> NAME/KEY: variant
<222> LOCATION: 5
<223> OTHER INFORMATION: X is selected from leucine and valine

<400> SEQUENCE: 74

Xaa Xaa Xaa Phe Xaa Tyr Ser
 1               5

<210> SEQ ID NO 75
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 1
<223> OTHER INFORMATION: X is selected from alanine and glycine
<220> FEATURE:
<221> NAME/KEY: variant
<222> LOCATION: 5
```

<223> OTHER INFORMATION: X is selected from alanine and asparagine

<400> SEQUENCE: 75

Xaa Ile Asn Pro Xaa Gly Gly Tyr Thr Tyr Tyr Ala Asp Ser Val
1               5                   10                  15

Lys Gly

<210> SEQ ID NO 76
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: variant
<222> LOCATION: 4
<223> OTHER INFORMATION: X is selected from phenylalanine and tyrosine
<220> FEATURE:
<221> NAME/KEY: variant
<222> LOCATION: 5
<223> OTHER INFORMATION: X is selected from glycine and aspartic acid

<400> SEQUENCE: 76

Glu Trp Tyr Xaa Xaa Gly Tyr Val Met Asp Tyr
1               5                   10

<210> SEQ ID NO 77
<211> LENGTH: 45
<212> TYPE: DNA
<213> ORGANISM: Artificial sequence
<220> FEATURE:
<223> OTHER INFORMATION: sequence is synthesized

<400> SEQUENCE: 77
ccgaagcttc tgatttacaa ccaggaattc gtgtacagcg gagtc            45

<210> SEQ ID NO 78
<211> LENGTH: 45
<212> TYPE: DNA
<213> ORGANISM: Artificial sequence
<220> FEATURE:
<223> OTHER INFORMATION: sequence is synthesized

<400> SEQUENCE: 78
gactccgctg tacacgaatt cctggttgta atcagaaagc ttcgg            45

<210> SEQ ID NO 79
<211> LENGTH: 107
<212> TYPE: PRT
<213> ORGANISM: Artificial sequence
<220> FEATURE:
<223> OTHER INFORMATION: sequence is synthesized

<400> SEQUENCE: 79

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Arg Ser Gly Thr Asp Phe Thr Leu Thr Ile
                65                  70                  75

```
Ser Ser Leu Gln Pro Glu Asp Phe Ala Thr Tyr Tyr Cys Gln Gln
            80                  85                      90

His Tyr Thr Thr Pro Pro Thr Phe Gly Gln Gly Thr Lys Val Glu
                95                 100                     105

Ile Lys

<210> SEQ ID NO 80
<211> LENGTH: 107
<212> TYPE: PRT
<213> ORGANISM: Artificial sequence
<220> FEATURE:
<223> OTHER INFORMATION: sequence is synthesized

<400> SEQUENCE: 80

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Val Ser
                20                  25                  30

Ser Ala Val Ala Trp Tyr Gln Gln Lys Pro Gly Lys Ala Pro Lys
            35                  40                      45

Leu Leu Ile Tyr Ser Ala Ser Ser Leu Tyr Ser Gly Val Pro Ser
            50                  55                      60

Arg Phe Ser Gly Ser Gly Ser Gly Thr Asp Phe Thr Leu Thr Ile
            65                  70                      75

Ser Ser Leu Gln Pro Glu Asp Phe Ala Thr Tyr Tyr Cys Gln Gln
            80                  85                      90

Ser Tyr Thr Thr Pro Pro Thr Phe Gly Gln Gly Thr Lys Val Glu
                95                 100                     105

Ile Lys
```